(12) United States Patent
Tan et al.

(10) Patent No.: US 10,710,061 B2
(45) Date of Patent: Jul. 14, 2020

(54) ION PAIR CATALYSIS OF TUNGSTATE AND MOLYBDATE

(71) Applicant: Nanyang Technological University, Singapore (SG)

(72) Inventors: Choon-Hong Tan, Singapore (SG); Xinyi Ye, Singapore (SG); Lili Zong, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 16/087,582

(22) PCT Filed: Mar. 22, 2017

(86) PCT No.: PCT/SG2017/050140
§ 371 (c)(1),
(2) Date: Sep. 21, 2018

(87) PCT Pub. No.: WO2017/164813
PCT Pub. Date: Sep. 28, 2017

(65) Prior Publication Data
US 2019/0105646 A1    Apr. 11, 2019

(30) Foreign Application Priority Data

Mar. 22, 2016    (SG) .......................... 10201602244 U

(51) Int. Cl.
*B01J 31/22*    (2006.01)
*C07C 315/02*    (2006.01)
(Continued)

(52) U.S. Cl.
CPC ............ *B01J 31/22* (2013.01); *B01J 27/051* (2013.01); *B01J 27/18* (2013.01); *B01J 31/02* (2013.01);
(Continued)

(58) Field of Classification Search
None
See application file for complete search history.

(56) References Cited

FOREIGN PATENT DOCUMENTS

WO    2016/039691 A1    3/2016

OTHER PUBLICATIONS

Wang et al. (JACS, 137, 10677-10682 (Year: 2015).*
(Continued)

*Primary Examiner* — Yun Qian
(74) *Attorney, Agent, or Firm* — Mintz, Levin, Cohn, Ferris, Glovsky and Popeo, P.C.

(57) ABSTRACT

D The present invention relates to ion pair catalysts (I) comprising the cationic bisguanidinium ligand (A) and diperoxomolybdate anion (B). The present invention also relates to ion pair catalysts (III) comprising the cationic bisguanidinium ligand (C) and peroxotungstate anion (D). It further relates to the use of the said catalysts in the manufacture of enantiomerically enriched sulfoxides.

(I)

(Continued)

(B)

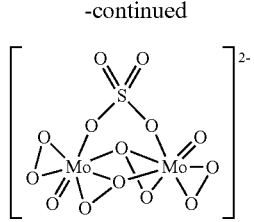

(III)

(C)

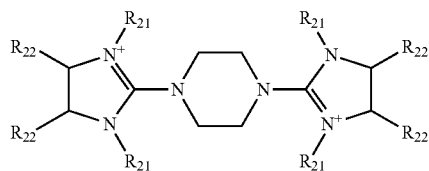

(D)

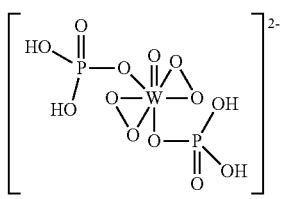

12 Claims, 15 Drawing Sheets

(51) Int. Cl.
| | |
|---|---|
| B01J 31/02 | (2006.01) |
| C07D 403/12 | (2006.01) |
| C07D 401/12 | (2006.01) |
| C07D 333/18 | (2006.01) |
| C07D 333/34 | (2006.01) |
| C07D 277/76 | (2006.01) |
| C07D 213/71 | (2006.01) |
| C07D 405/12 | (2006.01) |
| C07D 235/28 | (2006.01) |
| B01J 27/051 | (2006.01) |
| B01J 27/18 | (2006.01) |
| B01J 35/00 | (2006.01) |
| B01J 37/12 | (2006.01) |
| C07B 53/00 | (2006.01) |
| C07C 317/06 | (2006.01) |
| C07C 279/16 | (2006.01) |
| C07C 317/14 | (2006.01) |
| C07C 317/24 | (2006.01) |
| C07C 317/44 | (2006.01) |

(52) U.S. Cl.
CPC .......... *B01J 35/0006* (2013.01); *B01J 37/12* (2013.01); *C07B 53/00* (2013.01); *C07C 315/02* (2013.01); *C07D 213/71* (2013.01); *C07D 235/28* (2013.01); *C07D 277/76* (2013.01); *C07D 333/18* (2013.01); *C07D 333/34* (2013.01); *C07D 401/12* (2013.01); *C07D 403/12* (2013.01); *C07D 405/12* (2013.01); *B01J 2531/004* (2013.01); *B01J 2531/02* (2013.01); *B01J 2531/64* (2013.01); *B01J 2531/66* (2013.01); *B01J 2540/42* (2013.01); *C07C 279/16* (2013.01); *C07C 317/06* (2013.01); *C07C 317/14* (2013.01); *C07C 317/24* (2013.01); *C07C 317/44* (2013.01)

(56) References Cited

OTHER PUBLICATIONS

Written Opinion completed May 30, 2017 corresponding to PCT/SG2017/050140 filed Mar. 22, 2017 (8 pages).
Written Opinion completed Jun. 17, 2017 corresponding to PCT/SG2017/050140 filed Mar. 22, 2017 (8 pages).
International Search Report dated May 30, 2017 corresponding to PCT/SG2017/050140 filed Mar. 22, 2017 (8 pages).
Sato, Kazuhiko et al., "Oxidation of sulfides to sulfoxides and sulfones with 30% hydrogen peroxide under organic solvent-and halogen-free conditions," *Tetrahedron* (Mar. 20, 2001); 57(13):2469-2476.
Thompson, Dylan J. et al., "Peroxo-dimolybdate catalyst for the oxygenation of organic sulfides by hydrogen peroxide," *Ionorganic Chimica Acta* (available online Sep. 1, 2015); 473:103-109.
Wang, Chao et al., "Enantioselective Oxidation of Alkenes with Potassium Permanganate Catalyzed by Chiral Dicationic Bisguanidinium," *J. Am. Chem. Soc.* (Aug. 3, 2015); 137(33):10677-10682.
Ye, Xinyi et al., "Enantioselective Sulfoxidation Catalyzed by a Bisguanidinium Diphosphatobisperoxotungstate Ion Pair," *Angew. Chem. Int. Ed.* (May 6, 2016); 55(25):7101-7105.
Zong, Lili et al., "Bisguanidinium dinuclear oxodiperoxomolybdosulfate ion pair-catalyzed enantioselective sulfoxidation," *Nat. Commun.* (Nov. 21, 2016); 7:13455:1-7.

* cited by examiner (R,R)-1b n=2 X = Cl (R,R)-1c n=1 X =

[(µ₂-SO₄){Mo₂O₂(µ₂-O₂)₂(O₂)₂}]

A) [Bu$_4$N]$_2$[(μ$_2$-SO$_4$){Mo$_2$O$_2$(μ$_2$-O$_2$)$_2$(O$_2$)$_2$}]

B) (R,R)-1c [Bisguanidinium][(μ$_2$-SO$_4$){Mo$_2$O$_2$(μ$_2$-O$_2$)$_2$(O$_2$)$_2$}]

ION PAIR CATALYSIS OF TUNGSTATE AND MOLYBDATE

FIELD OF INVENTION

The current application relates to compounds for the preparation of enantiopure chiral sulfoxides. The application also relates to methods for the preparation of the same.

BACKGROUND

The listing or discussion of an apparently prior-published document in this specification should not necessarily be taken as an acknowledgement that the document is part of the state of the art or is common general knowledge.

Sodium tungstate-catalyzed epoxidation of α,β-unsaturated acids using $H_2O_2$ in water was first demonstrated by Payne in 1959 and was followed up by Sharpless in 1985 (G. B. Payne, et al., *J. Org. Chem.* 1959, 24, 54; K. S. Kirshenbaum, et al., *J. Org. Chem.* 1985, 50, 1979). Tungstates are known to be polymeric in aqueous solutions and the distribution of the polyoxotungstate species is dependent on pH and concentration. Peroxotungstate complexes are known to be the catalytic species in these reactions (K. A. Jørgensen, *Chem. Rev.* 1989, 89, 431; M. H. Dickman, et al., *Chem. Rev.* 1994, 94, 569; N. Mizuno, et al., *Coordin. Chem. Rev.* 2005, 249, 1944). Investigation by Venturello into the role of phosphate in phase transfer tungstate oxidation reactions, resulted in the isolation and identification of the heteropolyperoxotungstate, $[PO_4\{WO(O_2)_2\}_4]^{3-}$ (C. Venturello, et al., *J. Org. Chem.* 1983, 48, 3831; C. Venturello, et al., *J. Mol. Catal.* 1985, 32, 107). This peroxotungstate species was also postulated to be the catalytically active species for the $H_3PW_{12}O_{40}/H_2O_2$(Keggin's reagent) oxidation system developed by Ishii (Y. Ishii, et al., J. Org. Chem. 1988, 53, 3587; A. J. Bailey, et al., *J. Chem. Soc., Dalton. Trans.* 1995, 1833; D. C. Duncan, et al., *J. Am. Chem. Soc.* 1995, 117, 681) Subsequently, Noyori developed an efficient catalyst suitable on a practical scale with high turnover number. It was found that (aminomethyl)phosphonic acid or phenylphosphonic acid was effective in accelerating the reaction. It was proposed that a 1:1 complex between phosphonic acid and monoperoxotungstate is the active catalyst (R. Noyori, et al., *Chem. Commun.* 2003, 1977). Using this methodology, they furnished olefin epoxidation (K. Sato, et al., *J. Org. Chem.* 1996, 61, 8310) and sulfoxidation (K. Sato, et al., *Tetrahedron* 2001, 57, 2469) in high chemoselectivities.

Molybdenum-based systems have been extensively applied in the field of inorganic, organic and biological chemistry (J. Burke & E. P. Carreiro. in *Comprehensive Inorganic Chemistry II (Second Edition)*, 309-382 (Elsevier, 2013)). Molybdenum metalloenzymes play an important role in the metabolism of nitrogen (Yoshiaki Nishibayashi, *Inorg. Chem.* 54, 9234-9247 (2015)), sulfur, and carbon compounds (R. Hille, et al., *Chem. Rev.* 114, 3963-4038 (2014); Barbara K. Burgess & David J. Lowe, *Chem. Rev.* 96, 2983-3012 (1996); Günter Schwarz, et al., *Nature* 460, 839-847 (2009)). Over recent years, various molybdenum compounds have been developed and successfully applied in a number of organic transformations. In particular, the properties of the oxomolybdenum (VI) anionic species have been comprehensively investigated and described. It is worthy of note that the reactions with organic ligands, strong acids and oxidants allow the formation of numerous ionic complexes of molybdenum. A few heteropolymolybdate complexes (Alan J. Bailey, et al., *J. Chem. Soc., Dalton Trans.*, 1833-1837 (1995); N. Melanie Gresley, et al, *J. Mol. Catal. A: Chem.* 117, 185-198 (1997); Karl-Heinz Tytko & Dieter Gras, (Springer Berlin Heidelberg, 1988) involving nitrate, fluoride, chloride and phosphate groups (Li Mingqiang & Jian Xigao, *Bull. Chem. Soc. Jpn.* 78, 1575-1579 (2005)) have been investigated to afford more structural and catalytic diversity.

Molybdate ions can act as catalysts for the activation of $H_2O_2$ by forming monomeric or polymeric peroxomolybdates, which are highly dependent on pH value of the solution and the quantity of $H_2O_2$(Valeria Conte & Barbara Floris, *Dalton Trans.* 40, 1419-1436 (2011); Michael H. Dickman & Michael T. Pope, *Chem. Rev.* 94, 569-584 (1994)).

The coordination pattern and fine structure of peroxomolybdate anions and corresponding counter cations can have a significant impact on their performance as oxidizing reagents (Xianying Shi & Junfa Wei, *Appl. Organomet. Chem.* 21, 172-176 (2007)). Recently, the coordination chemistry of anionic peroxomolybdate species with different organic ligands such as citric and malic acids (Zhao-Hui Zhou, et al., *Dalton Trans.*, 1393-1399 (2004)), amino acids (Katarzyna Serdiuk, et al., *Transition Met. Chem.* (London) 26, 538-543) and oxalic acid (Andrew C. Dengel, et al., *J. Chem. Soc., Dalton Trans.*, 991-995 (1987); Rajan Deepan Chakravarthy, et al., *Green Chem.* 16, 2190-2196 (2014)) have been systemically investigated. However, the protocol for preparation of peroxomolybdenum complex with a sulfate ligand is limited (Chang G. Kim, et al., *Inorg. Chem.* 32, 2232-2233 (1993); Masato Hashimoto, et al., *J. Coord. Chem.* 37, 349-359 (1996); Fabian Taube, et al., *J. Chem. Soc., Dalton Trans.*, 1002-1008 (2002); Dao-Li Deng, et al., WO2006094577A1 (2006)) only one example using such a system for the catalysis of olefin epoxidation reaction has been reported so far (Laurent Salles, et al., *Bull. Soc. Chim. Fr.* 133, 319-328 (1996)).

The preparation of enantiopure chiral sulfoxides is an important field because new and better methods will enable more convenient access to potential drug molecules (for selected reviews, see: a) I. Fernández, N. Khiar, *Chem. Rev.* 2003, 103, 3651; b) H. B. Kagan, T. O. Luukas, *Transition Metals for Organic Synthesis: Building Blocks and Fine Chemicals, Second Revised and Enlarged Edition.* 2004: 479; c) H. B. Kagan, Wiley-VCH: Weinheim, Germany, 2008; d) G. E. O'Mahony, A. Ford, A. R. Maguire, *J. Sulfur Chem.* 2013, 34, 301).

Currently, the Kagan oxidation is widely used for asymmetric sulfoxidation (H. B. Kagan, F. Rebiere, *Synlett* 1990, 11, 643) but there are emerging methods (F. A. Davis, R. T. Reddy, W. Han, P. J. Carroll, *J. Am. Chem. Soc.* 1992, 114, 1428; J. Legros, C. Bolm, *Angew. Chem. Int. Ed.* 2004, 43, 4225; *Angew. Chem.* 2004, 116, 4321; C. Drago, L. Caggiano, R. F. W. Jackson, *Angew. Chem. Int. Ed.* 2005, 44, 7221; *Angew. Chem.* 2005, 117, 7387; J. Fujisaki, K. Matsumoto, K. Matsumoto, T. Katsuki, *J. Am. Chem. Soc.* 2011, 133, 56) to prepare chiral sulfoxides including some recent breakthroughs utilizing imidodiphosphoric acid (S. Liao, I. Ćorić, Q. Wang, B. List, *J. Am. Chem. Soc.* 2012, 134, 10765), binuclear titanium chiral complex (S. Bhadra, M. Akakura, H. Yamamoto, *J. Am. Chem. Soc.* 2015, 137, 15612), or pentanidium (L. Zong, X. Ban, C. W. Kee, C.-H. Tan, *Angew. Chem. Int. Ed.* 2014, 53, 11849; *Angew. Chem.* 2014, 126, 12043).

There remains a need for new methods of accessing chiral sulfoxides in high enantiopurities and for catalysts/catalyst systems that can be used to accomplish these as current methods may not be able to work with particular substrate materials of significant interest in the field of pharmaceuticals and the like.

SUMMARY OF INVENTION

It has been surprisingly found that two complexes are particularly good at providing an enantioselective sulfoxidation product. These complexes are a molybdate complex and a tungstate complex. When used herein, the term "complex" may be used interchangeably with "system".

Molybdate System

Disclosed herein is an in situ generated chiral [bisguanidinium]$^{2+}$[($\mu_2$-SO$_4$)Mo$_2$O$_2$($\mu_2$-O$_2$)$_2$(O$_2$)$_2$]$^{2-}$ complex using a chiral bisguanidinium di-cation paired with inorganic sulfato diperoxomolybdate dianion. This complex has been isolated and its structure has been unambiguously confirmed by single crystal X-ray diffraction and $^{95}$Mo NMR technique. The precise control on enantioselectivity in sulfide oxidation indicates the highly synergistic interaction of the dicationic bisguanidinium and anionic diperoxomolybdate ion-pair catalyst.

It has been demonstrated below that this complex acts as the real reactive species in the oxidation reaction of organic thioethers by the transfer of two equivalents of active oxygen atom. Furthermore, the strategy of using chiral dicationic bisguanidinium for the precise control of the dinuclear oxodiperoxomolybdosulfate dianion species [($\mu_2$-SO$_4$) Mo$_2$O$_2$($\mu_2$-O$_2$)$_2$(O$_2$)$_2$] was successfully applied in the highly stereoselective synthesis of Armodafinil in gram-scale. The successful identification of this organic bisguanidinium-inorganic metallic anion complex opens up new paradigms for previously inaccessible reactions. In conclusion, direct enantioselective sulfoxidation using an abundant molybdate salt and environmentally benign aqueous H$_2$O$_2$ has been well established in our present methodology.

Thus, in a first aspect of the invention, there is provided a complex of formula (I), comprising an organic cation (A) and an inorganic anion (B):

(I)

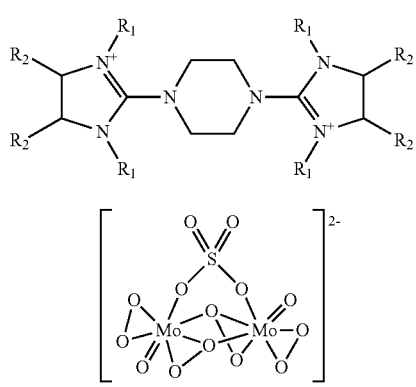

wherein:
each R$_1$ independently represents C$_{1-3}$ alkyl-aryl or C$_{1-3}$ alkyl-Het$^a$, which aryl or Het$^a$ groups are unsubstituted or are substituted by from one to five R$_3$ substituents;
each R$_2$ independently represents aryl, which group is unsubstituted or substituted by from one to five R$_4$ substituents;

Het$^a$ represents a 4- to 14-membered heterocyclic group containing one or more heteroatoms selected from O, S and N, which heterocyclic group may comprise one, two or three rings;
each R$_3$ and R$_4$ independently represents halo, branched or unbranched C$_{1-6}$ alkyl, branched or unbranched C$_{2-6}$ alkenyl, branched or unbranched C$_{2-6}$ alkynyl; C$_{3-6}$ cycloalkyl, aryl (which latter five groups are unsubstituted or substituted by one or more halogen atoms) or OR$_5$;
R$_5$ represents H, branched or unbranched C$_{1-6}$ alkyl, branched or unbranched C$_{2-6}$ alkenyl, branched or unbranched C$_{2-6}$ alkynyl, C$_{3-6}$ cycloalkyl or aryl (which latter five groups are unsubstituted or substituted by one or more halogen atoms).

In a second aspect of the invention, there is provided a process of manufacturing a sulfoxide, comprising reacting a compound of formula (II):

(II)

in the presence of a complex of formula (I), as defined in the first aspect of the invention (or in any of its embodiments disclosed herein), wherein in the compound of formula (II):
R$_6$ represents H, branched or unbranched C$_{1-6}$ alkyl, branched or unbranched C$_{2-6}$ alkenyl, branched or unbranched C$_{2-6}$ alkynyl, C$_{3-6}$ cycloalkyl (which latter three groups are unsubstituted or substituted by one or more substituents selected from halo, OR$_8$, and C(O)R$_9$), C(O)R$_{10}$, C(O)OR$_{11}$ or OR$_{12}$;
R$_7$ represents CH(R$_{13}$)(R$_{14}$), Het$^b$ or aryl, which latter two groups are unsubstituted or substituted by one or more substituents selected from halo, NO$_2$, CN, branched or unbranched C$_{1-6}$ alkyl (optionally substituted by one or more halo atoms), C(O)R$_{15}$ or OR$_{16}$;
R$_{13}$ and R$_{14}$ each independently represent H, aryl or Het$^c$ (which latter two groups are unsubstituted or substituted by one or more substituents selected from halo, branched or unbranched C$_{1-6}$ alkyl, C(O)R$_{17}$ and OR$_{18}$), provided that at least one of R$_{13}$ and R$_{14}$ is not H;
R$_8$, R$_{12}$, R$_{16}$ and R$_{18}$ each independently represent H, C(O)R$_{19}$ or a branched or unbranched C$_{1-6}$ alkyl optionally substituted by one or more halo atoms;
R$_9$, R$_{10}$, R$_{15}$ and R$_{17}$ each independently represent a branched or unbranched C$_{1-6}$ alkyl (optionally substituted by one or more halo atoms), OR$_{20}$ or N(R$_{20'}$)(R$_{20''}$);
R$_{11}$ represents a branched or unbranched C$_{1-6}$ alkyl (optionally substituted by one or more halo atoms);
R$_{19}$, R$_{20}$, R$_{20'}$, and R$_{20''}$ each independently represent H or a branched or unbranched C$_{1-6}$ alkyl (optionally substituted by one or more halo atoms);
Het$^b$ and Het$^c$ represent a 4- to 14-membered heteroaromatic group containing one or more heteroatoms selected from O, S and N, which heteroaromatic group may comprise one, two or three rings; and
n represents from 1 to 10.

Tungstate System

Also disclosed herein is an enantioselective tungstate-catalyzed sulfoxidation reaction. High enantioselectivities were achieved for a variety of drug-like heterocyclic sulfides under mild conditions using stoichiometric quantities of H$_2$O$_2$, a cheap and environmentally friendly oxidant. Synthetic utility was demonstrated through the preparation of (S)-Lansoprazole, a commercial proton-pump inhibitor. The active ion-pair catalyst was identified to be bisguanidinium diphosphatobisperoxotungstate using Raman spectroscopy and computational studies.

Thus, in a third aspect of the invention, there is provided a complex of formula (III), comprising an organic cation (C) and an inorganic anion (D):

(III)

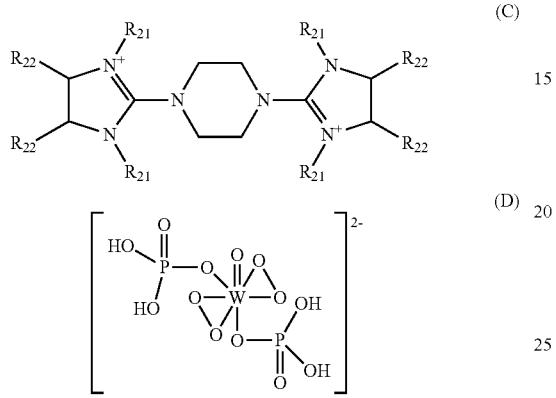

wherein:
each $R_{21}$ independently represents $C_{1-3}$ alkyl-aryl or $C_{1-3}$ alkyl-$Het^d$, which aryl or $Het^d$ groups are unsubstituted or are substituted by from one to five $R_{23}$ substituents;
each $R_{22}$ independently represents aryl, which group is unsubstituted or substituted by from one to five $R_{24}$ substituents;
$Het^d$ represents a 4- to 14-membered heterocyclic group containing one or more heteroatoms selected from O, S and N, which heterocyclic group may comprise one, two or three rings;
each $R_{23}$ and $R_{24}$ independently represents halo, branched or unbranched $C_{1-6}$ alkyl, branched or unbranched $C_{2-6}$ alkenyl, branched or unbranched $C_{2-6}$ alkynyl; $C_{3-6}$ cycloalkyl, aryl (which latter five groups are unsubstituted or substituted by one or more halogen atoms) or $OR_{25}$;
$R_{25}$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl or aryl (which latter five groups are unsubstituted or substituted by one or more halogen atoms).

In a fourth aspect of the invention, there is provided a process of manufacturing a sulfoxide, comprising reacting a compound of formula (IV):

(IV)

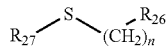

in the presence of a catalytic amount of a complex of formula (III), as defined in the third aspect of the invention (or in any of its embodiments disclosed herein), and at least one molar equivalent of an oxidising agent relative to the compound of formula (IV), wherein in the compound of formula (IV):
$R_{26}$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl, aryl, $Het^e$ (which latter five groups are unsubstituted or substituted by one or more substituents selected from halo, $NO_2$, CN, $C_{1-6}$ alkyl (optionally substituted by one or more halo atoms), and $OR_{28}$), $OR_{29}$, CN, or $C(O)OR_{30}$;
$R_{27}$ represents $Het^f$ or aryl, which groups are unsubstituted or substituted by one or more substituents selected from halo, $NO_2$, CN, branched or unbranched $C_{1-6}$ alkyl (optionally substituted by one or more halo atoms), or $OR_{31}$;
$R_{28}$, $R_{29}$ and $R_{31}$ each independently represent H, $C(O)R_{32}$ or a branched or unbranched $C_{1-6}$ alkyl optionally substituted by one or more halo atoms;
$R_{30}$ and $R_{32}$ each independently represent H or a branched or unbranched $C_{1-6}$ alkyl optionally substituted by one or more halo atoms;
each $Het^e$ independently represents a 4- to 14-membered heterocyclic group containing one or more heteroatoms selected from O, S and N, which heterocyclic group may comprise one, two or three rings; and
$Het^f$ represents a 4- to 14-membered heteroaromatic group containing one or more heteroatoms selected from O, S and N, which heteroaromatic group may comprise one, two or three rings; and
n represents from 1 to 10.

DRAWINGS

Certain embodiments of the present disclosure are described more fully hereinafter with reference to the accompanying drawings.

FIG. 1A depicts an experimental Raman spectrum and vibration diagram of the active species as provided by Example 7. Raman setting: 2 mW, 532 laser power, 30 seconds; FIG. 1B provides a table comparing the experimental and calculated vibrational frequencies of various bond/bonds from the Raman spectrum.

FIG. 2 provides a representation of an ion-pair BG1-P2W generated from computational studies using ONIOM optimization, where Oc represents a peroxo-oxygen that may be a possible reaction site;

FIG. 3 provides a schematic illustration of a possible mechanism of the formation and re-generation of ion-pair BG1-P2W from silver tungstate in the presence of chiral dicationic bisguanidinium;

FIG. 4 provides a molecular structure of ion-pair BG1-P2W and its use in the asymmetric sulfoxidation of heterocyclic sulfides;

FIG. 5 depicts molecular structures of various chiral bisguanidinium derivatives;

FIG. 6A depicts a ORTEP diagram showing X-ray crystal structure of the anionic part of complex (R,R)-1c; FIG. 6B depicts a solid-state structure of complex (R,R)-1c with ellipsoids (drawn using Mercury) shown at the 50% probability level. DMF and $Et_2O$ molecules, and H-atoms have been omitted for clarity;

Figure 10A:
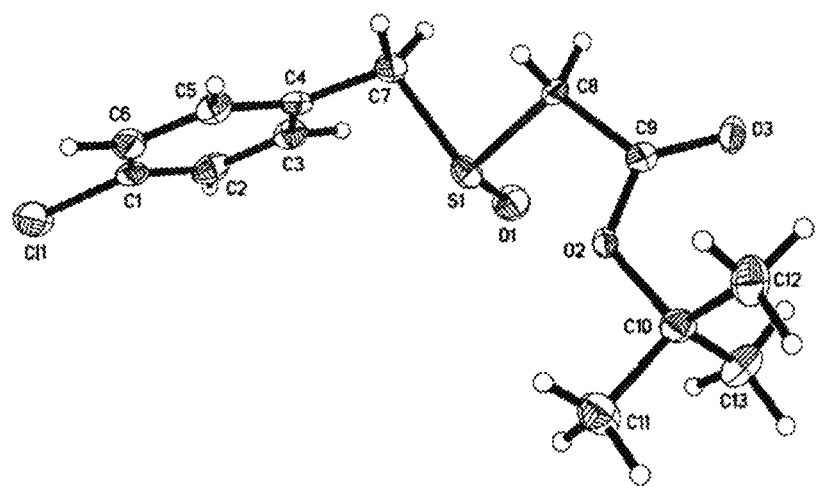
Figure 10B:
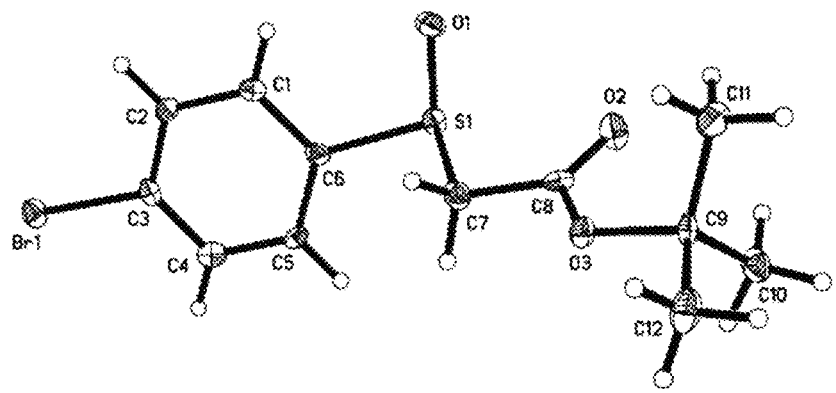
Figure 10C:
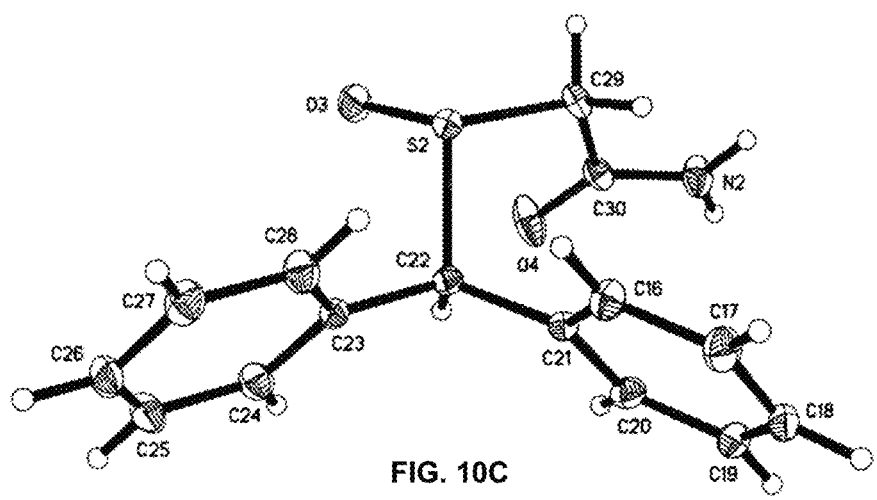
Figure 11:
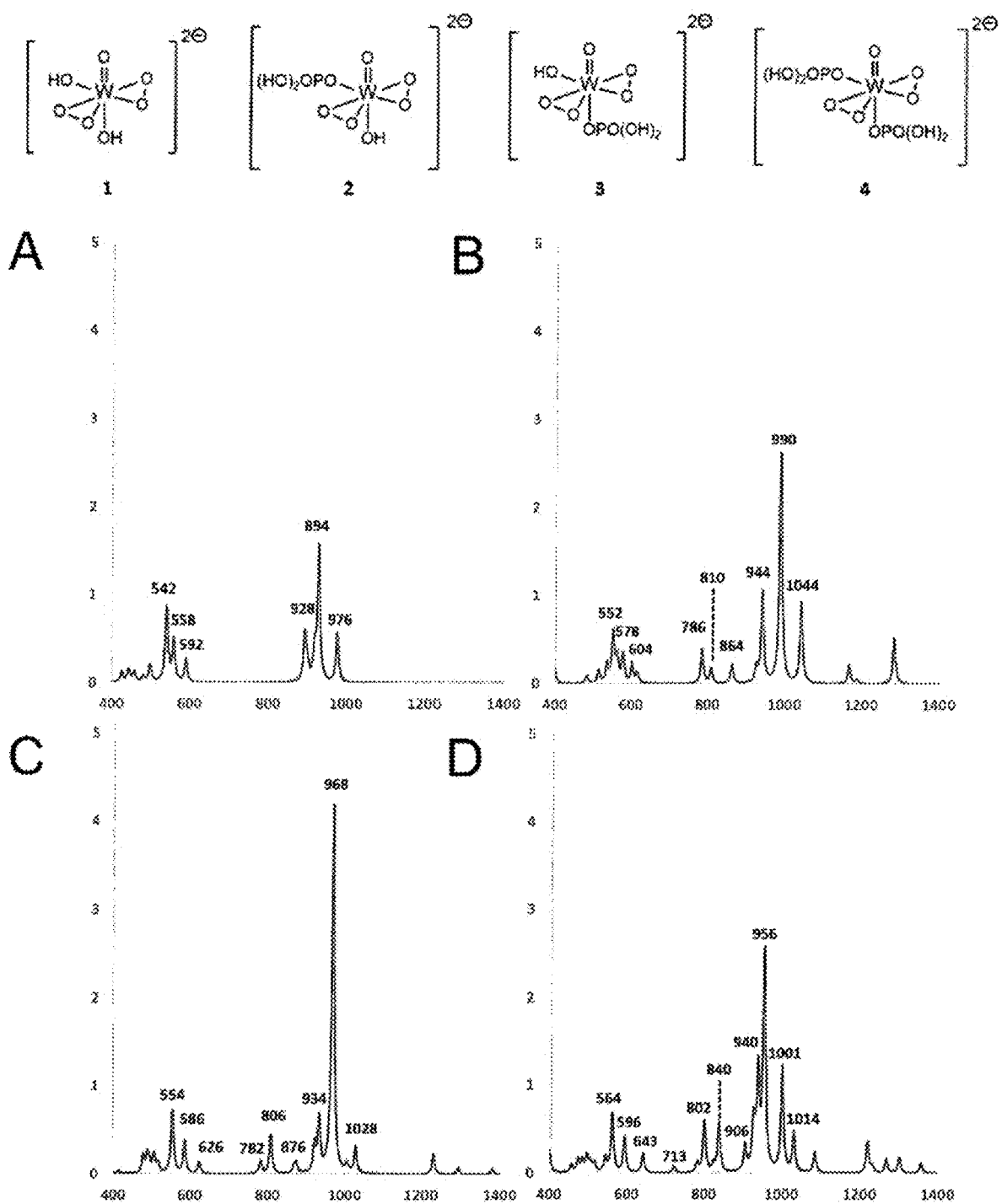
Figure 12:
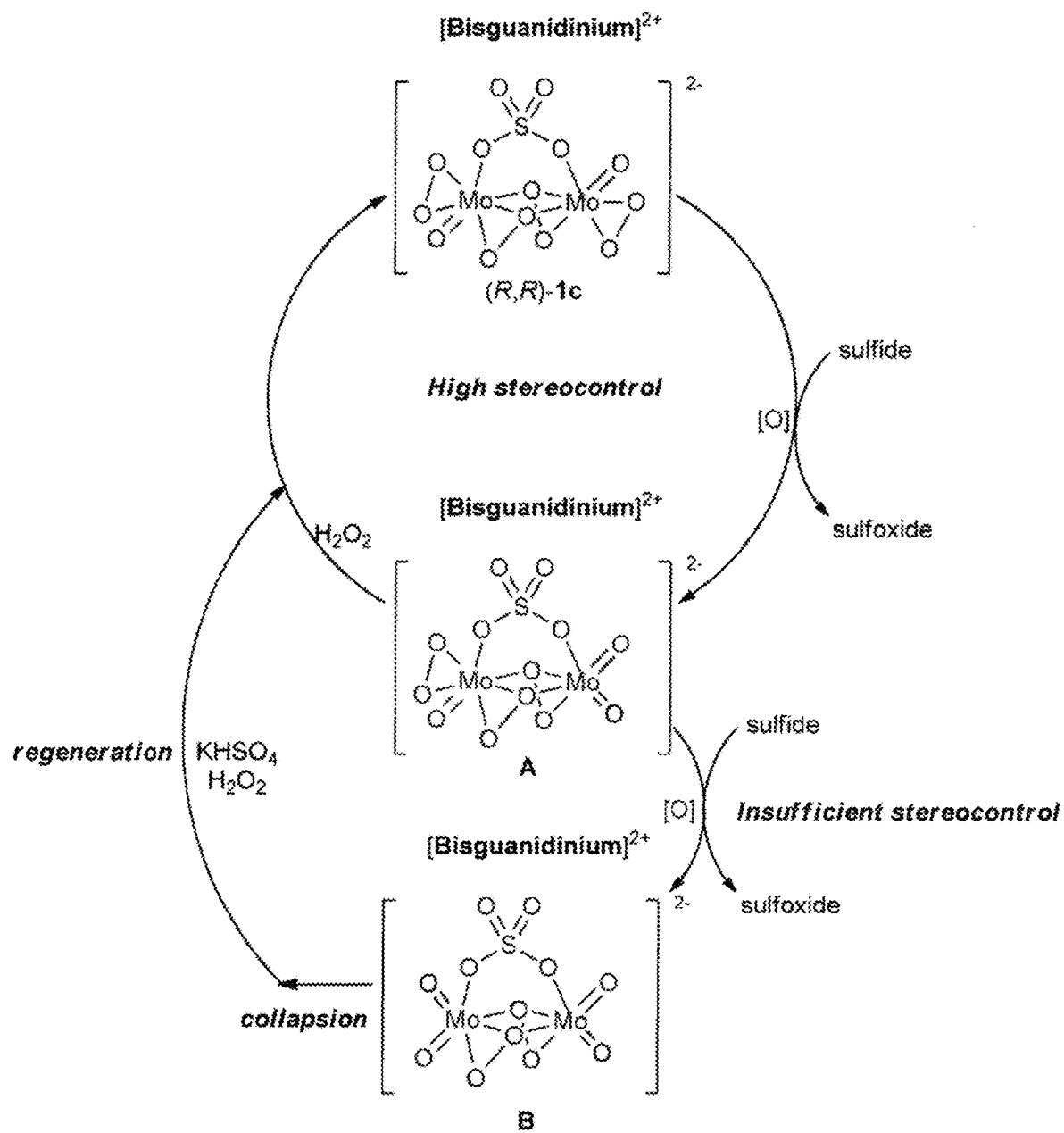
Figure 13A:
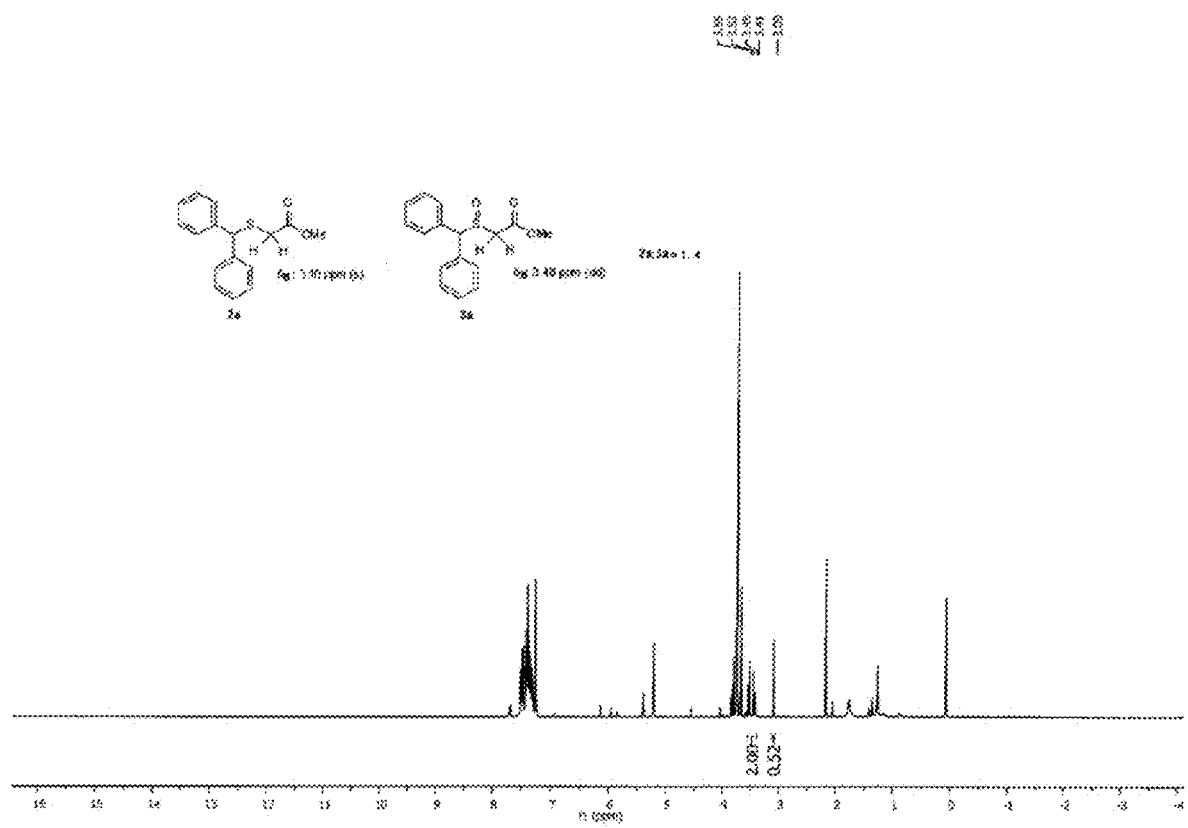
Figure 13B:
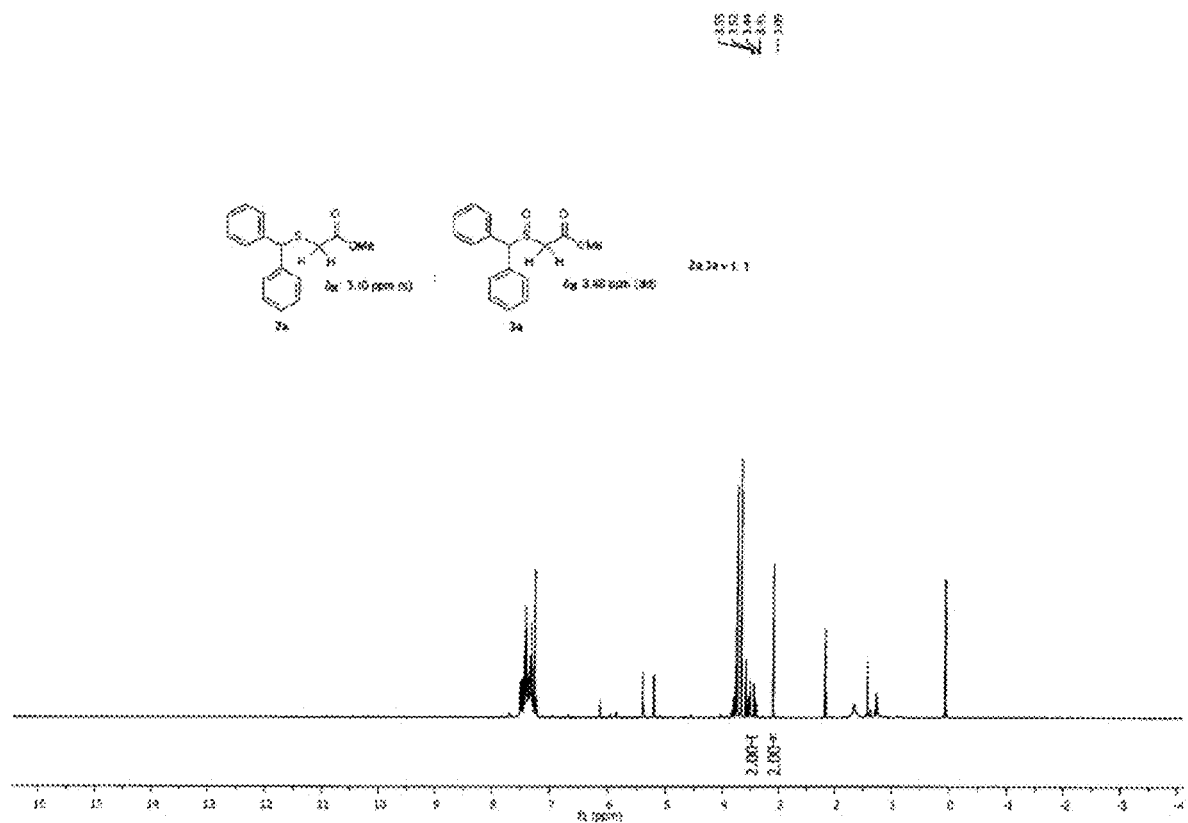
Figure 14:
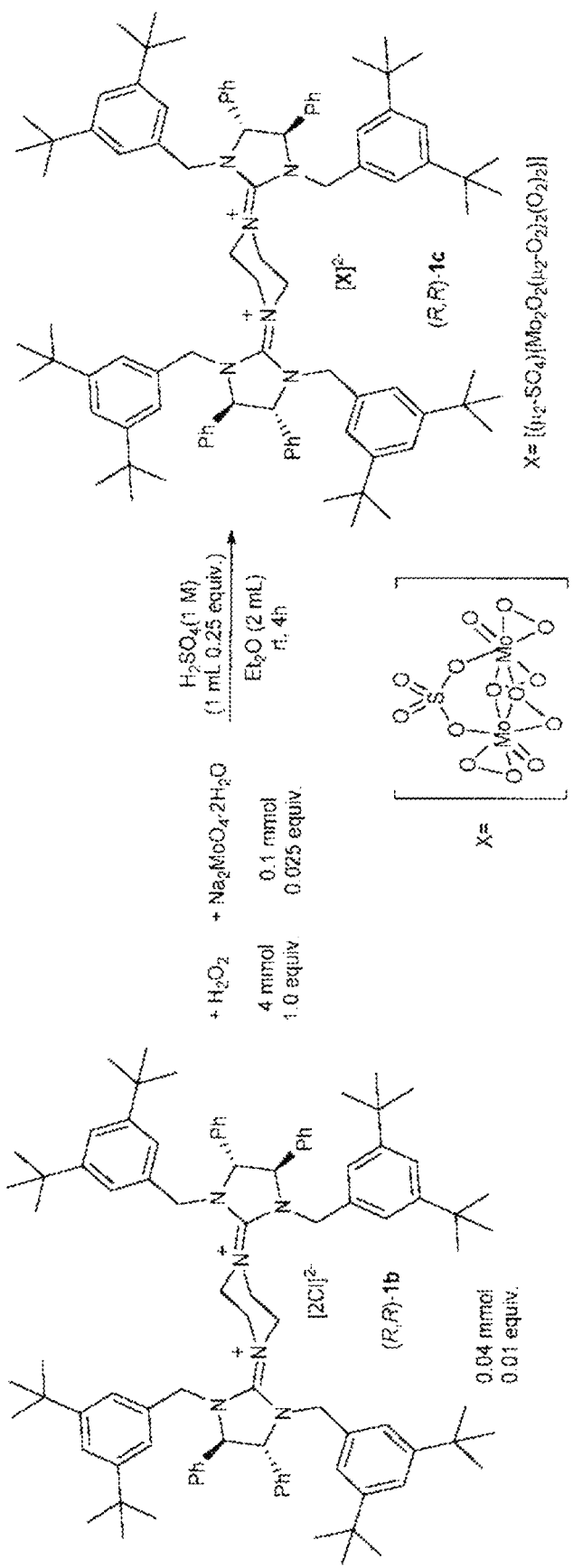
Figure 15:
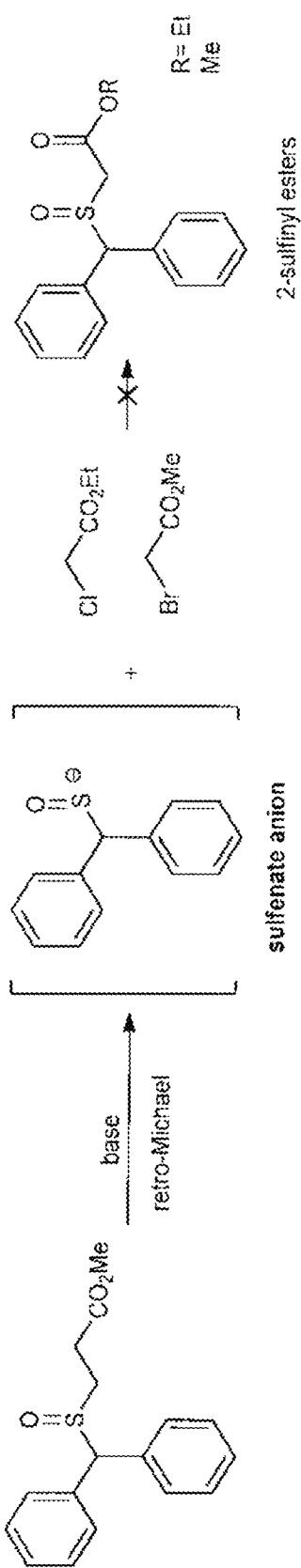
Figure 16:
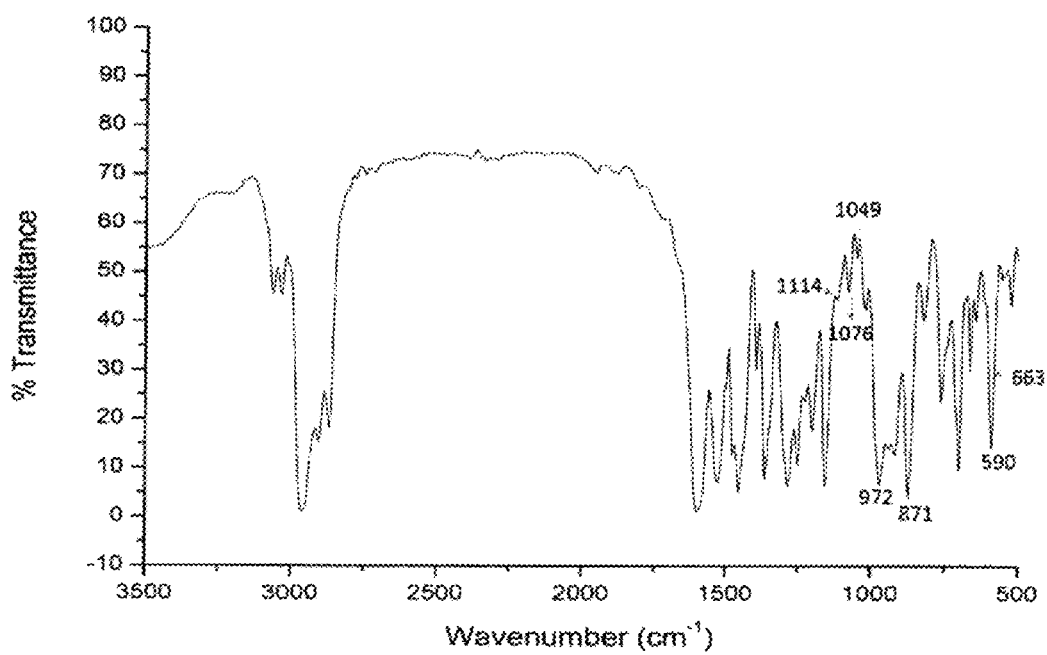

FIGS. 9A-E depict ORTEP diagrams showing X-ray crystal structure of products (S)-2'a, (S)-2'b, (S)-2'c, (S)-2'q and (S)-2'm respectively;

FIGS. 10A-C depict ORTEP diagrams showing X-ray crystal structure of products (R)-8f, (S)-10f and (R)-13 respectively;

FIG. 11 depicts possible coordination configurations of peroxotungstate complexes and their predicted Raman spectra computed at B3LYP/B1 theory level, where (A) represents dihydroxide 1, (B) represents monophosphate 2, (C) represents axial monophosphate 3, and (D) represents diphosphate 4;

FIG. 12 provides a possible mechanistic cycle of complex (R,R)-1c;

FIG. 13A and FIG. 13B depict the NMR spectra for Table 6 entries 2 and 3 respectively;

FIG. 14 depicts a synthetic pathway for (R,R)-1c;

FIG. 15 depicts unsuccessful attempts to oxidize 2-sulfinyl esters using a sulfenate anion strategy; and FIG. 16 depicts the Infrared spectrum of (R,R)-1c.

Figure 17:
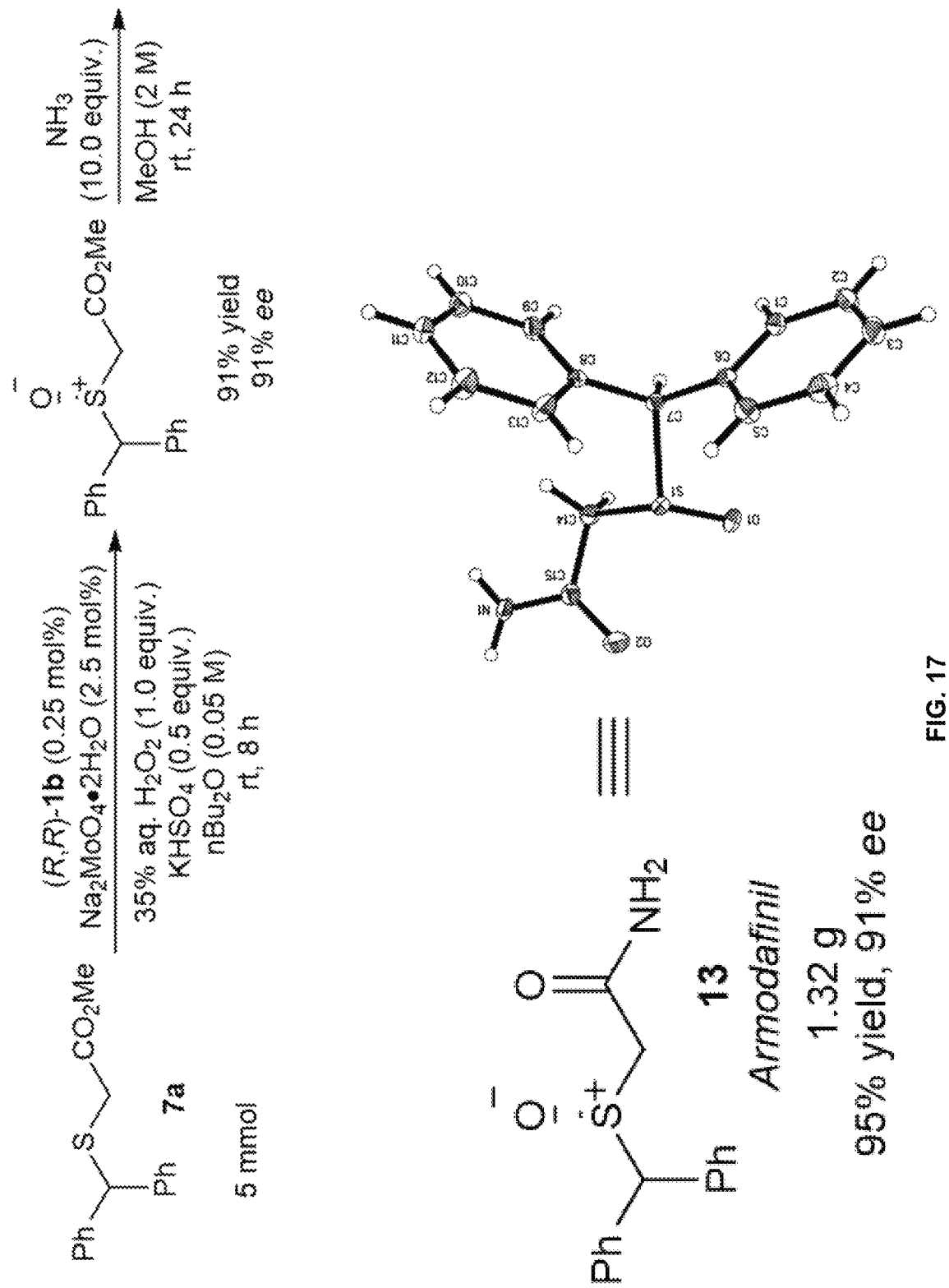

FIG. 17 depicts the gram-scale synthesis pathway of armodafinil by using 0.25 mol % of (R,R)-1b described in Example 13.

DESCRIPTION

As noted herein, two catalytic complexes for the sulfoxidation of sulfides are disclosed herein that enable the sulfoxidation of a broad range of substrate sulfides in enantioenriched forms.

The first of these systems is a complex of formula (I), comprising an organic cation (A) and an inorganic anion (B):

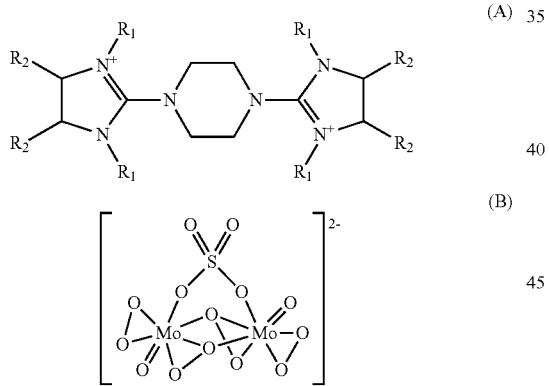

wherein:
each $R_1$ independently represents $C_{1-3}$ alkyl-aryl or $C_{1-3}$ alkyl-Het$^a$, which aryl or Het$^a$ groups are unsubstituted or are substituted by from one to five $R_3$ substituents;
each $R_2$ independently represents aryl, which group is unsubstituted or substituted by from one to five $R_4$ substituents;
Het$^a$ represents a 4- to 14-membered heterocyclic group containing one or more heteroatoms selected from O, S and N, which heterocyclic group may comprise one, two or three rings;
each $R_3$ and $R_4$ independently represents halo, branched or unbranched $C_{1-6}$ alkyl, branched or unbranched $C_{2-6}$ alkenyl, branched or unbranched $C_{2-6}$ alkynyl; $C_{3-6}$ cycloalkyl, aryl (which latter five groups are unsubstituted or substituted by one or more halogen atoms) or $OR_5$;
$R_5$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl or aryl (which latter five groups are unsubstituted or substituted by one or more halogen atoms).

The second of these systems is a complex of formula (III), comprising an organic cation (C) and an inorganic anion (D):

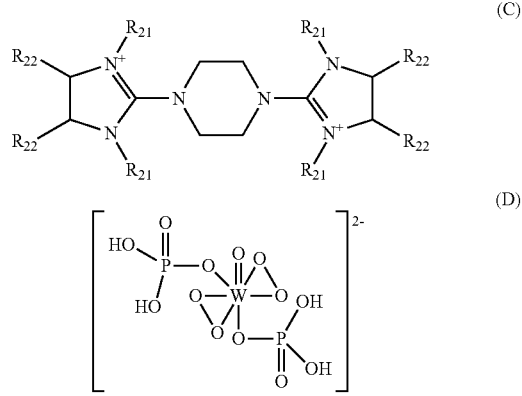

wherein:
each $R_{21}$ independently represents $C_{1-3}$ alkyl-aryl or $C_{1-3}$ alkyl-Het$^d$, which aryl or Het$^d$ groups are unsubstituted or are substituted by from one to five $R_{23}$ substituents;
each $R_{22}$ independently represents aryl, which group is unsubstituted or substituted by from one to five $R_{24}$ substituents;
Het$^d$ represents a 4- to 14-membered heterocyclic group containing one or more heteroatoms selected from O, S and N, which heterocyclic group may comprise one, two or three rings;
each $R_{23}$ and $R_{24}$ independently represents halo, branched or unbranched $C_{1-6}$ alkyl, branched or unbranched $C_{2-6}$ alkenyl, branched or unbranched $C_{2-6}$ alkynyl; $C_{3-6}$ cycloalkyl, aryl (which latter five groups are unsubstituted or substituted by one or more halogen atoms) or $OR_{25}$;
$R_{25}$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl or aryl (which latter five groups are unsubstituted or substituted by one or more halogen atoms).°

As mentioned above, also encompassed by the complexes of formulae I and III are any solvates thereof. Preferred solvates are solvates formed by the incorporation into the solid state structure (e.g. crystal structure) of the compounds of the invention of molecules of a acceptable solvent (referred to below as the solvating solvent). Examples of such solvents include water, alcohols (such as methanol, ethanol, isopropanol and butanol), nitriles (such as acetonitrile, propionitrile, and butyronitrile), esters (such as ethyl acetate), ketones (such as acetone and ethyl methyl ketone), and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well-known and standard techniques such as thermogravimetric analysis (TGA), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Complexes of formula I, as well as solvates of such complexes are, for the sake of brevity, hereinafter referred to together as the "compounds of formula I". Complexes of formula III, as well as solvates of such compleses are, for the sake of brevity, hereinafter referred to together as the "compounds of formula III".

Compounds of formula I and formula III (as well as the compounds of formula II and IV as described hereinbelow) may contain double bonds and may thus exist as E (entgegen) and Z (zusammen) geometric isomers about each individual double bond. All such isomers and mixtures thereof are included within the scope of the invention.

Compounds of formula I and formula III (as well as the compounds of formula II and IV as described hereinbelow) may exist as regioisomers and may also exhibit tautomerism. All tautomeric forms and mixtures thereof are included within the scope of the invention.

Compounds of formula I and formula III may contain one or more asymmetric carbon atoms and may therefore exhibit optical and/or diastereoisomerism. Diastereoisomers may be separated using conventional techniques, e.g. chromatography or fractional crystallisation.

The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise stated, the term "alkyl" refers to an acyclic unbranched or branched, or cyclic, hydrocarbyl radical, which may be substituted or unsubstituted (with, for example, one or more halo atoms). Unless otherwise stated, where the term "alkyl" refers to an acyclic group, it is preferably $C_{1-6}$ alkyl (such as ethyl, propyl (e.g. n-propyl or isopropyl), butyl (e.g. branched or unbranched butyl), pentyl or, more preferably, methyl). Unless otherwise stated, where the term "alkyl" is a cyclic group (which may be where the group "cycloalkyl" is specified), it is preferably $C_{3-6}$ cycloalkyl.

Unless otherwise stated, the term "alkenyl" refers to an acyclic unbranched or branched, or cyclic, hydrocarbyl radical containing one or more carbon to carbon double bonds, and which radical may be substituted or unsubstituted (with, for example, one or more halo atoms). Unless otherwise stated, where the term "alkenyl" refers to an acyclic group, it is preferably $C_{2-6}$ alkenyl (such as ethylenyl, propylenyl (e.g. n-propylenyl or isopropylenyl), butylenyl (e.g. branched or unbranched butylenyl), or pentylenyl). Unless otherwise stated, where the term "alkenyl" is a cyclic group (which may be where the group "cycloalkenyl" is specified), it is preferably $C_{4-6}$ cycloalkenyl.

Unless otherwise stated, the term "alkynyl" refers to an acyclic unbranched or branched hydrocarbyl radical containing one or more carbon to carbon triple bonds and may also contain one or more carbon to carbon double bonds, and which radical may be substituted or unsubstituted (with, for example, one or more halo atoms). Unless otherwise stated, where the term "alkynyl" is used herein, it is preferably $C_{2-6}$ alkynyl (such as ethylynyl, propylynyl, butylynyl, or pentylynyl).

The term "halogen", when used herein, includes fluorine, chlorine, bromine and iodine.

The term "aryl" when used herein includes $C_{6-14}$ (such as $C_{6-13}$ (e.g. $C_{6-10}$)) aryl groups, which may be substituted or unsubstituted. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. The most preferred aryl groups include phenyl.

Heterocyclic ($Het^a$ and $Het^d$) groups may be fully saturated, partly unsaturated, wholly aromatic or partly aromatic in character. Values of $Het^a$ and $Het^d$ groups that may be mentioned include acridinyl, 1-azabicyclo[2.2.2]octanyl, azetidinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[6]furanyl, 1,3-dihydrobenzo[c]furanyl, 1,3-dihydro-2,1-benzisoxazolyl, 2,3-dihydropyrrolo[2,3-b]pyridinyl, dioxanyl, furanyl, furazanyl, hexahydropyrimidinyl, hydantoinyl, imidazolyl, imidazo[1,2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiazolyl, isothiochromanyl, isoxazolidinyl, isoxazolyl, maleimido, morpholinyl, naphtho[1,2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, oxetanyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), tetrazolyl, thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like. Particular values of $Het^a$ and $Het^d$ that may be mentioned include the 4- to 10-membered heterocyclic groups from the list above. Further, values of $Het^a$ and $Het^d$ that may be mentioned include the 5- and 8-membered (e.g. 5- to 6-membered) heterocyclic groups from the list above.

Substituents on heterocyclic ($Het^a$ to $Het^f$ ($Het^b$ and $Het^c$ are found in the compounds of formula II below, while $Het^e$ and $Het^f$ are found in the compounds of formula IV below)) groups may, where appropriate, be located on any atom in the ring system including a heteroatom. The point of attachment of heterocyclic groups may be via any atom in the ring system including (where appropriate) a heteroatom (such as a nitrogen atom), or an atom on any fused carbocyclic ring that may be present as part of the ring system. Heterocyclic groups may also be in the N- or S-oxidised form.

For the avoidance of doubt, in cases in which the identity of two or more substituents in a compound of formula I may be the same, the actual identities of the respective substituents are not in any way interdependent. For example, given that the compound of formula I has more than four $R_2$ groups, those $R_2$ groups may be the same or different. Similarly, in the situation in which $R_4$ and $R_5$ are both $C_2$ alkyl groups substituted by one or more $C_{1-4}$ alkyl groups, the alkyl groups in question may be the same or different.

All individual features (e.g. preferred or particular features) mentioned herein may be taken in isolation or in combination with any other feature (including preferred or particular features) mentioned herein (hence, preferred or particular features may be taken in conjunction with other preferred or particular features, or independently of them).

Embodiments of the invention that may be mentioned include those that relate to compounds of formula I in which:
(a) each $R_1$ independently represents $C_{1-3}$alkyl-phenyl, which phenyl group is substituted by from two to four $R_3$ substituents;
each $R_2$ independently represents phenyl, which group is unsubstituted or substituted by from one to two $R_4$ substituents;
each $R_3$ and $R_4$ independently represents fluoro, branched or unbranched $C_{1-6}$ alkyl, $C_{3-6}$ cycloalkyl, which latter two groups are unsubstituted or substituted by one or more halogen atoms) or $OR_5$;
$R_5$ represents branched or unbranched $C_{1-3}$ alkyl or $C_{3-6}$ cycloalkyl, which groups are unsubstituted or substituted by one or more halogen atoms;
(b) each $R_1$ independently represents $CH_2$-phenyl, which phenyl group is substituted by from two to three $R_3$ substituents;
each $R_2$ independently represents unsubstituted phenyl;
each $R_3$ independently represents fluoro, branched or unbranched $C_{3-5}$ alkyl, which latter group is unsubstituted or $OR_5$;
$R_5$ represents branched or unbranched $C_{1-3}$ alkyl, which group is unsubstituted or substituted by one or more halogen atoms;
(c) the organic cation (A) may be enantioenriched.

Embodiments of the invention that may be mentioned include those that relate to compounds of formula III in which:
(a) each $R_{21}$ independently represents $C_{1-3}$ alkyl-phenyl, which phenyl group is substituted by from two to four $R_{23}$ substituents;
each $R_{22}$ independently represents phenyl, which group is unsubstituted or substituted by from one to two $R_{24}$ substituents;

each $R_{23}$ and $R_{24}$ independently represents fluoro, branched or unbranched $C_{1-6}$ alkyl, $C_{3-6}$ cycloalkyl, which latter two groups are unsubstituted or substituted by one or more halogen atoms) or $OR_{25}$;
$R_{25}$ represents branched or unbranched $C_{1-3}$ alkyl or $C_{3-6}$ cycloalkyl, which groups are unsubstituted or substituted by one or more halogen atoms;
(b) each $R_{21}$ independently represents $CH_2$-phenyl, which phenyl group is substituted by from two to three $R_{23}$ substituents;
each $R_{22}$ independently represents unsubstituted phenyl;
each $R_{23}$ independently represents fluoro, branched or unbranched $C_{3-5}$ alkyl, which latter group is unsubstituted or $OR_{25}$;
$R_{25}$ represents branched or unbranched $C_{1-3}$ alkyl, which group is unsubstituted or substituted by one or more halogen atoms;
(c) the organic cation (C) may be enantioenriched.

Embodiments of the invention that may be mentioned include those that relate to compounds of formula I in which the organic cation (A) or compounds of formula III in which the organic cation (C) may be selected from:
(i) 1,4-bis((4S,5S)-1,3-bis(3,5-di-tert-butylbenzyl)-4,5-diphenylimidazolidin-2-ylidene)piperazine-1,4-diium;
(ii) 1,4-bis((4R,5R)-1,3-bis(3,5-di-tert-butylbenzyl)-4,5-diphenylimidazolidin-2-ylidene)piperazine-1,4-diium;
(iii) 1,4-bis((4S,5S)-1,3-bis(3,5-di-tert-butyl-4-methoxybenzyl)-4,5-diphenylimidazolidin-2-ylidene)piperazine-1,4-diium;
(iv) 1,4-bis((4R,5R)-1,3-bis(3,5-di-tert-butyl-4-methoxybenzyl)-4,5-diphenylimidazolidin-2-ylidene)piperazine-1,4-diium;
(v) 1,4-bis((4S,5S)-1,3-bis(3,5-di-tert-butyl-4-fluorobenzyl)-4,5-diphenylimidazolidin-2-ylidene)piperazine-1,4-diium; and
(vi) 1,4-bis((4R,5R)-1,3-bis(3,5-di-tert-butyl-4-fluorobenzyl)-4,5-diphenylimidazolidin-2-ylidene)piperazine-1,4-diium.

For example, the organic cation (A)/(C) may be selected from:
(i) 1,4-bis((4S,5S)-1,3-bis(3,5-di-tert-butylbenzyl)-4,5-diphenylimidazolidin-2-ylidene)piperazine-1,4-diium; and
(ii) 1,4-bis((4R,5R)-1,3-bis(3,5-di-tert-butylbenzyl)-4,5-diphenylimidazolidin-2-ylidene)piperazine-1,4-diium.

As mentioned above, the compounds of formula I are useful in catalysing the sulfoxidation of sulfides. As such, there is provided a process of manufacturing a sulfoxide, comprising reacting a compound of formula (II):

(II)

in the presence of a complex of formula (I), as defined hereinbefore, wherein in the compound of formula (II):
$R_6$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl (which latter three groups are unsubstituted or substituted by one or more substituents selected from halo, $OR_8$, and $C(O)R_9$), $C(O)R_{10}$, $C(O)OR_{11}$ or $OR_{12}$;
$R_7$ represents $CH(R_{13})(R_{14})$, $Het^b$ or aryl, which latter two groups are unsubstituted or substituted by one or more substituents selected from halo, $NO_2$, CN, branched or unbranched $C_{1-6}$ alkyl (optionally substituted by one or more halo atoms), $C(O)R_5$ or $OR_{16}$;

$R_{13}$ and $R_{14}$ each independently represent H, aryl or Het$^c$ (which latter two groups are unsubstituted or substituted by one or more substituents selected from halo, branched or unbranched $C_{1-6}$ alkyl, $C(O)R_{17}$ and $OR_{18}$), provided that at least one of $R_{13}$ and $R_{14}$ is not H;

$R_8$, $R_{12}$, $R_{16}$ and $R_{18}$ each independently represent H, $C(O)R_{19}$ or a branched or unbranched $C_{1-6}$ alkyl optionally substituted by one or more halo atoms;

$R_9$, $R_{10}$, $R_{15}$ and $R_{17}$ each independently represent a branched or unbranched $C_{1-6}$ alkyl (optionally substituted by one or more halo atoms), $OR_{20}$ or $N(R_{20'})(R_{20''})$;

$R_{11}$ represents a branched or unbranched $C_{1-6}$ alkyl (optionally substituted by one or more halo atoms);

$R_{19}$, $R_{20}$, $R_{20'}$ and $R_{20''}$ each independently represent H or a branched or unbranched $C_{1-6}$ alkyl (optionally substituted by one or more halo atoms);

Het$^b$ and Het$^c$ represents a 4- to 14-membered heteroaromatic group containing one or more heteroatoms selected from O, S and N, which heteroaromatic group may comprise one, two or three rings; and n represents from 1 to 10.

The terms "alkyl", "alkenyl", "alkynyl", "aryl", and "cycloalkyl" are as defined hereinbefore.

Heterocyclic (Het$^b$ and Het$^c$) groups are wholly aromatic or partly aromatic in character and may be selected from the wholly aromatic or partly aromatic heterocyclic (e.g. wholly aromatic) groups mentioned hereinabove with respect to Het$^a$ and Het$^d$ groups. Particular values of Het$^b$ and Het$^c$ that may be mentioned include the 4- to 10-membered wholly aromatic or partly aromatic heterocyclic (e.g. wholly aromatic) groups mentioned in the list mentioned hereinabove with respect to Het$^a$ and Het$^d$. Further, values of Het$^b$ and Het$^c$ that may be mentioned include the 5- and 8-membered (e.g. 5- to 6-membered) wholly aromatic or partly aromatic heterocyclic (e.g. wholly aromatic) groups mentioned in the list mentioned hereinabove with respect to Het$^a$ and Het$^d$.

In embodiments of the current invention, the compound of formula (II) may be one in which:
(a) $R_6$ represents branched or unbranched $C_{1-4}$ alkyl, branched or unbranched $C_{2-4}$ alkenyl (which groups are unsubstituted or substituted by one or more substituents selected from halo, and $C(O)R_9$), $C(O)R_{10}$, or $C(O)OR_{11}$;

$R_9$ and $R_{10}$ each independently represent a branched or unbranched $C_{1-4}$ alkyl (optionally substituted by one or more halo atoms) or $OR_{20}$;

$R_{11}$ represents a branched or unbranched $C_{1-4}$ alkyl (optionally substituted by one or more halo atoms)

(e.g. $R_6$ represents branched or unbranched branched or unbranched $C_{2-4}$ alkenyl (which groups are unsubstituted or substituted by one or more substituents selected from $C(O)OR_{20}$), or $C(O)OR_{11}$;

$R_{11}$ and $R_{20}$ each independently represent a branched or unbranched $C_{1-4}$ alkyl (e.g. Me, Et, or $^t$Bu); and n represents from 1 to 5);

(b) $R_7$ represents $CH(R_{13})(R_{14})$, phenyl or napthyl, which latter two groups are unsubstituted or substituted by one or more substituents selected from halo, branched or unbranched $C_{1-6}$ alkyl (optionally substituted by one or more halo atoms), $C(O)R_{15}$ or $OR_{16}$;

$R_{13}$ and $R_{14}$ each independently represent H, phenyl or naphtyl (which latter two groups are unsubstituted or substituted by one or more substituents selected from halo, branched or unbranched $C_{1-3}$ alkyl, $C(O)R_{17}$ and $OR_{18}$), provided that at least one of $R_{13}$ and $R_{14}$ is not H.

In the process described herein using the compounds of formula I as a catalyst, the process may provide an enantiomerically enriched sulfoxide as the product where the compound of formula (I) comprises an enantioenriched organic cation (A)

As noted hereinbefore, the complex of formula (I) may be used in a catalytic amount or a stoichiometric amount. When used in a catalytic amount, the compound of formula (I) is used in combination with at least one molar equivalent, relative to the compound of formula (II), of an oxidising agent. A suitable oxidising agent may be a peroxide, such as an organic peroxide or, more particularly, hydrogen peroxide.

In embodiments of the invention where the complex of formula (I) is used in a catalytic amount in the process of oxidising compounds of formula (II), a suitable catalytic amount may be from 1 to 10 mol % relative to the molar amount of the compound of formula (II) (e.g. 1 mol %).

It will be appreciated that the process described hereinbefore may be conducted in a suitable solvent. Solvents that may be mentioned herein include, but are not limited to toluene, xylene or, more particularly, an ether solvent (e.g. diethyl ether, diisopropyl ether or di-n-butyl ether). The process may be run at any suitable temperature up to the boiling point of the solvent (or solvents) used in the process. For example, the process may be conducted at a temperature of from −75° C. to 100° C., such as from −10° C. to 30° C. (e.g. from 0° C. to 25° C.). It will be appreciated that when the desired product of the process is a sulfoxide that is enantioenriched, the process may be run at a temperature in the range of from −10° C. to 30° C., such as from 0° C. to 25° C.

While the complex of formula I may be pre-prepared, it is also possible to generate the complex in situ. Thus in certain embodiments that may be mentioned herein, the process may provide the complex of formula (I) in situ through reaction of an organic cation (A) with a molybdenum-containing salt and a sulfur-containing additive where:
the organic cation (A) is provided as a salt with a counterion selected from chloride;
the molybdenum-containing salt is $M_2MoO_4$ or $(NH_4)_6Mo_7O_{24}$ or solvates thereof, where M represents Na, K or Li; and
the sulfur-containing additive is selected from one or more of the group consisting of $NaHSO_4$, $KHSO_4$, $H_2SO_4$, and $TBAHSO_4$.

For example:
(i) the organic cation salt may be provided in an amount of from 1 to 10 mol % relative to the molar amount of the compound of formula (II) (e.g. 1 mol %); and/or
(ii) the molybdenum-containing salt may be present in an amount of from 1 mol % to 20 mol % relative to the molar amount of the compound of formula (II) (e.g. from 2 mol % to 5 mol %, such as 2.5 mol %); and/or
(iii) the sulfur-containing additive may be present in an amount of from 5 mol % to 100 mol % relative to the molar amount of the compound of formula (II) (e.g. from 10 mol % to 55 mol %, such as from 25 mol % to 50 mol %).

As mentioned above, the compounds of formula III are useful in catalysing the sulfoxidation of sulfides. As such, there is provided a process of manufacturing a sulfoxide, comprising reacting a compound of formula (IV):

(IV)

in the presence of a catalytic amount of a complex of formula (III), as defined in hereinbefore, and at least one molar equivalent of an oxidising agent relative to the compound of formula (IV), wherein in the compound of formula (IV):

$R_{26}$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl, aryl, $Het^e$ (which latter five groups are unsubstituted or substituted by one or more substituents selected from halo, $NO_2$, CN, $C_{1-6}$ alkyl (optionally substituted by one or more halo atoms), and $OR_{28}$), $OR_{29}$, CN, or $C(O)OR_{30}$;

$R_{27}$ represents $Het^f$ or aryl, which groups are unsubstituted or substituted by one or more substituents selected from halo, $NO_2$, CN, branched or unbranched $C_{1-6}$ alkyl (optionally substituted by one or more halo atoms), or $OR_{31}$;

$R_{28}$, $R_{29}$ and $R_{31}$ each independently represent H, C(O)$R_{32}$ or a branched or unbranched $C_{1-6}$ alkyl optionally substituted by one or more halo atoms;

$R_{30}$ and $R_{32}$ each independently represent H or a branched or unbranched $C_{1-6}$ alkyl optionally substituted by one or more halo atoms;

each $Het^e$ independently represents a 4- to 14-membered heterocyclic group containing one or more heteroatoms selected from O, S and N, which heterocyclic group may comprise one, two or three rings; and $Het^f$ represents a 4- to 14-membered heteroaromatic group containing one or more heteroatoms selected from O, S and N, which heteroaromatic group may comprise one, two or three rings; and n represents from 1 to 10.

Heterocyclic ($Het^e$ and $Het^f$) groups are wholly aromatic or partly aromatic in character and may be selected from the wholly aromatic or partly aromatic heterocyclic (e.g. wholly aromatic) groups mentioned hereinabove with respect to $Het^a$ and $Het^d$ groups. Particular values of $Het^e$ and $Het^f$ that may be mentioned include the 4- to 10-membered wholly aromatic or partly aromatic heterocyclic (e.g. wholly aromatic) groups mentioned in the list mentioned hereinabove with respect to $Het^a$ and $Het^d$. Further, values of $Het^e$ and $Het^f$ that may be mentioned include the 5- and 8-membered (e.g. 5- to 6-membered) wholly aromatic or partly aromatic heterocyclic (e.g. wholly aromatic) groups mentioned in the list mentioned hereinabove with respect to $Het^a$ and $Het^d$.

In embodiments of the current invention, the compound of formula (IV) may be one in which:

(a) $R_{26}$ represents H, phenyl, naphthyl, $Het^e$ (which latter three groups are unsubstituted or substituted by one or more substituents selected from halo, $NO_2$, $C_{1-4}$ alkyl (optionally substituted by one or more halo atoms), and $OR_{28}$), CN, or $C(O)OR_{30}$;

each $R_{28}$ independently represents H, or a branched or unbranched $C_{1-4}$ alkyl optionally substituted by one or more halo atoms; and each $R_{30}$ independently represents a branched or unbranched $C_{1-4}$ alkyl (e.g. Me, Et, $^tBu$); and n represents from 1 to 6

(e.g. $R_{26}$ represents H, phenyl, naphthyl (which latter two groups are unsubstituted or substituted by one or more substituents selected from halo, $NO_2$, $C_{1-4}$ alkyl (optionally substituted by one or more halo atoms), and $OR_{28}$), dioxolanyl, CN, or $C(O)OR_{30}$; and each $R_{28}$ independently represents a branched or unbranched $C_{1-4}$ alkyl optionally substituted by one or more halo atoms (e.g. $CH_3$, $CH_2CF_3$); and n represents from 1 to 5);

(b) $R_{27}$ represents $Het^f$, phenyl or naphthyl, which groups are unsubstituted or substituted by one or more substituents selected from F and $C_{1-4}$ alkyl (optionally substituted by one or more halo atoms);

$Het^f$ independently represents a 5- to 10-membered heteroaromatic group containing one or more heteroatoms selected from S and N, which heteroaromatic group may comprise one or two rings (e.g. $Het^f$ represents, thiazolyl, pyrrolyl, imidazolyl, thiazolyl, pyridyl, benzimidazolyl, benzathiazolyl, or indolyl).

In the process described herein the process may provide an enantiomerically enriched sulfoxide as the product, where the compound of formula (III) comprises an enantioenriched organic cation (C)

In certain embodiments that may be mentioned herein, the process may provide the complex of formula (III) in situ through reaction of an organic cation (C) with $M_2WO_4$ and $NaH_2PO_4$, where:

the organic cation (C) is provided as a salt with a counterion selected from chloride; and
M represents Na, K, $NH_4$ or Ag (e.g. Ag).

For example:

(i) the organic cation salt may be provided in an amount of from 1 to 10 mol % relative to the molar amount of the compound of formula (IV) (e.g. 2 mol %); and/or (ii) $M_2WO_4$ may be present in an amount of from 1 mol % to 20 mol % relative to the molar amount of the compound of formula (IV) (e.g. from 2 mol % to 5 mol %, such as 2 mol %); and/or (iii) $NaH_2PO_4$ may be present in an amount of from 4 mol % to 50 mol % relative to the molar amount of the compound of formula (IV) (e.g. from 5 mol % to 15 mol %, such as 10 mol %);

(iv) the molar ratio of $NaH_2PO_4$ to $M_2WO_4$ is from 2:1 to 10:1, such as 5:1.

As noted hereinbefore, the complex of formula (III) may be used in a catalytic amount and so is used in combination with at least one molar equivalent, relative to the compound of formula (IV), of an oxidising agent. A suitable oxidising agent may be a peroxide, such as an organic peroxide or, more particularly, hydrogen peroxide.

In embodiments of the invention where the complex of formula (III) is used in a catalytic amount in the process of oxidising compounds of formula (IV), a suitable catalytic amount may be from 1 to 10 mol % relative to the molar amount of the compound of formula (IV) (e.g. 1 mol %).

It will be appreciated that the process described hereinbefore may be conducted in a suitable solvent. Solvents that may be mentioned herein include, but are not limited to an ether solvent (e.g. diethyl ether, diisopropyl ether or di-n-butyl ether, such as diethyl ether or, more particularly, diisopropyl ether). The process may be run at any suitable temperature up to the boiling point of the solvent (or solvents) used in the process. For example, the process may be conducted at a temperature of from −75° C. to 100° C., such as from −10° C. to 10° C. (e.g. from 0° C. to 5° C.). It will be appreciated that when the desired product of the process is a sulfoxide that is enentioenriched, the process may be run at a temperature in the range of from −10° C. to 10° C., such as from 0° C. to 5° C.

Compounds of formula I to IV may be prepared in accordance with techniques that are well known to those skilled in the art, for example as described hereinafter in the examples section.

Substituents, such as R² in final compounds of formula I (or precursors thereto and other relevant intermediates) may be modified one or more times, after or during the processes described hereinafter by way of methods that are well known to those skilled in the art. Examples of such methods include substitutions, reductions (e.g. carbonyl bond reductions in the presence of suitable and, if necessary, chemoselective, reducing agents such as $LiBH_4$ or $NaBH_4$), oxidations, alkylations, acylations, hydrolyses, esterifications, and etherifications. The precursor groups can be changed to a different such group, or to the groups defined in formula I, at any time during the reaction sequence.

Compounds of the invention may be isolated from their reaction mixtures using conventional techniques (e.g. recrystallisation, column chromatography, preparative HPLC, etc.).

In the processes described hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described hereinafter may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3rd edition, T. W. Greene & P. G. M. Wutz, Wiley-Interscience (1999).

As used herein, the term "functional groups" means, in the case of unprotected functional groups, hydroxy-, thiolo-, amino function, carboxylic acid and, in the case of protected functional groups, lower alkoxy, N-, O-, S-acetyl, carboxylic acid ester.

Non-limiting examples that embody certain aspects of the invention will now be described.

EXPERIMENTAL

General

¹H and ¹³C NMR spectra were recorded on Bruker Avance III 400 (400 MHz) (100 MHz) spectrometer. Chemical shifts are recorded as δ in units of parts per million (ppm). The residual solvent peak was used as an internal reference. ³¹P NMR was performed on a Bruker Avance III 400 (400 MHz) spectrometer. ¹⁹F NMR was performed on a Bruker Avance III 400 (400 MHz) spectrometer. ⁹⁵Mo NMR was performed on a Bruker Avance III 400 (26.7 MHz) spectrometer and chemical shifts are reported relative to an external reference 2 M $Na_2MoO_4 \cdot 2H_2O$ solution in $D_2O$, assigned to 0 ppm.

High resolution mass spectra (HRMS) were obtained on the Q-Tof Premier mass spectrometer (Waters Corporation) and reported in units of mass to charge ratio (m/z).

Enantiomeric excess values were determined by chiral HPLC analysis on Shimadzu LC-20AT and LC-2010CHT HPLC workstations. Optical rotations were measured in ethyl acetate using a 1 mL cell with a 1 dm path length on a Jasco P-1030 polarimeter with a sodium lamp of wavelength 589 nm and reported as follows: [α]Drt (c=g/100 mL, solvent).

Two-dimensional (2D) Raman spectral images were obtained by scanning the line-shaped laser focus in a single direction with a two-dimensional image sensor (Princeton Instrument, PIXIS 400 BR, −70° C., 1340×400 pixels).

X-ray crystallography analysis was performed on Bruker X8 APEX X-ray diffraction meter.

Flash chromatography separations were performed on Merck 60 (0.040-0.063 mm) mesh silica gel.

Analytical thin-layer chromatography (TLC) was performed on Merck 60 F254 silica gel plates. Visualization was performed using a UV lamp or potassium permanganate stain.

IR was recorded on neat compounds or in dispersed KBr pellets using a Shimadzu IR Prestige21 FTIR spectrometer; only strong and selected absorbances ($\nu_{max}$) are reported.

Melting point was recorded on OptiMelt (MPA100) melting point apparatus.

Materials

Toluene, Acetonitrile and Dichloromethane were distilled over $CaH_2$ under $N_2$ atmosphere. Unless otherwise stated, all reagents were purchased from the commercial suppliers Sigma-Aldrich or TCI. All racemates were prepared using a stoichiometric amount of mCPBA (meta-chloroperoxybenzoic acid) in DCM by analogy to the procedures referenced in M. Michel, *Tetrahedron*, 1986, 42, 5464 and/or the general procedure for sulfoxidation set out in and B. Kohl et al., *J. Med. Chem.*, 1992, 35, 1054.

THF was distilled over sodium/benzophenone under $N_2$ atmosphere. The mercaptans were purchased from commercial suppliers and used directly without further purification. Other reagents and solvents were commercial grade and were used as supplied without further purification, unless otherwise stated. Experiments involving moisture and/or air sensitive components were performed under a positive pressure of nitrogen in oven-dried glassware equipped with a rubber septum inlet.

Preparation of Catalysts and Substrates

Preparation and Characterization of Chiral Bisguanidinium

The preparation of catalyst BG-1 (also referred to as (S,S)-1a herein) is provided below as a representative example. Chiral bisguanidiniums BG2-5 and (R,R)-1b were prepared by analogy.

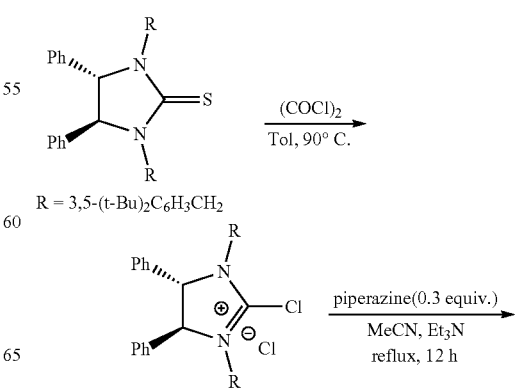

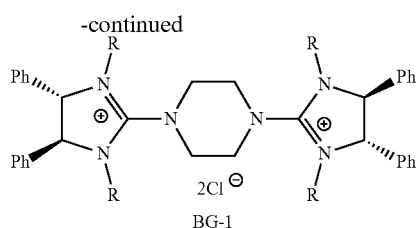

BG-1

1,4-bis((4S,5S)-1,3-bis(3,5-di-tert-butylbenzyl)-4,5-diphenylimidazolidin-2-ylidene)piperazine-1,4-diium chloride (BG-1)

(4S,5S)-1,3-bis(3,5-di-tert-butylbenzyl)-4,5-diphenylimidazolidine-2-thione was prepared in accordance with literature procedure (see Zong, L.; Ban, X.; Kee, C. W.; Tan, C. H. *Angewandte. Chemie.* 2014, 126, 12043). A 25 mL round-bottomed flask was charged with a solution of (4S, 5S)-1,3-bis(3,5-di-tert-butylbenzyl)-4,5-diphenylimidazolidine-2-thione (1.59 g, 2.41 mmol, 1.0 equiv) in toluene (8 mL) with a condenser under $N_2$ atmosphere. $(COCl)_2$ (1.66 mL, 19.3 mmol, 8.0 equiv) was added via syringe in one portion. The mixture was heated to 90° C. for about 12 h, and then refluxed for 1 h. Toluene was removed under reduced pressure and solid imidazoline salt was obtained directly for the next step without any purification. The imidazoline salt was dissolved in dry MeCN (2 mL) under nitrogen atmosphere, and then piperazine (62 mg, 0.72 mmol, 0.3 equiv) was added, followed by the addition of $Et_3N$ (1 mL, 7.23 mmol, 3.0 equiv). Then the whole solution was heated to reflux for 12 h and cooled to rt. 1M HCl (20 mL) was added to the reaction solution and the mixture was then extracted by $CH_2Cl_2$ (20 mL×3), and the organic layers were combined and dried over anhydrous $Na_2SO_4$. Solvent was removed under reduced pressure and bis-guanidinium salt BG-1 was obtained by flash chromatography (silica gel, DCM-Methanol 100:1-30:1), as a beige powder.

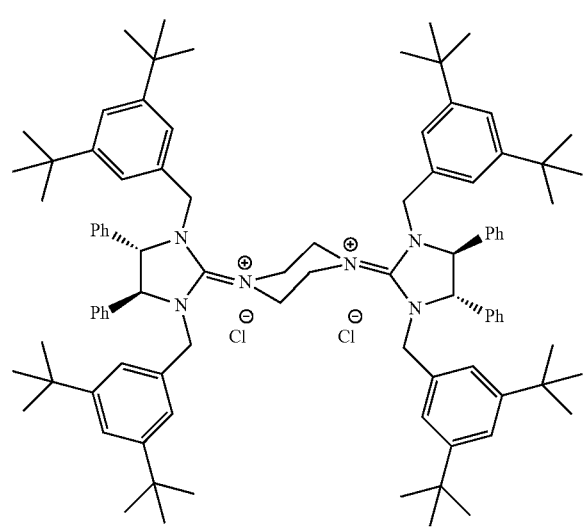 [SMILES: CC(C)(C)c1cc(CN2C(=[N+]3CC[N+](=C4N(Cc5cc(C(C)(C)C)cc(C(C)(C)C)c5)[C@@H](c5ccccc5)[C@H](c5ccccc5)N4Cc4cc(C(C)(C)C)cc(C(C)(C)C)c4)CC3)N(Cc3cc(C(C)(C)C)cc(C(C)(C)C)c3)[C@@H](c3ccccc3)[C@@H]2c2ccccc2)cc(C(C)(C)C)c1 ; [Cl-] ; [Cl-]]

1,4-bis((4S,5S)-1,3-bis(3,5-di-tert-butylbenzyl)-4,5-diphenylimidazolidin-2-ylidene)piperazine-1,4-diium chloride (BG-1 or (S,S)-1a)

beige powder; 80% yield; mp: 209.3-211.5° C.; $[a]_D^{22}$=−33.9 (c 1.07, CHCl$_3$); $^1$H NMR (400 MHz, CDCl$_3$) δ 7.30 (dd, J=5.0, 1.5 Hz, 12H), 7.20 (s, 4H), 7.05 (dd, J=6.5, 2.8 Hz, 8H), 6.96 (d, J=1.5 Hz, 8H), 5.19 (d, J=14.7 Hz, 4H), 4.82 (d, J=14.7 Hz, 4H), 4.73 (d, J=9.5 Hz, 4H), 4.48 (d, J=9.5 Hz, 4H), 4.32 (s, 1H), 1.14 (s, 72H); $^{13}$C NMR (100 MHz, CDCl$_3$) δ 162.68, 151.30, 137.67, 131.89, 129.58, 129.16, 126.51, 123.37, 122.26, 70.39, 54.52, 48.99, 34.69, 31.37, 31.28; IR: 2962.66, 1597.06, 1527.62, 1454.33, 1361.74, 1018.41, 910.40, 740.64, 702.09 cm$^{-1}$; HRMS (ESI) calcd for $C_{94}H_{124}Cl_2N_6$ m/z [M−2Cl$^-$]$^{2+}$: 668.4944; found: 668.4941.

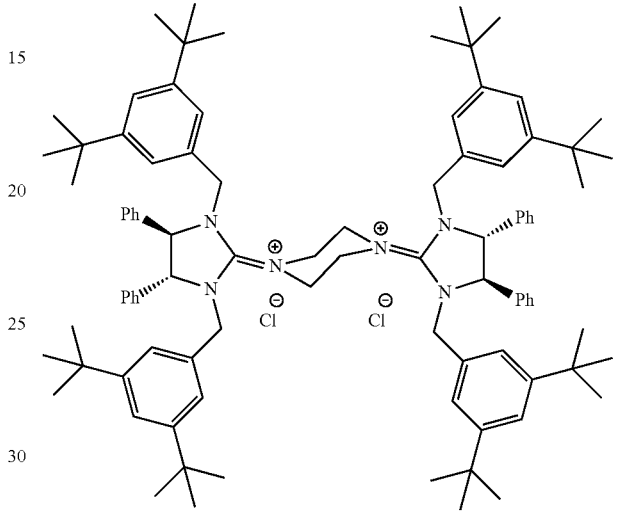

1,4-bis((4R,5R)-1,3-bis(3,5-di-tert-butylbenzyl)-4,5-diphenylimidazolidin-2-ylidene)piperazine-1,4-diium chloride ((R,R)-1b)

beige powder; 70% yield; mp: 209.6-212.2° C.; $[a]_D^{22}$=+31.9 (c 1.92, CHCl$_3$); $^1$H NMR (400 MHz, CDCl$_3$) δ 7.29 (dd, J=5.1, 1.6 Hz, 12H), 7.20 (s, 4H), 7.08-7.00 (m, 8H), 6.95 (d, J=1.6 Hz, 8H), 5.19 (d, J=14.6 Hz, 4H), 4.80 (d, J=14.7 Hz, 4H), 4.72 (d, J=9.6 Hz, 4H), 4.47 (d, J=9.5 Hz, 4H), 4.31 (s, 4H), 1.13 (s, 72H); $^{13}$C NMR (100 MHz, CDCl$_3$) δ 162.65, 151.27, 137.68, 131.89, 129.54, 129.12, 126.48, 123.37, 122.24, 70.32, 54.45, 48.98, 34.66, 31.25; IR: 2962.66, 1600.92, 1519.91, 1454.33, 1361.74, 1280.73, 1199.72, 1153.43, 1018.41, 910.4, 736.81, 702.09 cm$^{-1}$; HRMS (ESI) calcd for $C_{94}H_{124}Cl_2N_6$ m/z [M−2Cl$^-$]$^{2+}$: 668.4944; found: 668.4951.

Synthesis of Sulfide Substrates for Use in tungstate System

Synthesis of Heterocyclic Sulfides (2a-2u)

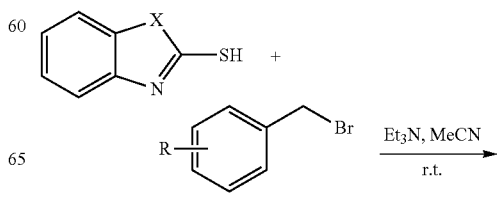

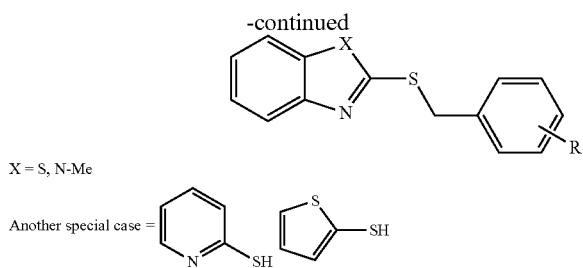

X = S, N-Me

Another special case =

Benzyl bromide (3.6 mmol) was added to a solution of heterocyclic thiol (3 mmol) and Et₃N (4.5 mmol) dropwise in MeCN (10 mL) at room temperature. The resulting reaction mixture was stirred for appropriate time (monitored by TLC). 6M HCl aqueous was used for quenching. Then the mixture was extracted by Ethyl acetate EtOAc (10 mL×3). The combined organic layer was washed by brine and dried by Na₂SO₄. After removing solvent under reduced pressure, the crude residue was directly loaded onto a short silica gel column, followed by gradient elution with Hexane/EtOAc mixture (50/1-30/1 ratio). Removing the solvent in vacuo, afforded the desired products.

Phenyl sulfides (5a-5d) were prepared by analogy.

Synthesis of Heterocyclic Sulfide (3)

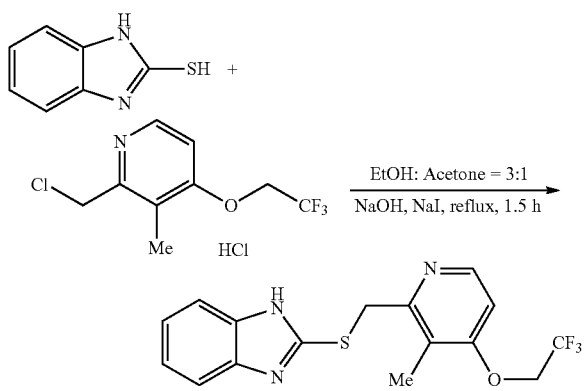

2-Mercaptobenzimidazole (1.0 mmol), 2-(Chloromethyl)-3-methyl-4-(2,2,2-trifluoroethoxy)pyridine hydrochloride (1.0 mmol), NaOH (2.0 mmol) and NaI (0.033 mmol) were added to a ethanol and acetone mixed solvent (v:v, 3:1). After refluxing for 1.5 hours, cool down to the room temperature. Filtrate the reaction mixture and dry the residues on rotary evaporators, then directly load the residues onto a short silica gel column, followed by gradient elution with Hexane/EtOAc mixture (30/1-15/1 ratio). Removing the solvent in vacuo, afforded the desired products.

Synthesis and Characterization of Sulfide Substrates for Use in Molybdate System Synthesis of methyl 2-(benzhydrylthio)acetate (7a)

(see Andrea Altieri et al. Sulfur-containing amide-based [2]rotaxanes and molecular shuttles. *Chem. Sci.* 2, 1922-1928 (2011)):

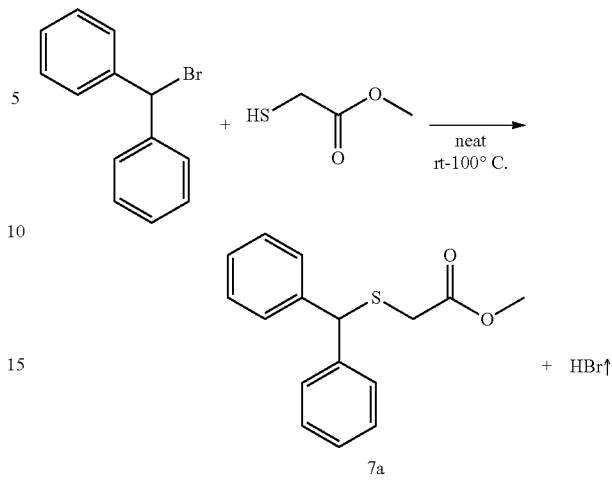

Methyl thioglycolate (447 µL, 5.0 mmol) was slowly added to bromodiphenyl methane (1.359 g, 5.5 mmol) at room temperature. After the initial reaction had subsided, the mixture was heated to 100° C. for 2 h until there was no further evolution of HBr which was trapped and neutralized by passing over an aqueous saturated NaHCO₃ solution. The reaction mixture was then allowed to cool to room temperature and poured into H₂O (10 mL) and extracted with EtOAc (25 mL×3). The combined organic layer was washed by brine and dried by Na₂SO₄, filtered and concentrated. The crude residue was subjected to purification by flash column chromatography (silica gel, hexane:EtOAc, gradient from 100:1 to 20:1) to afford the product as pale yellow oil, 1.238 g, 91% yield. ¹H NMR (400 MHz, CDCl₃) δ 7.48-7.40 (m, 4H), 7.33 (dt, J=7.7, 5.2 Hz, 4H), 7.28-7.19 (m, 2H), 5.40 (s, 1H), 3.68 (s, 3H), 3.10 (s, 2H); ¹³C NMR (100 MHz, CDCl₃) δ 170.71, 140.29, 128.61, 128.43, 127.45, 54.16, 52.29, 33.48; IR: 1732.08, 1597.06, 1492.90, 1450.47, 1276.88, 1195.87, 1130.29, 1006.84, 748.38, 702.09, 628.79, 586.36 cm⁻¹; HRMS (ESI) calcd for $C_{16}H_{16}O_2S$ m/z [M+H]⁺: 273.0949; found: 273.0946.

Synthesis of Aliphatic 2-thio Acetates (7b-7k). For example, synthesis of tert-butyl 2-(benzylthio)acetate (7b)

(see Qingping Zeng et al. Benzoheterocyclecarboxaldehyde derivatives as IRE-1a inhibitors and their preparation and use for the treatment of diseases. WO2011127070A2 (2011)):

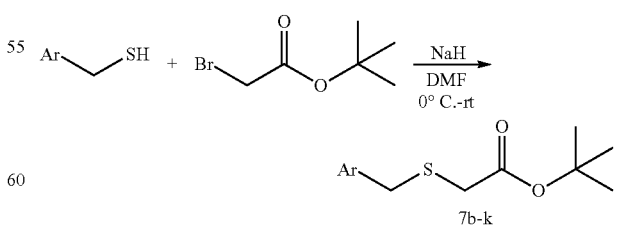

Benzyl mercaptan (mg, 5.0 mmol) was dissolved in dry DMF (25 mL) and the solution was cooled to 0° C. NaH (60% suspension in oil) (220 mg, 5.5 mmol, 1.1 equiv) was then added and the resulting solution was stirred for 30 min.

tert-butyl bromoacetate (812 μL, 5.5 mmol, 1.1 equiv) was then added and the solution was stirred at room temperature for appropriate time. The reaction was quenched by slow addition of H₂O and DMF solvent was removed by vacuum pump. The resulting residue was subjected to purification by flash column chromatography (silica gel, hexanes:EtOAc, 20:1) to afford the desired product with 80% to quantitative yield. Aliphatic 2-thio Acetates (7c-7k) are prepared by analogy.

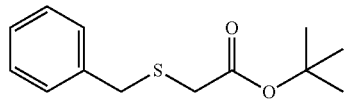 [SMILES: CC(C)(C)OC(=O)CSCc1ccccc1]

tert-butyl 2-(benzylthio)acetate (7b)

Colorless oil; ¹H NMR (400 MHz, CDCl₃) δ 7.37-7.29 (m, 4H), 7.28-7.21 (m, 1H), 3.83 (s, 2H), 2.98 (s, 2H), 1.49 (s, 9H); ¹³C NMR (100 MHz, CDCl₃) δ 169.53, 137.39, 129.09, 128.46, 127.12, 81.46, 36.07, 33.39, 27.97; IR: 1728.22, 1492.90, 1454.33, 1392.61, 1369.46, 1296.16, 1257.59, 1122.57, 948.98, 852.54, 763.81, 702.09 cm⁻¹; HRMS (ESI) calcd for C₁₃H₁₈O₂S m/z [M+H]⁺: 239.1106; found: 239.1103.

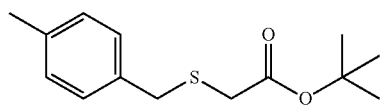 [SMILES: Cc1ccc(CSCC(=O)OC(C)(C)C)cc1]

tert-butyl 2-((4-methylbenzyl)thio)acetate (7c)

Colorless oil; ¹H NMR (400 MHz, CDCl₃) δ 7.22 (d, J=8.0 Hz, 2H), 7.13 (d, J=7.9 Hz, 2H), 3.80 (s, 2H), 2.98 (s, 2H), 2.34 (s, 3H), 1.49 (s, 9H); ¹³C NMR (100 MHz, CDCl₃) δ 169.63, 136.80, 134.29, 129.17, 129.01, 81.45, 35.82, 33.42, 28.00, 21.06; IR: 1728.22, 1512.19, 1454.33, 1392.61, 1369.46, 1296.16, 1257.59, 1122.57, 948.98, 817.82, 725.23 cm⁻¹; HRMS (ESI) calcd for C₁₄H₂₀O₂S m/z [M+H]⁺: 253.1262; found: 253.1256.

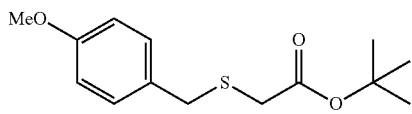 [SMILES: COc1ccc(CSCC(=O)OC(C)(C)C)cc1]

tert-butyl 2-((4-methoxybenzyl)thio)acetate (7d)

Colorless oil; ¹H NMR (400 MHz, CDCl₃) δ 7.27 (d, J=8.3 Hz, 2H), 6.87 (d, J=8.3 Hz, 2H), 3.81 (s, 3H), 3.80 (s, 2H), 2.99 (s, 2H), 1.51 (s, 9H); ¹³C NMR (100 MHz, CDCl₃) δ 169.63, 158.73, 130.21, 129.32, 113.88, 81.43, 55.22, 35.50, 33.33, 27.99; IR: 1728.22, 1716.65, 1612.49, 1585.49, 1512.19, 1458.18, 1369.46, 1300.02, 1249.87, 1172.72, 1122.57, 1033.85, 948.98, 833.25 cm⁻¹; HRMS (ESI) calcd for C₁₄H₂₀O₃S m/z [M+H]⁺: 269.1211; found: 269.1208.

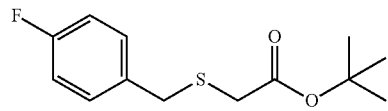 [SMILES: CC(C)(C)OC(=O)CSCc1ccc(F)cc1]

tert-butyl 2-((4-fluorobenzyl)thio)acetate (7e)

Colorless oil; ¹H NMR (400 MHz, CDCl₃) δ 7.36-7.27 (m, 2H), 7.06-6.96 (m, 2H), 3.80 (s, 2H), 2.96 (s, 2H), 1.48 (s, 9H); ¹³C NMR (100 MHz, CDCl₃) δ 169.47, 161.98 (d, J=245.6 Hz), 133.15 (d, J=3.2 Hz), 130.68 (d, J=8.1 Hz), 115.35 (d, J=21.5 Hz), 81.61, 35.34, 33.35, 28.00; ¹⁹F NMR (376 MHz, CDCl₃) δ −115.35; IR: 1728.22, 1600.92, 1508.33, 1392.61, 1369.46, 1296.16, 1222.57, 1122.57, 948.98, 837.11, 759.95, 732.95 cm⁻¹; HRMS (ESI) calcd for C₁₃H₁₇FO₂S m/z [M+H]⁺: 257.1012; found: 257.1010.

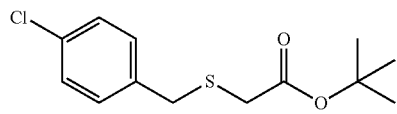 [SMILES: CC(C)(C)OC(=O)CSCc1ccc(Cl)cc1]

tert-butyl 2-((4-chlorobenzyl)thio)acetate (7f)

Colorless oil; ¹H NMR (400 MHz, CDCl₃) δ 7.32-7.22 (m, 4H), 3.78 (s, 2H), 2.95 (s, 2H), 1.48 (s, 9H); ¹³C NMR (100 MHz, CDCl₃) δ 169.39, 135.95, 132.97, 130.46, 128.63, 81.64, 35.37, 33.31, 27.98; IR: 1728.22, 1489.05, 1454.33, 1369.46, 1296.16, 1257.59, 1122.57, 1091.71, 1014.56, 948.98, 833.25 cm⁻¹; HRMS (ESI) calcd for C₁₃H₁₇ClO₂S m/z [M+H]⁺: 273.0716; found: 273.0710.

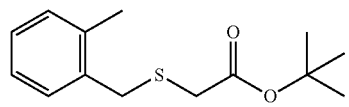 [SMILES: Cc1ccccc1CSCC(=O)OC(C)(C)C]

tert-butyl 2-((2-methylbenzyl)thio)acetate (7g)

Colorless oil; ¹H NMR (400 MHz, CDCl₃) δ 7.24 (d, J=6.6 Hz, 1H), 7.20-7.11 (m, 3H), 3.85 (s, 2H), 3.03 (s, 2H), 2.41 (s, 3H), 1.51 (s, 10H); 13C NMR (100 MHz, CDCl₃) δ 169.68, 136.85, 135.00, 130.69, 130.00, 127.48, 125.76, 81.49, 34.27, 33.90, 27.99, 19.07; IR: 1716.65, 1454.33, 1392.61, 1369.46, 1292.31, 1257.59, 1161.15, 1122.57, 948.98, 763.81, 732.95, 489.92 cm⁻¹; HRMS (ESI) calcd for C₁₄H₂₀O₂S m/z [M+H]⁺: 253.1262; found: 253.1270.

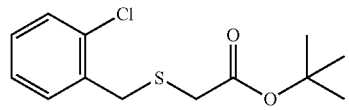 [SMILES: CC(C)(C)OC(=O)CSCc1ccccc1Cl]

tert-butyl 2-((2-chlorobenzyl)thio)acetate (7h)

Colorless oil; ¹H NMR (400 MHz, CDCl₃) δ 7.42-7.33 (m, 2H), 7.24-7.15 (m, 2H), 3.95 (s, 2H), 3.05 (s, 2H), 1.49

(s, 9H); $^{13}$C NMR (100 MHz, CDCl$_3$) δ 169.48, 135.21, 134.16, 131.04, 129.93, 128.62, 126.70, 81.66, 33.88, 33.75, 27.99; IR: 1728.22, 1473.62, 1446.61, 1392.61, 1369.46, 1296.16, 1257.59, 1161.15, 1130.29, 1037.70, 948.98, 763.81, 740.67 cm$^{-1}$; HRMS (ESI) calcd for C$_{13}$H$_{17}$ClO$_2$S m/z [M+H]$^+$: 273.0716; found: 273.0720.

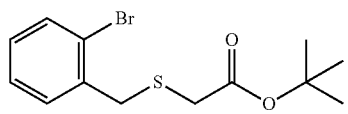 [SMILES: CC(C)(C)OC(=O)CSCc1ccccc1Br]

tert-butyl 2-((2-bromobenzyl)thio)acetate (7i)

Colorless oil; $^1$H NMR (400 MHz, CDCl$_3$) δ 7.57 (dd, J=8.0, 1.1 Hz, 1H), 7.39 (dd, J=7.6, 1.7 Hz, 1H), 7.27 (td, J=7.5, 1.2 Hz, 1H), 7.12 (td, J=7.7, 1.7 Hz, 1H), 3.96 (s, 2H), 3.05 (s, 2H), 1.49 (s, 9H); $^{13}$C NMR (100 MHz, CDCl$_3$) δ 169.51, 136.86, 133.29, 131.04, 128.84, 127.34, 124.61, 81.68, 36.46, 33.87, 28.01; IR: 1728.22, 1469.76, 1369.46, 1296.16, 1161.15, 1126.43, 1026.13, 948.98, 763.81, 736.81 cm$^{-1}$; HRMS (ESI) calcd for C$_{13}$H$_{17}$BrO$_2$S m/z [M+H]$^+$: 317.0211; found: 317.0202.

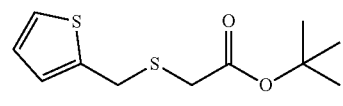

tert-butyl 2-((thiophen-2-ylmethyl)thio)acetate (7j)

Pale yellow oil; $^1$H NMR (400 MHz, CDCl$_3$) δ 7.22 (dd, J=5.1, 1.2 Hz, 1H), 6.97 (dd, J=3.4, 0.9 Hz, 1H), 6.92 (dd, J=5.1, 3.5 Hz, 1H), 4.06 (s, 2H), 3.06 (s, 2H), 1.49 (s, 10H); $^{13}$C NMR (100 MHz, CDCl$_3$) δ 169.36, 140.48, 126.89, 126.62, 125.19, 81.60, 33.41, 30.43, 27.98; IR: 1728.22, 1392.61, 1369.46, 1296.16, 1257.59, 1165.00, 1134.14, 948.98, 852.54, 702.09 cm$^{-1}$; HRMS (ESI) calcd for C$_{11}$H$_{16}$O$_2$S$_2$ m/z [M+H]$^+$: 245.0670; found: 245.0678.

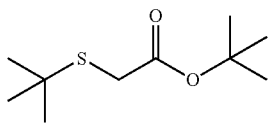

tert-butyl 2-(tert-butylthio)acetate (7k)

Colorless oil; $^1$H NMR (400 MHz, CDCl$_3$) δ 3.20 (s, 2H), 1.46 (s, 9H), 1.33 (s, 9H); $^{13}$C NMR (100 MHz, CDCl$_3$) δ 170.38, 81.34, 42.81, 32.71, 30.75, 27.91; IR: 1728.22, 1458.18, 1392.61, 1365.60, 1288.45, 1257.59, 1172.72, 1130.29, 952.84, 837.11, 763.81 cm$^{-1}$; HRMS (ESI) calcd for C$_{10}$H$_{20}$O$_2$S m/z [M+H]$^+$: 205.1262; found: 205.1259.

Synthesis of Aromatic 2-thio Acetates (9a-k)

For example, synthesis of tert-butyl 2-(phenylthio)acetate (9a) (see Katsukiyo Miura, Naoki Fujisawa, Hiroshi Saito, Di Wang & Akira Hosomi. Synthetic Utility of Stannyl Enolates as Radical Alkylating Agents1. *Org. Lett.* 3, 2591-2594 (2001)):

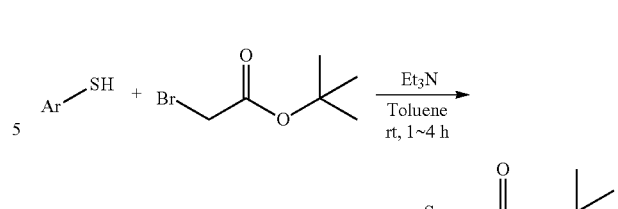

A mixture of thiophenol (511 μL, 5.0 mmol), Et$_3$N (697 μL, 5.0 mmol), tert-butyl bromoacetate (738 μL, 5.0 mmol), and toluene (5 mL) was stirred at room temperature for the appropriate time and monitored by TLC. After the addition of H$_2$O, the mixture was extracted with EtOAc. The combined organic layer was washed by brine and dried by Na$_2$SO$_4$, filtered and concentrated. The crude residue was subjected to purification by flash column chromatography (silica gel, hexanes:EtOAc, 20:1) to afford the desired product with 90% to quantitative yield. Aromatic 2-thio Acetates (9b-k) are prepared by analogy.

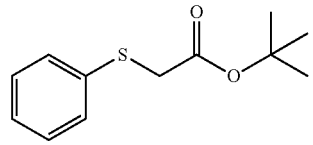

tert-butyl 2-(phenylthio)acetate (9a)

Pale yellow oil; $^1$H NMR (400 MHz, CDCl$_3$) δ 7.40 (d, J=7.7 Hz, 2H), 7.28 (t, J=7.5 Hz, 2H), 7.20 (dd, J=8.3, 6.3 Hz, 1H), 3.55 (s, 2H), 1.39 (s, 9H); $^{13}$C NMR (100 MHz, CDCl$_3$) δ 168.69, 135.23, 129.77, 128.82, 126.63, 81.76, 37.63, 27.79; IR: 1728.22, 1585.49, 1481.33, 1392.61, 1369.46, 1292.31, 1257.59, 1165.00, 1134.14, 948.98, 848.68 740.67, 690.52, 489.92 cm$^{-1}$; HRMS (ESI) calcd for C$_{12}$H$_{16}$O$_2$S m/z [M+H]$^+$: 225.0949; found: 225.0948.

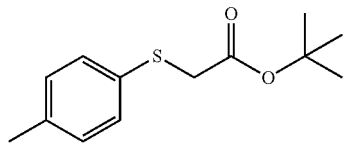 [SMILES: Cc1ccc(SCC(=O)OC(C)(C)C)cc1]

tert-butyl 2-(p-tolylthio)acetate (9b)

Colorless oil; 1H NMR (400 MHz, CDCl$_3$) δ 7.32 (d, J=8.1 Hz, 2H), 7.10 (d, J=8.0 Hz, 2H), 3.50 (s, 2H), 2.32 (s, 3H), 1.40 (s, 9H); $^{13}$C NMR (100 MHz, CDCl$_3$) δ 168.91, 136.97, 131.48, 130.69, 129.64, 81.70, 38.38, 27.86, 21.01; IR: 1728.22, 1492.90, 1454.33, 1392.61, 1369.46, 1292.31, 1257.59, 1168.86, 1134.14, 948.98, 806.25 cm$^{-1}$; HRMS (ESI) calcd for C$_{13}$H$_{18}$O$_2$S m/z [M+H]$^+$: 239.1106; found: 239.1109.

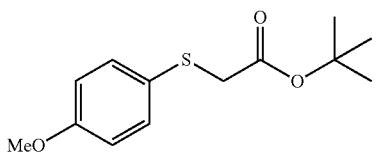 [SMILES: COc1ccc(SCC(=O)OC(C)(C)C)cc1]

tert-butyl 2-((4-methoxyphenyl)thio)acetate (9c)

Colorless oil; $^1$H NMR (400 MHz, CDCl$_3$) δ 7.41 (d, J=8.8 Hz, 2H), 6.84 (d, J=8.8 Hz, 2H), 3.79 (s, 3H), 3.43 (s, 2H), 1.39 (s, 9H); 13C NMR (100 MHz, CDCl$_3$) δ 169.03, 159.44, 133.90, 125.30, 114.51, 81.56, 55.30, 39.58, 27.88; IR: 1728.22, 1593.20, 1492.90, 1462.04, 1392.61, 1369.46, 1288.45, 1246.02, 1172.72, 1130.29, 1029.99, 948.98, 829.39 cm$^{-1}$; HRMS (ESI) calcd for C$_{13}$H$_{18}$O$_3$S m/z [M+H]$^+$: 255.1055; found: 255.1055.

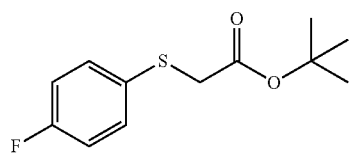 [SMILES: CC(C)(C)OC(=O)CSc1ccc(F)cc1]

tert-butyl 2-((4-fluorophenyl)thio)acetate (9d)

Colorless oil; $^1$H NMR (400 MHz, CDCl$_3$) δ 7.51-7.32 (m, 2H), 7.06-6.89 (m, 2H), 3.47 (s, 2H), 1.38 (s, 9H); $^{13}$C NMR (100 MHz, CDCl$_3$) δ 168.64, 162.18 (d, J=247.3 Hz), 133.11 (d, J=8.1 Hz), 130.04 (d, J=3.4 Hz), 115.97 (d, J=21.9 Hz), 81.82, 38.72, 27.82; $^{19}$F NMR (376 MHz, CDCl$_3$) δ −114.44; IR: 1728.22, 1589.34, 1492.90, 1454.33, 1392.61, 1369.46, 1292.31, 1230.58, 1138.00, 1091.71, 948.98, 829.39, 628.79 cm$^{-1}$; HRMS (ESI) calcd for C$_{12}$H$_{15}$FO$_2$S m/z [M+H]$^+$: 243.0855; found: 243.0853.

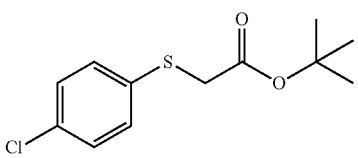

tert-butyl 2-((4-chlorophenyl)thio)acetate (9e)

Colorless oil; $^1$H NMR (400 MHz, CDCl$_3$) δ 7.33 (d, J=8.6 Hz, 2H), 7.25 (d, J=8.6 Hz, 2H), 3.52 (s, 2H), 1.40 (s, 9H); $^{13}$C NMR (100 MHz, CDCl$_3$) δ 168.48, 133.81, 132.81, 131.20, 129.01, 82.08, 37.78, 27.86; IR: 1728.22, 1477.47, 1454.33, 1392.61, 1369.46, 1292.31, 1257.59, 1138.00, 1095.57, 1010.70, 948.98, 817.82 cm$^{-1}$; HRMS (ESI) calcd for C$_{12}$H$_{15}$ClO$_2$S m/z [M+H]*: 259.0560; found: 259.0553.

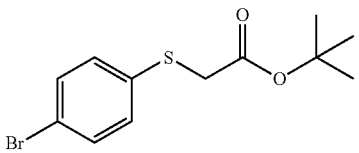 [SMILES: CC(C)(C)OC(=O)CSc1ccc(Cl)cc1]

tert-butyl 2-((4-bromophenyl)thio)acetate (9f)

Colorless oil; 1H NMR (400 MHz, CDCl$_3$) δ 7.46-7.36 (m, 2H), 7.31-7.22 (m, 2H), 3.52 (s, 2H), 1.40 (s, 9H); $^{13}$C NMR (100 MHz, CDCl$_3$) δ 168.41, 134.53, 131.91, 131.24, 120.62, 82.08, 37.55, 27.84; IR: 1716.65, 1454.33, 1392.61, 1369.46, 1288.45, 1257.59, 1130.29, 1091.71, 1068.56, 1006.84, 948.98, 810.10 cm$^{-1}$; HRMS (ESI) calcd for C$_{12}$H$_{15}$BrO$_2$S m/z [M+H]$^+$: 303.0054; found: 303.0051.

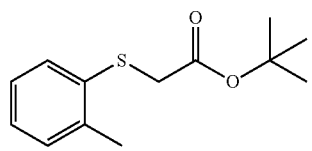 [SMILES: Cc1ccccc1SCC(=O)OC(C)(C)C]

tert-butyl 2-(o-tolylthio)acetate (9g)

Colorless oil; $^1$H NMR (400 MHz, CDCl$_3$) δ 7.41-7.33 (m, 1H), 7.22-7.08 (m, 3H), 3.54 (s, 2H), 2.42 (s, 3H), 1.40 (s, 9H); $^{13}$C NMR (100 MHz, CDCl$_3$) δ 168.61, 137.99, 134.35, 130.07, 129.21, 126.49, 126.37, 81.73, 36.83, 27.77, 20.29; IR: 1728.22, 1589.34, 1454.33, 1369.46, 1292.31, 1257.59, 1165.00, 1130.29, 948.98, 748.38 cm$^{-1}$; HRMS (ESI) calcd for C$_{13}$H$_{18}$O$_2$S m/z [M+H]$^+$: 239.1106; found: 239.1100.

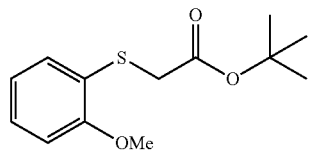 [SMILES: COc1ccccc1SCC(=O)OC(C)(C)C]

tert-butyl 2-((2-methoxyphenyl)thio)acetate (9h)

Pale yellow oil; $^1$H NMR (400 MHz, CDCl$_3$) δ 7.37 (d, J=7.6 Hz, 1H), 7.23 (t, J=7.5 Hz, 1H), 6.90 (t, J=7.6 Hz, 1H), 6.86 (d, J=8.2 Hz, 1H), 3.89 (s, 3H), 3.54 (s, 2H), 1.36 (s, 9H); $^{13}$C NMR (100 MHz, CDCl$_3$) δ 168.86, 157.95, 131.56, 128.41, 122.71, 120.87, 110.59, 81.51, 55.73, 35.99, 27.82; IR: 1728.22, 1712.79, 1581.63, 1454.33, 1392.61, 1369.46, 1292.31, 1246.02, 1172.72, 1122.57, 1072.42, 1026.13, 952.84, 848.68, 748.38, 682.80, 578.64 cm$^{-1}$; HRMS (ESI) calcd for C$_{13}$H$_{18}$O$_3$S m/z [M+H]$^+$: 255.1055; found: 255.1059.

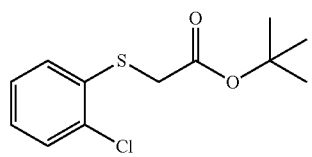 [SMILES: CC(C)(C)OC(=O)CSc1ccccc1Cl]

tert-butyl 2-((2-chlorophenyl)thio)acetate (9i)

Pale yellow oil; $^1$H NMR (400 MHz, CDCl$_3$) δ 7.41-7.31 (m, 2H), 7.20 (td, J=7.6, 1.5 Hz, 1H), 7.13 (td, J=7.6, 1.6 Hz, 1H), 3.59 (s, 2H), 1.39 (s, 9H); $^{13}$C NMR (100 MHz, CDCl$_3$) δ 168.13, 134.45, 133.92, 129.67, 129.64, 127.32, 127.05, 82.04, 36.17, 27.77; IR: 1728.22, 1577.77, 1454.33, 1392.61, 1369.46, 1296.16, 1257.59, 1141.86, 1033.85, 948.98, 848.68, 748.38 cm$^{-1}$; HRMS (ESI) calcd for $C_{12}H_{15}ClO_2S$ m/z [M+H]$^+$: 259.0560; found: 259.0563.

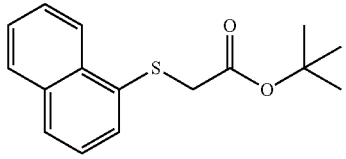 [SMILES: CC(C)(C)OC(=O)CSc1cccc2ccccc12]

tert-butyl 2-(naphthalen-1-ylthio)acetate (9j)

Pale yellow solid; mp: 43.6-45.3° C.; $^1$H NMR (400 MHz, CDCl$_3$) δ 8.44 (d, J=8.4 Hz, 1H), 7.85 (d, J=8.1 Hz, 1H), 7.78 (d, J=8.2 Hz, 1H), 7.70 (d, J=7.1 Hz, 1H), 7.58 (t, J=7.1 Hz, 1H), 7.52 (t, J=7.2 Hz, 1H), 7.41 (t, J=7.7 Hz, 1H), 3.60 (s, 2H), 1.34 (s, 9H); $^{13}$C NMR (100 MHz, CDCl$_3$) δ 168.70, 133.94, 133.10, 132.18, 130.02, 128.58, 128.27, 126.62, 126.25, 125.51, 125.11, 81.76, 38.19, 27.80; IR: 1728.22, 1566.20, 1504.48, 1454.33, 1392.61, 1369.46, 1296.16, 1265.30, 1134.14, 948.98, 798.53, 771.53, 740.67, 702.09 cm$^{-1}$; HRMS (ESI) calcd for $C_{16}H_{18}O_2S$ m/z [M+H]$^+$: 275.1106; found: 275.1100.

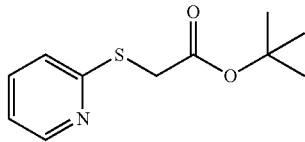

tert-butyl 2-(pyridin-2-ylthio)acetate (9k)

Pale yellow oil; $^1$H NMR (400 MHz, CDCl$_3$) δ 8.38 (ddd, J=4.9, 1.8, 0.9 Hz, 1H), 7.48 (ddd, J=8.0, 7.4, 1.9 Hz, 1H), 7.22 (dt, J=8.1, 1.0 Hz, 1H), 6.98 (ddd, J=7.3, 4.9, 1.0 Hz, 1H), 3.88 (s, 2H), 1.44 (s, 9H); $^{13}$C NMR (100 MHz, CDCl$_3$) δ 168.67, 157.33, 149.14, 135.98, 122.00, 119.65, 81.68, 33.55, 27.90; IR: 2978.09, 1732.08, 1577.77, 1558.48, 1454.33, 1415.75, 1369.46, 1300.02, 1257.59, 1145.72, 1122.57, 948.98, 852.54, 759.95, 725.23 cm$^{-1}$; HRMS (ESI) calcd for $C_{11}H_{15}NO_2S$ m/z [M+H]$^+$: 226.0902; found: 226.0892.

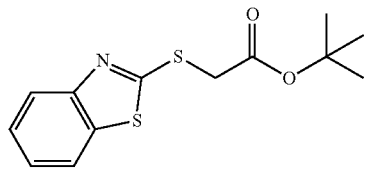 [SMILES: CC(C)(C)OC(=O)CSc1nc2ccccc2s1]

tert-butyl 2-(benzo[d]thiazol-2-ylthio)acetate (9l)

(see Qingping Zeng et al Benzoheterocyclecarboxaldehyde derivatives as IRE-1α inhibitors and their preparation and use for the treatment of diseases. WO2011127070A2 (2011)): Pale yellow oil; $^1$H NMR (400 MHz, CDCl$_3$) 7.84 (d, J=8.1 Hz, 1H), 7.75 (d, J=8.0 Hz, 1H), 7.41 (t, J=7.7 Hz, 1H), 7.29 (t, J=7.6 Hz, 1H), 4.07 (s, 2H), 1.47 (s, 10H); $^{13}$C NMR (100 MHz, CDCl$_3$) δ 167.18, 165.09, 152.94, 135.47, 126.03, 124.34, 121.57, 121.02, 82.57, 36.34, 27.91; IR: 2978.09, 2360.87, 1732.08, 1462.04, 1427.32, 1392.61, 1369.46, 1303.88, 1145.72, 1002.98, 948.98, 852.54, 756.10, 725.23, 489.92 cm$^{-1}$; HRMS (ESI) calcd for $C_{13}H_{15}NO_2S_2$ m/z [M+H]$^+$: 282.0622; found: 282.0618.

Synthesis of Other Sulfide Substrates (11a-g)

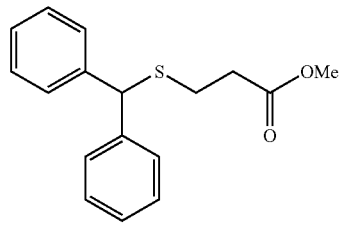 [SMILES: COC(=O)CCSC(c1ccccc1)c1ccccc1]

methyl 3-(benzhydrylthio)propanoate (11a)

(see Andrea Altieri et al. Sulfur-containing amide-based [2]rotaxanes and molecular shuttles. *Chem. Sci.* 2, 1922-1928 (2011)): Pale yellow oil; 94% yield; $^1$H NMR (400 MHz, CDCl$_3$) δ 7.43 (d, J=7.5 Hz, 4H), 7.38-7.28 (m, 4H), 7.28-7.18 (m, 2H), 5.21 (s, 1H), 3.68 (s, 3H), 2.69 (dd, J=11.2, 4.0 Hz, 2H), 2.55 (dd, J=11.0, 3.9 Hz, 2H); $^{13}$C NMR (100 MHz, CDCl$_3$) δ 172.22, 141.03, 128.55, 128.25, 127.24, 54.24, 51.72, 34.09, 27.14; IR: 1728.22, 1600.92, 1492.90, 1446.61, 1435.04, 1357.89, 1246.02, 1199.72, 1172.72, 1076.28, 1029.99, 979.84, 829.39, 748.38, 702.09, 628.79, 586.36 cm$^{-1}$; HRMS (ESI) calcd for $C_{17}H_{18}O_2S$ m/z [M+H]*: 287.1106; found: 287.1106.

3-(benzhydrylthio)propanamide (11b)

(see Sidney Liang. Improved process for preparing benzhydrylthioacetamide. WO2004075841A2 (2004); Surendra B. Bhatt et al. Improved process for the preparation of 2-[(diphenylmethyl)thio]acetamide, intermediate for the preparation of Modafinil, from 2-[(diphenylmethyl)thio]acetic acid, alcohols and ammonia.

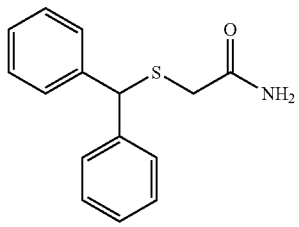 [SMILES: NC(=O)CSC(c1ccccc1)c1ccccc1]

WO2004075827A2 (2004)): White solid; mp: 111.0-112.2° C.; $^1$H NMR (400 MHz, CD$_3$OD) δ 7.42 (d, J=7.7 Hz, 4H), 7.28 (t, J=7.6 Hz, 4H), 7.20 (t, J=7.3 Hz, 2H), 5.35 (s, 1H), 3.03 (s, 2H); $^{13}$C NMR (100 MHz, CD$_3$OD) δ 174.60, 142.00, 129.52, 129.36, 128.32, 55.30, 36.00; IR: 3360.00, 1643.35, 1631.78, 1489.05, 1373.32, 1080.14, 921.97, 698.23 cm$^{-1}$; HRMS (ESI) calcd for $C_{15}H_{15}NOS$ m/z [M+H]$^+$: 258.0953; found: 258.0958.

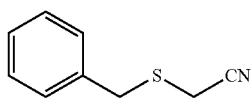 [SMILES: N#CCSCc1ccccc1]

2-(benzylthio)acetonitrile (11c)

(Gavin Chit Tsui, Quentin Glenadel, Chan Lau & Mark Lautens. Rhodium(I)-Catalyzed Addition of Arylboronic Acids to (Benzyl-/Arylsulfonyl)acetonitriles: Efficient Synthesis of (Z)-β-Sulfonylvinylamines and β-Keto Sulfones. *Org. Lett.* 13, 208-211 (2011)): Pale yellow oil; $^1$H NMR (400 MHz, CDCl$_3$) δ 7.30-7.23 (m, 4H), 7.23-7.18 (m, 1H), 3.82 (s, 2H), 2.97 (s, 2H); $^{13}$C NMR (100 MHz, CDCl$_3$) δ 135.64, 129.00, 128.83, 127.78, 116.19, 35.98, 15.84; IR: 2245.14, 1955.82, 1600.92, 1492.90, 1454.33, 1396.46, 1249.87, 1230.58, 1184.29, 1072.42, 1029.99, 921.97, 894.97, 771.53, 725.23, 702.09, 675.09, 563.21 cm$^{-1}$; HRMS (ESI) calcd for C$_9$H$_9$NS m/z [M+H]$^+$:164.0534; found: 164.0548.

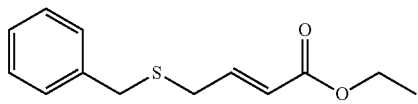 [SMILES: CCOC(=O)/C=C/CSCc1ccccc1]

(E)-ethyl 4-(benzylthio)but-2-enoate (11d)

(Peter Schwenkkraus & Hans Hartwig Otto. Properties and reactions of substituted 1,2-thiazetidine 1,1-dioxides: C-3 substituted β-sultams. *Arch. Pharm.* (Weinheim, Ger.) 326, 519-523 (1993); Charles M. Marson et al. Aromatic sulfide inhibitors of histone deacetylase based on arylsulfinyl-2,4-hexadienoic acid hydroxyamides. *J. Med. Chem.* 49, 800-805 (2006)): Pale yellow oil; $^1$H NMR (400 MHz, CDCl$_3$) δ 7.36-7.28 (m, 4H), 7.27-7.22 (m, 1H), 6.95-6.77 (m, 1H), 5.84 (dt, J=15.5, 1.3 Hz, 1H), 4.21 (q, J=7.1 Hz, 2H), 3.66 (s, 2H), 3.11 (dd, J=7.4, 1.3 Hz, 2H), 1.31 (t, J=7.1 Hz, 3H); $^{13}$C NMR (100 MHz, CDCl$_3$) δ 166.02, 143.39, 137.54, 128.98, 128.56, 127.16, 123.09, 60.44, 35.22, 31.86, 14.21; IR: 3028.24, 1712.79, 1651.07, 1492.90, 1454.33, 1369.46, 1315.45, 1265.30, 1195.87, 1149.57, 1041.56, 979.84, 860.25, 748.38, 702.09 cm$^{-1}$; HRMS (ESI) calcd for C$_{13}$H$_{16}$O$_2$S m/z [M+H]$^+$: 237.0949; found: 237.0951.

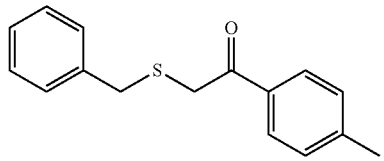 [SMILES: Cc1ccc(C(=O)CSCc2ccccc2)cc1]

2-(benzylthio)-1-(p-tolyl)ethanone (11e)

(Hossein Loghmani-Khouzani, Mohammad R. Poorheravi, Majid M. M. Sadeghi, Lorenzo Caggiano & Richard F. W. Jackson. α-Fluorination of β-ketosulfones by Selectfluor F-TEDA-BF4. *Tetrahedron* 64, 7419-7425 (2008)): To a suspension of K$_2$CO$_3$ (1.38 g, 10.0 mmol) and 2-bromo-1-(p-tolyl)ethanone (959 mg, 4.5 mmol) in EtOH (15 mL), benzyl mercaptan (587 μL, 5.0 mmol) was added dropwise. After vigorously stirring for 5 h until the complete consumption of 2-bromo-1-(p-tolyl)ethanone, EtOAc (50 mL) was added and the reaction mixture was diluted with water (10 mL). The aqueous layer was extracted with EtOAc (2×50 mL) and the combined organic layer was washed by brine and dried by Na$_2$SO$_4$, filtered and concentrated. The crude residue was subjected to purification by flash column chromatography (silica gel, hexanes: EtOAc, gradient from 50:1 to 20:1) to afford the product as pale yellow solid; mp: 69.4-70.5° C.; $^1$H NMR (400 MHz, CDCl$_3$) δ 7.84 (d, J=8.2 Hz, 2H), 7.43-7.29 (m, 4H), 7.29-7.21 (m, 3H), 3.76 (s, 2H), 3.66 (s, 2H), 2.42 (s, 3H); $^{13}$C NMR (100 MHz, CDCl$_3$) δ 194.13, 144.17, 137.35, 132.89, 129.30, 129.23, 128.78, 128.47, 127.15, 36.08, 35.83, 21.63; IR: 1670.35, 1604.77, 1492.90, 1454.33, 1419.61, 1280.73, 1184.29, 1014.56, 837.11, 806.25, 771.53, 702.09, 551.64 cm$^{-1}$; HRMS (ESI) calcd for C$_{16}$H$_{16}$OS m/z [M+H]$^+$: 257.1000; found: 257.1000.

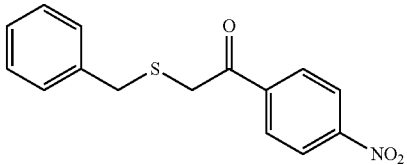 [SMILES: O=C(CSCc1ccccc1)c1ccc([N+](=O)[O-])cc1]

2-(benzylthio)-1-(4-nitrophenyl)ethanone (11f)

(Hossein Loghmani-Khouzani, Mohammad R. Poorheravi, Majid M. M. Sadeghi, Lorenzo Caggiano & Richard F. W. Jackson. α-Fluorination of β-ketosulfones by Selectfluor F-TEDA-BF4. *Tetrahedron* 64, 7419-7425 (2008)): Yellow solid; mp: 106.1-106.9° C.; $^1$H NMR (400 MHz, CDCl$_3$) δ 8.29 (d, J=8.8 Hz, 2H), 8.05 (d, J=8.8 Hz, 2H), 7.40-7.31 (m, 4H), 7.30-7.25 (m, 1H), 3.73 (s, 2H), 3.68 (s, 2H); $^{13}$C NMR (100 MHz, CDCl$_3$) δ 192.44, 150.30, 139.89, 136.73, 129.73, 129.25, 128.59, 127.43, 123.78, 36.09, 36.01; IR: 1678.07, 1600.92, 1519.91, 1415.75, 1350.17, 1319.31, 1269.16, 856.39, 732.95, 705.95 cm$^{-1}$; HRMS (ESI) calcd for C$_{15}$H$_{13}$NO$_3$S m/z [M+H]$^+$: 288.0694; found: 288.0687.

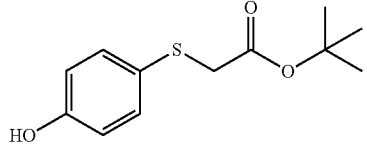 [SMILES: CC(C)(C)OC(=O)CSc1ccc(O)cc1]

tert-butyl 2-((4-hydroxyphenyl)thio)acetate (11g)

(see Katsukiyo Miura, Naoki Fujisawa, Hiroshi Saito, Di Wang & Akira Hosomi. Synthetic Utility of Stannyl Enolates as Radical Alkylating Agents1. *Org. Lett.* 3, 2591-2594 (2001)): Pale brown oil; $^1$H NMR (400 MHz, CDCl$_3$) δ 7.32 (d, J=8.5 Hz, 1H), 6.70 (d, J=8.5 Hz, 1H), 3.41 (s, 2H), 1.41 (s, 4H); $^{13}$C NMR (100 MHz, CDCl$_3$) δ 170.17, 156.25, 134.40, 124.20, 116.13, 82.22, 39.74, 27.86; IR: 3398.57, 1693.50, 1600.92, 1581.63, 1496.76, 1431.18, 1369.46, 1311.59, 1265.30, 1168.86, 952.84, 829.39, 640.37, 520.78 cm$^{-1}$; HRMS (ESI) calcd for C$_{12}$H$_{16}$O$_3$S m/z [M+H]$^+$: 241.0898; found: 241.0889.

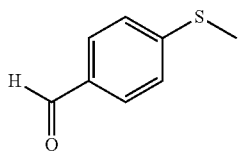

4-(methylthio)benzaldehye (11h) may be made by analogy to the processes described above, or may be obtained from commercial sources.

General Procedures

General Procedure 1: Sulfoxidation of Heterocyclic Sulfides Using Tungstate System

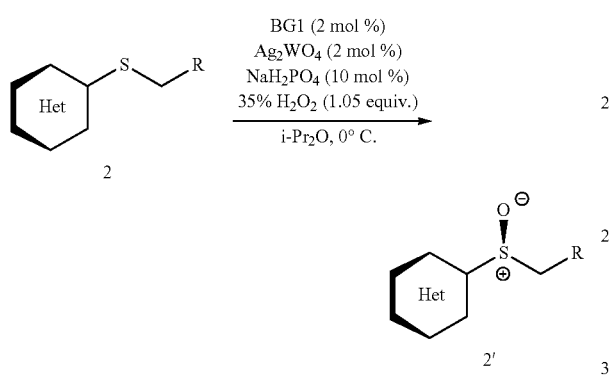

In a 4 mL sample vial, sulfides 2(0.2 mmol, 1.0 equiv), bisguanidinium chloride (0.004 mmol, 0.02 equiv), silver tungstate oxide (0.004 mmol, 0.02 equiv), sodium phosphate monobasic (0.02 mmol, 0.1 equiv) and solvent were added. The temperature of the solution is then lowered to the presupposed temperature. After stabilizing, $H_2O_2$ (1.05 equiv, 35% w/w) was injected in one portion into the system. The mixture was stirred for 24 hours to 48 hours, and the termination of reaction was monitored by TLC. The resulting suspension was quenched by saturated $Na_2S_2O_3$. EtOAc (0.5 mL×3) was used for extraction, and the organic layers were combined and dried over anhydrous $Na_2SO_4$. The organic solvent was removed in rotary evaporator (the water-bath temperature is under 38° C.), and the residues were purified by chromatography on silica gel to afford the desired products. R represents a chemical group as provided by the sulfides/sulfoxides in Examples 2-3.

General Procedure 2: Sulfoxidation of Phenyl Sulfides Using Tungstate System

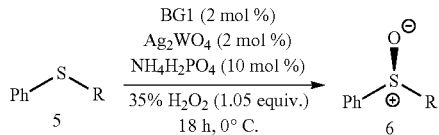

In a 10 mL sample vial, sulfides 5 (0.2 mmol, 1.0 equiv), bisguanidinium chloride (0.004 mmol, 0.02 equiv), silver tungstate oxide (0.004 mmol, 0.02 equiv), ammonium phosphate monobasic (0.02 mmol, 0.1 equiv) and 8 mL mixed solvent were added. The solvent mixture consisted of 4 mL dimethyl carbonate and 4 mL diethyl ether (diisopropyl ether in 5a). Then lower the solution to the presupposed temperature. After stabilizing, $H_2O_2$(1.05 equiv, 35% w/w) was injected in one portion into the system. The mixture was stirred for 18 hours, and the termination of reaction was monitored by TLC. The resulting suspension was quenched by saturated $Na_2S_2O_3$. EtOAc (0.5 mL×3) was used for extraction, and the organic layers were combined and dried over anhydrous $Na_2SO_4$. The organic solvent was removed in rotary evaporator (the water-bath temperature is under 38° C.), and the residues were purified by chromatography on silica gel to afford the desired products. R represents a chemical group as provided by the sulfides/sulfoxides in Example 5.

General Procedure 3: Sulfoxidation of Sulfides Using Molybdate System

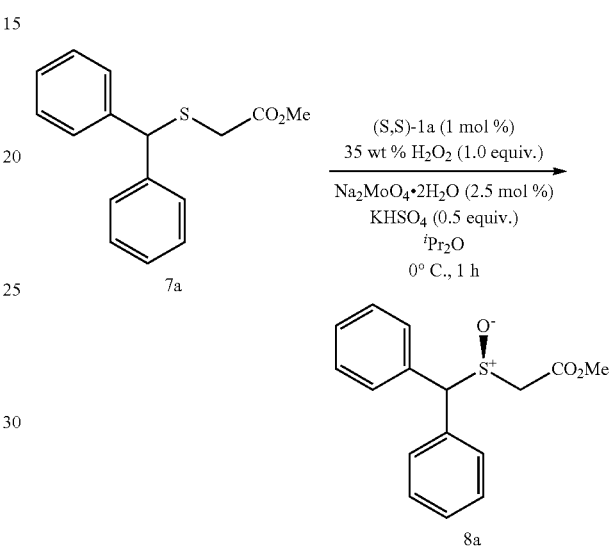

A 10 mL round-bottomed flask was charged with a solution of methyl 2-(benzhydrylthio)acetate 7a (54.4 mg, 0.2 mmol, 1.0 equiv.) and bis-guanidinium phase-transfer catalyst 1a (2.8 mg, 0.002 mmol, 0.01 equiv.) in $^iPr_2O$ (4 mL). Then $Na_2MoO_4\cdot 2H_2O$ (1.2 mg, 0.005 mmol, 0.025 equiv.) and $KHSO_4$ (13.6 mg, 0.1 mmol, 0.5 equiv.) were added. The reaction mixture was stirred for 5 min in an ice-bath, and then $H_2O_2$(35%, 17.2 µL, 0.2 mmol, 1.0 equiv) was added in one portion. The resulting mixture was stirred vigorously at 0° C. and monitored by TLC until 7a was completely consumed. Purification by column chromatography on silica gel using $CH_2Cl_2$: EtOAc 2:1 as the eluent gave the desired sulfoxide 8a as a white solid. Minor changes in the amount of $KHSO_4$ and choice of Molybdate salt ($K_2MoO_4$) and solvent ($^nBu_2O$) should be conducted for some substrates in order to achieve slightly better enantioselectivity.

Computational Studies

Calculations were performed using the Gaussian 09 software package (Frisch, M. J.; Trucks, G. W., et al., *Gaussian 09*, Gaussian, Inc.: Wallingford, Conn., USA, 2009). Two different models were considered. The small model (SM) was used to study the reactivity of different tungstate species and does not contain the BG-1 structure. The other multi-scale model was used to study the reactivity of the complete ion-pair structure by means of a two-layer ONIOM (QM: QM') (Dapprich, S, et al., *J. Mol. Struct.* (*Theochem*) 1999, 462, 1-21) method. The B3LYP density functional theory (DFT) method and the semiempirical PM6 (Stewart, J. J. P. *J. Mol. Model.* 2007, 13, 1173-1213) method were used for the QM and QM' calculations, respectively.

For both models, DFT calculations were performed with the hybrid B3LYP functional [Becke, A. D., *The Journal of Chemical Physics* 1993, 98 (7), 5648-5652; Lee, C.; Yang, W.; Parr, R. G., *Physical Review B* 1988, 37 (2), 785-789; Vosko, S. H.; Wilk, L.; Nusair, M., *Canadian Journal of Physics* 1980, 58 (8), 1200-1211] and two basis sets, B1 and B2. B1 is a combination of the LANL2DZ effective core potential basis set (Hay, P. J.; Wadt, W. R., *The Journal of Chemical Physics* 1985, 82 (1), 299-310) for W and the 6-31g* basis set (Wiberg, K. B., *Journal of Computational Chemistry* 1986, 7 (3), 379-379) for remaining atoms, which was used for geometry optimization calculations. Vibrational analysis were done for B3LYP/B1-derived stationary points to confirm their nature and to obtain zero-point energy (ZPE) corrections. To improve the accuracy of energies, single-point energy calculations were performed on the B3LYP/B1 geometries with basis set B2, which is the combination of SDD effective core potential basis set (Dolg, M.; Wedig, U.; Stoll, H.; Preuss, H., *The Journal of Chemical Physics* 1987, 86 (2), 866-872) for W and 6-311+g(df,p) on other atoms. Solvent effects on the reactions were included in geometry optimizations, using a self-consistent reaction field (SCRF) method called IEFPCM (Tomasi, J.; Mennucci, B.; Cammi, R., *Chemical Reviews* 2005, 105 (8), 2999-3094) as implemented in Gaussian 09. Visualization of resulting structures was generated using UCSF Chimera, unless stated otherwise (Pettersen, E. F.; Goddard, T. D.; Huang, C. C.; Couch, G. S.; Greenblatt, D. M.; Meng, E. C.; Ferrin, T. E. *J. Comput. Chem.* 2004, 25 (13), 1605-1612).

EXAMPLES

Example 1: Synthetic Protocol of Isolated Complex (R,R)-1c

To a solution of $Na_2MoO_4 \cdot 2H_2O$ (24.1 mg, 0.1 mmol, 2.5 mol %) dissolved in 1M $H_2SO_4$ (1 mL, 0.25 equiv.), 35% $H_2O_2$ (345 μL, 4.0 mmol, 1.0 equiv.) was added dropwise to give a yellow solution at room temperature. Then the above solution was added dropwise to a solution of (R,R)-1b (56.4 mg, 0.04 mmol, 1 mol %) in $Et_2O$ (2 mL). After vigorously stirred for 15 minutes, a pale-yellow precipitate was formed in the $Et_2O$ layer. After further stirring for 2h and removal of $Et_2O$ by evaporation, 4 mL deionized water was added and the resulting heterogeneous mixture was submitted to ultrasound for 1 minute. Then the pale-yellow solid was filtered off and washed with deionized water (40 mL). After dried with concentrated $H_2SO_4$ by using vacuum oil pump, (R,R)-1c was obtained as a pale-yellow powder (65.5 mg, 91% yield) and its structure was characterized and determined by X-ray single crystal diffraction. Increase of the amount of $Na_2MoO_4 \cdot 2H_2O$ to 0.1 equivalent or replacement of 1M $H_2SO_4$ by 0.5 equivalent of solid $KHSO_4$ all led to the formation of identical complex (R,R)-1c, which is confirmed by X-ray diffraction analysis. FIG. 14 provides a general synthetic route towards (R,R)-1c. $^1$H NMR (400 MHz, DMF-$d_7$) δ 7.45-7.38 (m, 12H), 7.37 (s, 4H), 7.21 (dd, J=6.3, 2.7 Hz, 8H), 7.07 (d, J=1.4 Hz, 8H), 5.22 (d, J=14.5 Hz, 4H), 4.89 (d, J=14.5 Hz, 4H), 4.57 (s, 4H), 4.55 (t, J=12.7 Hz, 8H), 1.17 (s, 72H); $^{13}$C NMR (100 MHz, DMF-$d_7$) δ 164.19, 152.34, 139.37, 133.86, 130.54, 130.01, 127.74, 124.64, 123.49, 70.74, 54.40, 50.25, 35.63, 31.94; $^{95}$Mo NMR (26 MHz, DMF-$d_7$) δ -199.29; IR: 2962.66, 1597.06, 1527.62, 1477.47, 1454.33, 1361.74, 1284.59, 1249.87, 1199.72, 1157.29, 1114.86, 1076.28, 1049.27, 1018.41, 972.12 (Mo=O), 937.40, 918.12, 871.82 (O—O), 759.55, 702.09, 663.51 (Mo—($O_2$)), 590.22 (Mo—($O_2$)). FIG. 16 provides the Infrared spectrum of (R,R)-1c.

Figure 8:
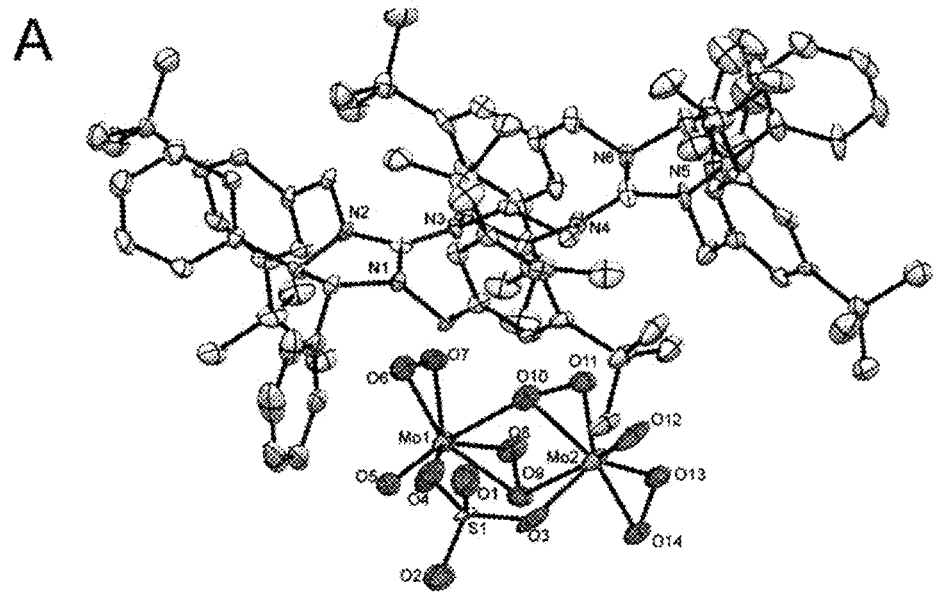
FIG. 8A depicts an ORTEP diagram showing X-ray crystal structure of complex (R,R)-1c (top)
FIG. 8B depicts its constituent cationic and anionic parts.
Figure 8:
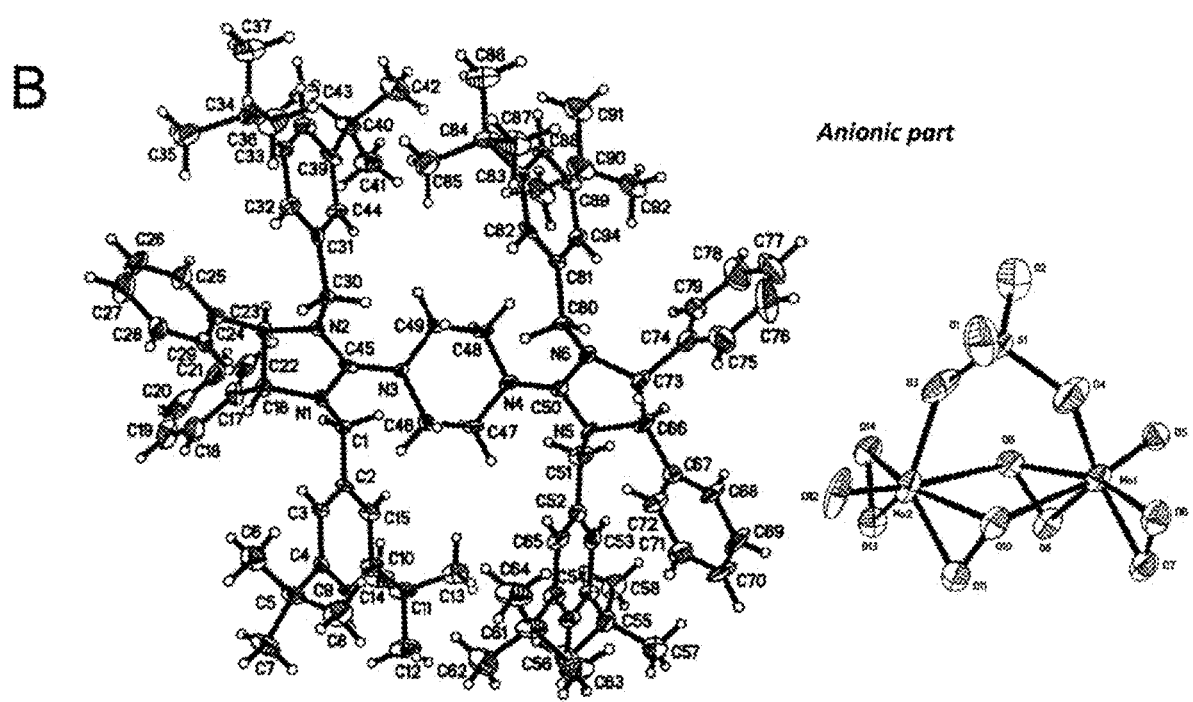
Figure 9A:
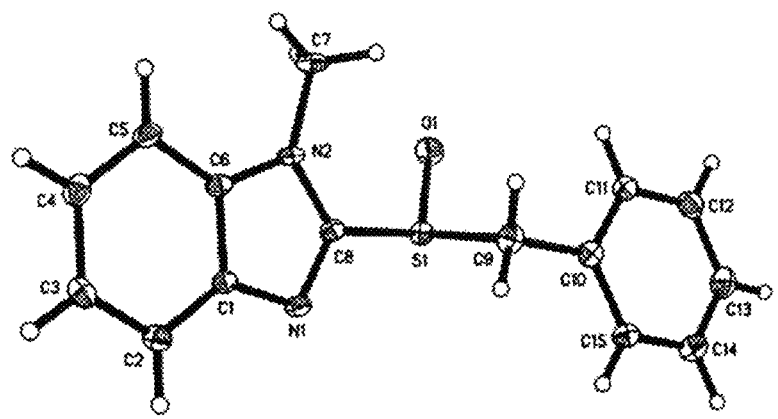
Figure 9B:
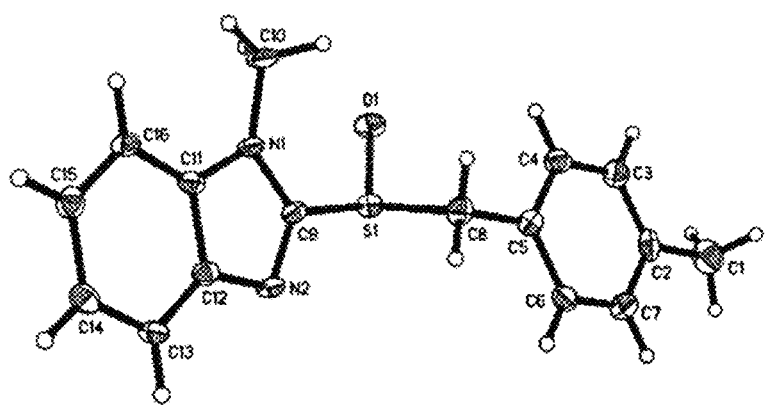
Figure 9C:
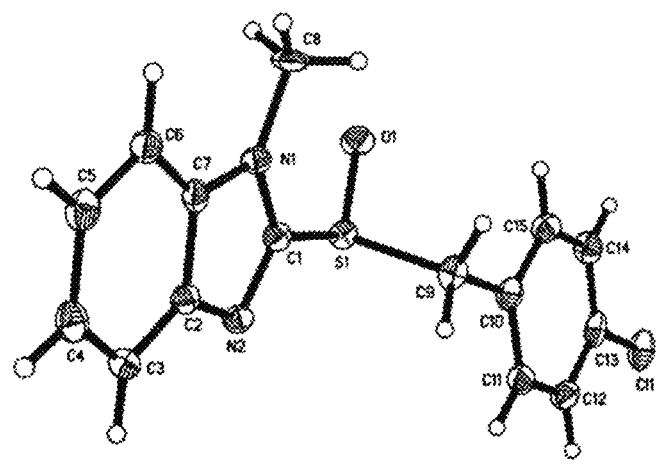
Figure 9D:
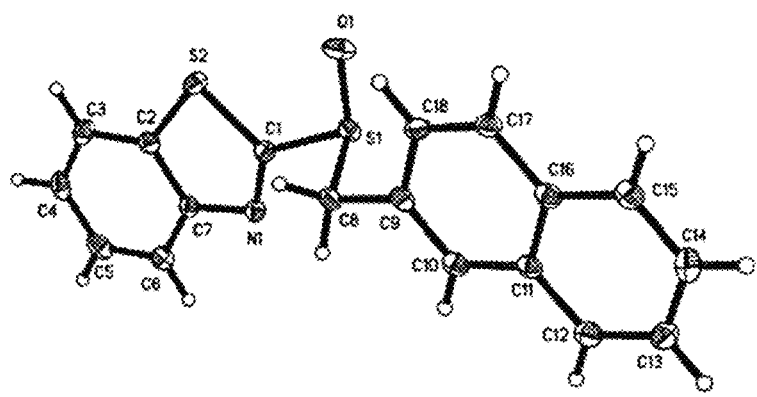
Figure 9E:
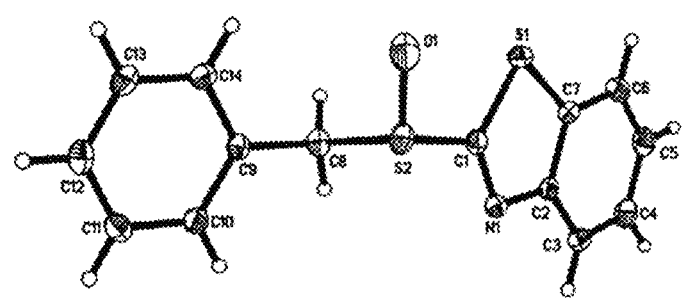

A single crystal structure of (R,R)-1c is provided in FIG. 8. Crystal data for (R,R)-1c: [$C_{94}H_{124}Mo_2N_6O_{14}S \cdot 2C_3H_7NO \cdot C_4H_{10}O$], M=2006.24, monoclinic, P 1 21 1, a=9.9398(8), b=30.471(3), c=17.5604(15) Å, α=90, β=97.837(3)°, γ=90°, V=5268.9(8) Å$^3$, Z=2, $ρ_{calcd}$=1.265 g/cm$^3$, μ(CuKα)=0.324 mm$^{-1}$, T=103(2) K, Wavelength=0.71073 Å, yellow plate. Bruker X8 CCD X-ray diffractionmeter; 20085 independent measured reflections, F$^2$ refinement, $R_1$(obs)=0.0715, $wR_2$(all)=0.1585, 12673 independent observed absorption-corrected reflections, 1426 parameters. Crystallographic data for this paper have been deposited at the Cambridge Crystallographic Data Centre under deposition number CCDC 1456990.

Example 2: Optimization of Reaction Conditions for Tungstate-Catalyzed Oxidation

TABLE 1

Optimization of the reaction conditions.

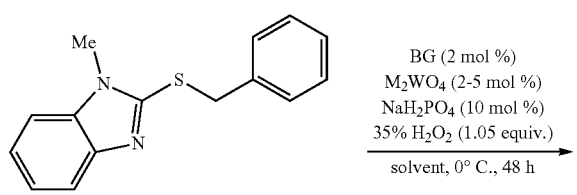

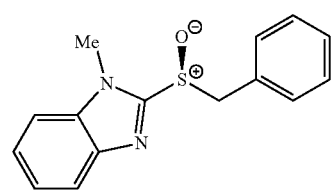

TABLE 1-continued

![Bisguanidinium catalyst structure with two imidazolinium rings linked by piperazine, bearing Ph and R substituents]

| entry | BG | M$_x$(WO$_4$)$_y$ | Additive | Solvent | yield (%)[b] | ee (%)[c] |
|---|---|---|---|---|---|---|
| 1[d] | BG-1 | — | — | Et$_2$O | N.R. | N.A. |
| 2 | BG-1 | Na$_2$WO$_4$ | — | Et$_2$O | 20 | −5 |
| 3 | BG-1 | Na$_2$WO$_4$ | NaH$_2$PO$_4$ | Et$_2$O | 36 | 20 |
| 4 | BG-1 | K$_2$WO$_4$ | NaH$_2$PO$_4$ | Et$_2$O | 18 | −2 |
| 5 | BG-1 | (NH$_4$)$_2$WO$_4$ | NaH$_2$PO$_4$ | Et$_2$O | 48 | 42 |
| 6 | BG-1 | Ag$_2$WO$_4$ | LiH$_2$PO$_4$ | Et$_2$O | 70 | 90 |
| 7 | BG-1 | Ag$_2$WO$_4$ | NaH$_2$PO$_4$ | Et$_2$O | 83 | 88 |
| 8 | ent-BG-1 | Ag$_2$WO$_4$ | NaH$_2$PO$_4$ | Et$_2$O | 90 | −89 |
| 9 | BG-1 | Ag$_2$WO$_4$ | KH$_2$PO$_4$ | Et$_2$O | 83 | 84 |
| 10 | BG-1 | Ag$_2$WO$_4$ | NH$_4$H$_2$PO$_4$ | Et$_2$O | 82 | 82 |
| 11 | BG-1 | Ag$_2$WO$_4$ | NaHSO$_4$ | Et$_2$O | 52 | 80 |
| 12 | BG-1 | Ag$_2$WO$_4$ | NaH$_2$PO$_4$ | Tol | 60 | 74 |
| 13 | BG-1 | Ag$_2$WO$_4$ | NaH$_2$PO$_4$ | DCM | 68 | 20 |
| 14 | BG-1 | Ag$_2$WO$_4$[e] | NaH$_2$PO$_4$ | Et$_2$O | 55 | 50 |
| 15 | BG-1 | Ag$_2$WO$_4$[e] | NaH$_2$PO$_4$ | i-Pr$_2$O | 96 | 92 |
| 16 | BG-2 | Ag$_2$WO$_4$[e] | NaH$_2$PO$_4$ | i-Pr$_2$O | 65 | 63 |
| 17 | BG-3 | Ag$_2$WO$_4$[e] | NaH$_2$PO$_4$ | i-Pr$_2$O | 63 | 50 |
| 18 | BG-4 | Ag$_2$WO$_4$[e] | NaH$_2$PO$_4$ | i-Pr$_2$O | 52 | 32 |
| 19 | BG-5 | Ag$_2$WO$_4$[e] | NaH$_2$PO$_4$ | i-Pr$_2$O | 84 | 8 |
| 20 | BG-1 | — | NaH$_2$PO$_4$ | i-Pr$_2$O | 19 | N.A. |

BG1: R = 3,5-(tBu)$_2$PhCH$_2$
BG2: R = 4-MeO-3,5-(tBu)$_2$PhCH$_2$
BG3: R = 2-fluoro-3,5-(tBu)$_2$PhCH$_2$
BG4: R = 2-chloro-3,5-(tBu)$_2$PhCH$_2$
BG5: R = 2-bromo-3,5-(tBu)$_2$PhCH$_2$
Unless otherwise stated, reaction was performed with 2a (0.05 mmol), H$_2$O$_2$ (0.0525 mmol, 1.05 equiv, 35% w/w), BG (0.001 mmol, 2.0 mol %), M$_x$(WO$_4$)$_y$ (0.0025 mmol, 5.0 mol %), 1.0 mL Et$_2$O at 0° C.
[b]Yield of isolated product.
[c]Determined by HPLC analysis on a chiral stationary phase.
[d]No reaction was also observed at room temperature.
[e]2.0 mol % of Ag$_2$WO$_4$ was used.

As set out in Table 1, reaction conditions for tungstate-catalyzed sulfoxidation were optimized with variance on the identity and/or amount of, for example, the organic cation, the tungstate-containing salt, the phosphate-containing additive and the solvent used. Sulfoxide product 2'a was made from its reduced form via General Procedure 1, unless otherwise stated.

Benzimidazole-derived benzyl sulfide 2a was chosen as the model substrate. In the presence of 2.0 mol % of bisguanidinium BG1 with Et$_2$O as solvent (Table 1, entry 1), no reaction was found when only H$_2$O$_2$ was used. This indicates that BG1 alone cannot catalyze the reaction. When 5.0 mol % of Na$_2$WO$_4$ was added, the reaction gave sulfoxide 2'a in poor yield and low enantioselectivity (entry 2). It is only when 10 mol % NaH$_2$PO$_4$ was added, the yield of sulfoxide 2'a improved significantly to 36% and its ee value improved to 20% (entry 3). When Na$_2$HPO$_4$ and Na$_3$PO$_4$ were used instead, the reactions were inhibited.

Next, a range of commercially available tungstate salts, such as K$_2$WO$_4$, (NH$_4$)$_2$WO$_4$ and Ag$_2$WO$_4$ were evaluated (entries 4-6). Sulfoxide 2'a was obtained in 83% yield with 88% ee value when Ag$_2$WO$_4$ was used (entry 7). When the catalyst loading of Ag$_2$WO$_4$ was decreased to 2.0 mol %, it is necessary to change the solvent to diisopropyl ether to provide the best results (entry 15). Other bisguanidiniums BG2-5 featuring different benzyl groups were unable to improve the results obtained with BG1 (entries 16-19). It was also confirmed that the use of NaH$_2$PO$_4$ in the absence of Ag$_2$WO$_4$ did not promote the sulfoxidation reaction (entry 20). Characterization data of 2'a is provided in Example 3.

Example 3: Enantioselective Sulfoxidation of Heterocyclic Sulfides and Characterization of Sulfoxide Products Scheme 1: Enantioselective sulfoxidation of heterocyclic sulfides.
Unless otherwise stated, reactions were carried out on 0.2 mmol scale in 4.0 mL solvent for 36 hours; yield values refer to isolated yields after purification and ee was determined by chiral HPLC. [a]5.0 mol % of Ag$_2$WO$_4$ was used. [b]Et$_2$O as the solvent. [c]8.0 mL iPr$_2$O was used.

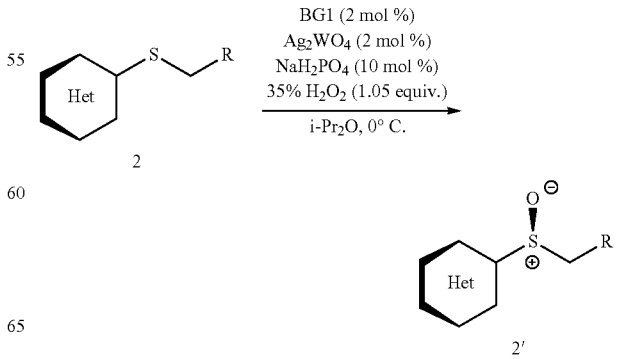

| | |
|---|---|
| 2'a 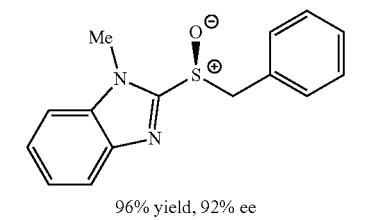  96% yield, 92% ee | 2'g 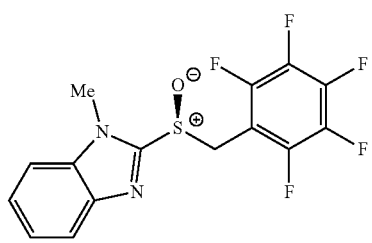  84% yield, 92% ee |
| 2'b 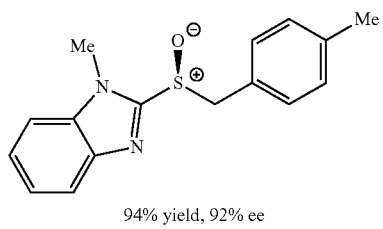  94% yield, 92% ee | 2'h 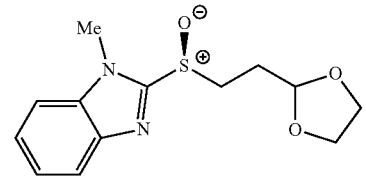  72% yield, 95% ee |
| 2'c 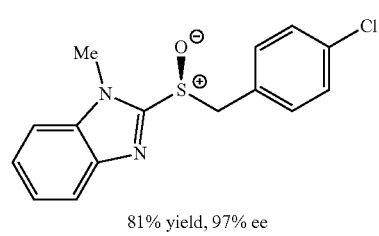  81% yield, 97% ee | 2'i 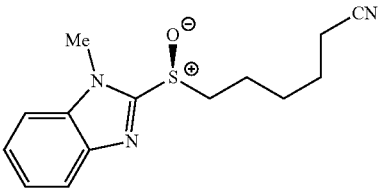  71% yield, 82% ee |
| 2'd 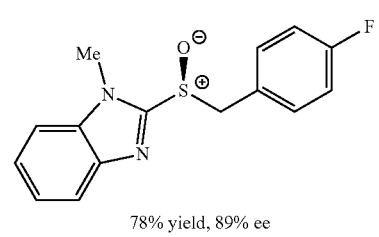  78% yield, 89% ee | 2'j 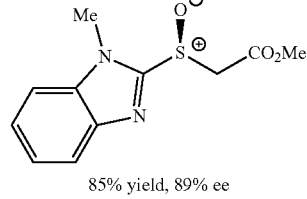  85% yield, 89% ee |
| 2'e 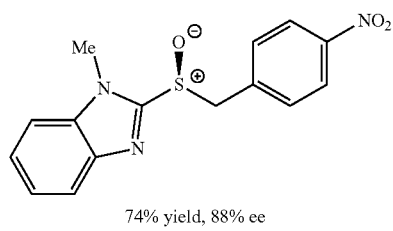  74% yield, 88% ee | 2'k 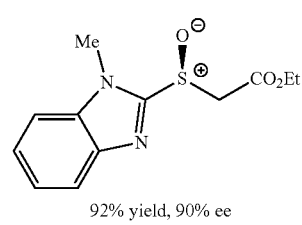  92% yield, 90% ee |
| 2'f 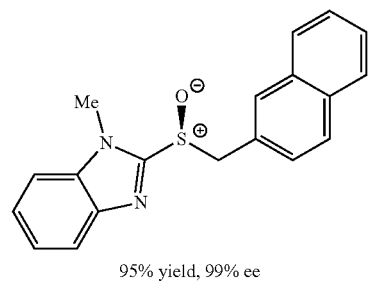  95% yield, 99% ee | 2'l 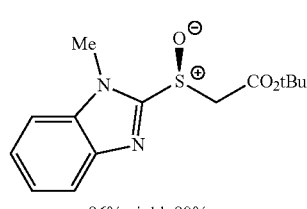  86% yield, 80% ee |
| | 2'm 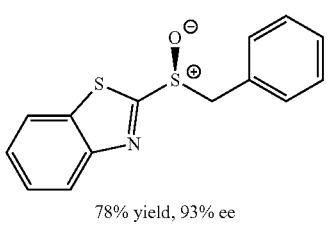  78% yield, 93% ee |

2'n

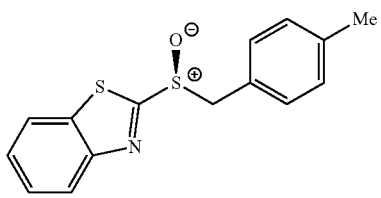

70% yield, 90% ee

2'o

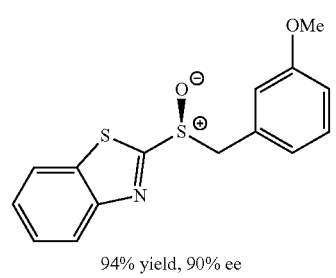

94% yield, 90% ee

2'p[a]

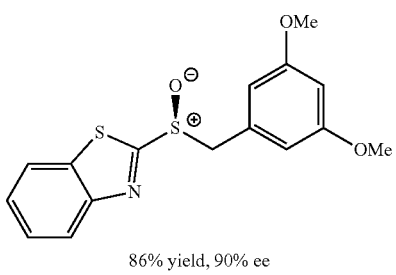

86% yield, 90% ee

2'q

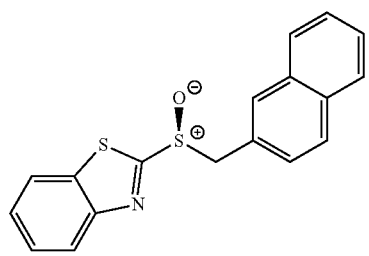

85% yield, 92% ee

2'r[a]

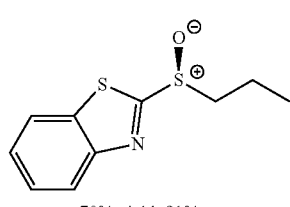

70% yield, 91% ee

2's[a,b]

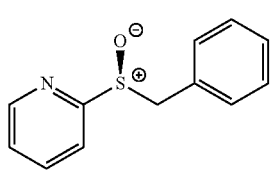

76% yield, 80% ee

2't[a,c]

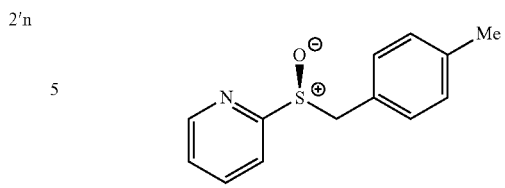

96% yield, 85% ee

2'u[a,b]

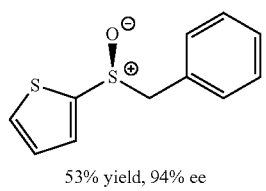

53% yield, 94% ee

The substrate scope of benzimidazole-derived sulfides was examined (Scheme 1, 2'a-2'i).

The benzimidazole group does not seem to act as a ligand and inhibit the reaction. Both electron donating and electron withdrawing substitutions on the benzyl group worked well, affording the corresponding sulfoxidation products in good to excellent yields with good levels of enantioselectivities. The oxidation ability of the catalyst is able to override even highly electron withdrawing group such as pentafluorobenzyl (Scheme 1, 2'g). Besides benzyl groups, simple alkyl groups or esters are also tolerated in this reaction (2'h-l). Other heterocyclic systems such as benzothiazole (2'm-r), pyridine (2's-t) and thiophene (2'u) also worked well providing products with excellent ee values. However, thiophene heterocyclic sulfides gave lower yields with significant amount of sulfone detected.

The reaction was scaled up to gram scale (3.5 mmol) to give 2'q in 91% yield and 92% ee.

Determination of the Absolute Configuration by X-Ray Crystallography.

FIGS. 9A-E depict ORTEP diagrams showing X-ray crystal structure of products (S)-2'a, (S)-2'b, (S)-2'c, (S)-2'q and (S)-2'm respectively The following sulfoxide products were made from their reduced forms (2a-2u) via General Procedure 1, unless otherwise stated.

2'a

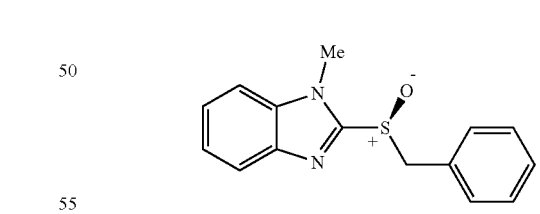

(S)-2-(benzylsulfinyl)-1-methyl-1H-benzo[d]imidazole (2'a)

96% yield; white solid; $^1$H NMR (400 MHz, CDCl$_3$) δ 7.87-7.82 (m, 1H), 7.38-7.35 (m, 2H), 7.32-7.26 (m, 2H), 7.21 (td, J=10.4, 4.7 Hz, 2H), 7.03 (dd, 2H), 4.64 (d, J=12.9 Hz, 1H), 4.50 (d, J=12.9 Hz, 1H), 3.45 (s, 3H); $^{13}$C NMR (101 MHz, CDCl$_3$) δ 150.01, 141.54, 136.47, 130.61, 128.89, 128.77, 124.68, 123.77, 120.59, 109.83, 60.96, 29.97; HRMS (ESI) calcd for C$_{15}$H$_{14}$N$_2$OS m/z [M+H]$^+$:

271.0905; found: 271.0904; $[\alpha]_D^{22}$=−29.16 (c 3.8, CH$_2$Cl$_2$); HPLC analysis: Chiralcel OJ-H (Hex/IPA=70/30, 1.0 mL/min, 254 nm, 22° C.), 17.1, 29.0 (major) min, 92% ee.

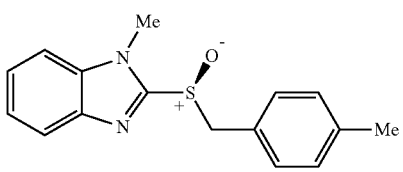

(S)-1-methyl-2-((4-methylbenzyl)sulfinyl)-1H-benzo[d]imidazole (2'b)

94% yield; white solid; $^1$H NMR (400 MHz, CDCl$_3$) δ 7.89-7.78 (m, 1H), 7.38-7.33 (m, 2H), 7.32-7.27 (m, 1H), 7.03 (d, J=7.9 Hz, 2H), 6.93 (d, J=8.0 Hz, 2H), 4.62 (d, J=12.9 Hz, 1H), 4.45 (d, J=12.9 Hz, 1H), 3.49 (s, 3H), 2.30 (s, 3H); $^{13}$C NMR (101 MHz, CDCl$_3$) δ 150.38, 142.01, 138.80, 136.58, 130.50, 129.45, 125.73, 124.51, 123.53, 120.78, 109.78, 60.62, 30.03, 21.27; HRMS (ESI) calcd for C$_{16}$H$_{16}$N$_2$OS m/z [M+H]$^+$: 285.1062; found: 285.1056; $[\alpha]_D^{22}$=−29.41 (c 2.2, CH$_2$Cl$_2$); HPLC analysis: Daicel Corporation IB3 (Hex/IPA=70/30, 1.0 mL/min, 254 nm, 22° C.), 8.4, 15.4 (major) min, 94% ee.

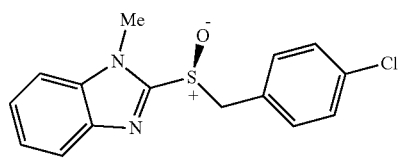

(S)-2-((4-chlorobenzyl)sulfinyl)-1-methyl-1H-benzo[d]imidazole (2'c)

81% yield; white solid; $^1$H NMR (400 MHz, CDCl$_3$) δ 7.82 (dd, J=8.0, 6.6 Hz, 1H), 7.36 (qd, J=12.8, 8.0 Hz, 3H), 7.22 (d, J=8.3 Hz, 2H), 7.01 (d, J=8.3 Hz, 2H), 4.63 (d, J=13.0 Hz, 1H), 4.47 (d, J=13.0 Hz, 1H), 3.59 (s, 3H); $^{13}$C NMR (101 MHz, CDCl$_3$) δ 149.73, 141.95, 136.67, 135.11, 131.96, 128.97, 127.55, 124.75, 123.74, 120.80, 109.88, 59.90, 30.23; HRMS (ESI) calcd for C$_{15}$H$_{13}$ClN$_2$OS m/z [M+H]*: 305.0515; found: 305.0518; $[\alpha]_D^{22}$=−41.21 (c 3.2, CH$_2$Cl$_2$); HPLC analysis: Daicel Corporation IB3 (Hex/IPA=70/30, 1.0 mL/min, 254 nm, 22° C.), 9.3, 30.4 (major) min, 97% ee.

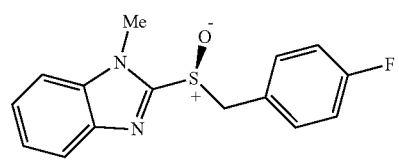

(S)-2-((4-fluorobenzyl)sulfinyl)-1-methyl-1H-benzo[d]imidazole (2'd)

78% yield; white solid; $^1$H NMR (400 MHz, CDCl$_3$) δ 7.87-7.78 (m, 1H), 7.43-7.29 (m, 3H), 7.04 (dd, J=8.4, 5.5 Hz, 2H), 6.91 (t, J=8.6 Hz, 2H), 4.60 (dd, J=30.8, 13.2 Hz, 2H), 3.56 (s, 3H); $^{13}$C NMR (101 MHz, CDCl$_3$) δ 164.47, 162.00, 149.54, 140.37, 136.17, 132.38, 132.30, 125.06, 124.75, 124.71, 124.30, 120.10, 115.91, 115.70, 110.00, 59.95, 30.23; HRMS (ESI) calcd for C$_{15}$H$_{13}$FN$_2$OS m/z [M+H]$^+$: 289.0811; found: 289.0808; $[\alpha]_D^{22}$=−33.38 (c 4.3, CH$_2$Cl$_2$); HPLC analysis: Daicel Corporation IB3 (Hex/IPA=70/30, 1.0 mL/min, 254 nm, 22° C.), 8.9, 29.7 (major) min, 88% ee.

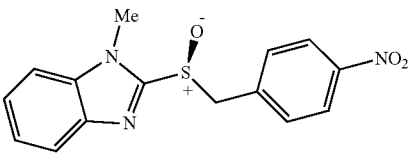

(S)-1-methyl-2-((4-nitrobenzyl)sulfinyl)-1H-benzo[d]imidazole (2'e)

74% yield; yellow solid; $^1$H NMR (400 MHz, CDCl$_3$) δ 8.10 (d, J=8.3 Hz, 1H), 7.82 (d, J=7.4 Hz, 1H), 7.60-7.27 (m, 2H), 4.72 (dd, J=42.3, 12.9 Hz, 1H), 3.69 (s, 1H); $^{13}$C NMR (101 MHz, CDCl$_3$) δ 149.17, 148.18, 141.87, 136.73, 136.60, 131.66, 124.99, 123.91, 123.72, 120.84, 109.96, 59.48, 30.46; HRMS (ESI) calcd for C$_{15}$H$_{13}$N$_3$O$_3$S m/z [M+H]$^+$: 316.0756; found: 316.0761; $[\alpha]_D^{22}$=−213.88 (c 2.3, CH$_2$Cl$_2$); HPLC analysis: Daicel Corporation IA3 (Hex/IPA=70/30, 1.0 mL/min, 254 nm, 22° C.), 14.3, 25.0 (major) min, 88% ee.

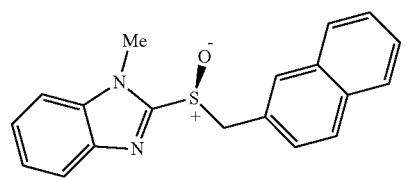

(S)-1-methyl-2-((naphthalen-2-ylmethyl)sulfinyl)-1H-benzo[d]imidazole (2'f)

95% yield; white solid; $^1$H NMR (400 MHz, CDCl$_3$) δ 7.92-7.85 (m, 1H), 7.77 (d, J=7.8 Hz, 1H), 7.66 (d, J=8.4 Hz, 1H), 7.62 (dd, 1H), 7.58 (s, 1H), 7.50-7.34 (m, 4H), 7.23-7.17 (m, 1H), 7.06 (dd, J=8.4, 1.7 Hz, 1H), 4.82 (d, J=12.9 Hz, 1H), 4.69 (d, J=12.9 Hz, 1H), 3.35 (s, 3H); $^{13}$C NMR (101 MHz, CDCl$_3$) δ 149.98, 141.18, 136.34, 133.09, 133.08, 130.23, 128.35, 127.90, 127.65, 127.51, 126.67, 126.54, 126.18, 124.70, 123.83, 120.40, 109.79, 61.21, 30.00; HRMS (ESI) calcd for C$_{19}$H$_{16}$N$_2$OS m/z [M+H]*: 321.1062; found: 321.1062; $[\alpha]_D^{22}$=−222.58 (c 2.2, CH$_2$Cl$_2$); HPLC analysis: Daicel Corporation IB3 (Hex/IPA=70/30, 1.0 mL/min, 254 nm, 22° C.), 10.7, 38.0 (major) min, 99% ee.

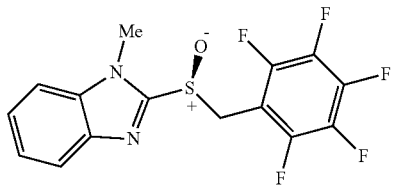

(S)-1-methyl-2-(((perfluorophenyl)methyl)sulfinyl)-1H-benzo[d]imidazole (2'g)

84% yield; white solid; $^1$H NMR (400 MHz, CDCl$_3$) δ 7.80 (d, J=8.1 Hz, 1H), 7.48-7.33 (m, 3H), 4.88 (d, J=13.2 Hz, 1H), 4.71 (d, J=13.1 Hz, 1H), 4.09 (s, 3H); $^{13}$C NMR (101 MHz, CDCl$_3$) δ 149.60, 141.96, 137.04, 125.30, 123.95, 121.11, 109.99, 47.47, 30.92; HRMS (ESI) calcd for C$_{15}$H$_9$F$_5$N$_2$OS m/z [M+H]*: 361.0434; found: 361.0435; [α]$_D^{12}$=−141.82 (c 2.2, CH$_2$Cl$_2$); HPLC analysis: Daicel Corporation IB3 (Hex/IPA=70/30, 1.0 mL/min, 254 nm, 22° C.), 10.2, 15.6 (major) min, 92% ee.

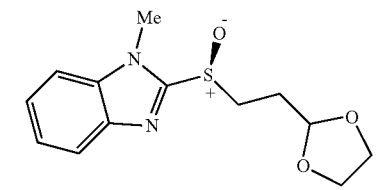

(S)-2-((2-(1,3-dioxolan-2-yl)ethyl)sulfinyl)-1-methyl-1H-benzo[d]imidazole (2'h)

72% yield; colorless oil; $^1$H NMR (400 MHz, CDCl$_3$) δ 7.81 (d, J=7.9 Hz, 1H), 7.45-7.36 (m, 2H), 7.34 (ddd, J=8.3, 6.6, 1.8 Hz, 1H), 5.04 (t, J=3.9 Hz, 1H), 4.11 (s, 3H), 4.01-3.92 (m, 2H), 3.89-3.80 (m, 2H), 3.59 (ddd, J=8.3, 6.8, 1.8 Hz, 2H), 2.28 (dddd, J=14.8, 8.0, 6.9, 4.0 Hz, 1H), 2.14 (dddd, J=9.9, 7.5, 6.6, 3.5 Hz, 1H); $^{13}$C NMR (101 MHz, CDCl$_3$) δ 151.13, 141.62, 136.73, 124.84, 123.71, 120.85, 109.98, 102.46, 65.26, 47.86, 31.01, 26.58; HRMS (ESI) calcd for C$_{13}$H$_{16}$N$_2$O$_3$S m/z [M+H]$^+$: 281.0960; found: 281.0959; [α]$_D^{22}$=+8.45 (c 0.9, CHCl$_3$); HPLC analysis: Daicel Corporation IB3 (Hex/IPA=70/30, 1.0 mL/min, 254 nm, 22° C.), 15.1, 19.3 (major) min, 95% ee.

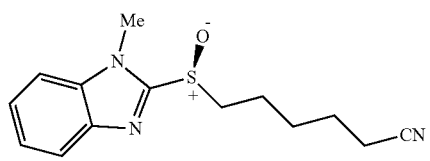

(S)-6-((I-methyl-1H-benzo[d]imidazol-2-yl)sulfinyl)hexanenitrile (2'i)

71% yield; colorless oil; $^1$H NMR (400 MHz, CDCl$_3$) δ 7.84-7.78 (m, 1H), 7.47-7.39 (m, 2H), 7.37 (ddd, 1H), 4.14 (s, 3H), 3.57 (ddd, J=13.2, 9.4, 5.6 Hz, 1H), 3.45 (ddd, J=13.2, 9.5, 6.3 Hz, 1H), 2.36 (t, J=6.8 Hz, 2H), 2.05-1.81 (m, 2H), 1.79-1.63 (m, 4H); $^{13}$C NMR (101 MHz, CDCl$_3$) δ 150.80, 141.27, 136.74, 125.02, 123.96, 120.68, 119.40, 110.09, 52.84, 31.13, 27.71, 25.06, 21.66, 17.05; HRMS (ESI) calcd for C$_{14}$H$_{17}$N$_3$OS m/z [M+Na]$^+$: 298.0990; found: 298.0996; [α]$_D^{22}$=+7.71 (c 0.7, CHCl$_3$); HPLC analysis: Daicel Corporation IB3 (Hex/IPA=70/30, 1.0 mL/min, 254 nm, 22° C.), 24.6, 41.0 (major) min, 82% ee.

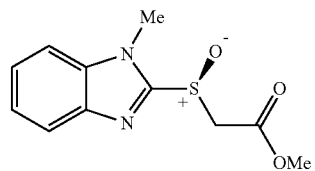

(S)-methyl-2-((1-methyl-1H-benzo[d]imidazol-2-yl)sulfinyl)acetate (2'j)

85% yield; white solid; $^1$H NMR (400 MHz, CDCl$_3$) δ 7.84-7.77 (m, 1H), 7.46-7.39 (m, 2H), 7.36 (ddd, J=8.3, 6.4, 2.0 Hz, 1H), 4.69 (d, J=15.1 Hz, 1H), 4.44 (d, J=15.1 Hz, 1H), 4.11 (s, 3H), 3.74 (s, 3H); $^{13}$C NMR (101 MHz, CDCl$_3$) δ 165.45, 165.43, 150.83, 141.38, 136.67, 125.25, 125.18, 123.97, 121.01, 120.92, 110.20, 57.21, 53.12, 31.04; HRMS (ESI) calcd for C$_{11}$H$_{12}$N$_2$O$_3$S m/z [M+H]$^+$: 253.0647; found: 253.0645; [α]$_D^{22}$=+5.25 (c 1.2, CH$_2$Cl$_2$); HPLC analysis: Daicel Corporation IB3 (Hex/IPA=70/30, 1.0 mL/min, 254 nm, 22° C.), 15.6, 22.0 (major) min, 89% ee.

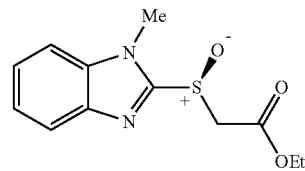

(S)-ethyl-2-((1-methyl-1H-benzo[d]imidazol-2-yl)sulfinyl)acetate (2'k)

92% yield; white solid; $^1$H NMR (400 MHz, CDCl$_3$) δ 7.80 (d, J=8.0 Hz, 1H), 7.46-7.38 (m, 2H), 7.35 (ddd, J=8.2, 6.5, 1.9 Hz, 1H), 4.65 (t, J=14.3 Hz, 1H), 4.41 (d, J=15.0 Hz, 1H), 4.18 (q, J=7.1 Hz, 2H), 4.10 (s, 3H), 1.21 (t, J=7.1 Hz, 3H); $^{13}$C NMR (101 MHz, CDCl$_3$) δ 164.92, 150.95, 141.46, 136.66, 125.11, 123.89, 120.93, 110.16, 62.39, 57.45, 31.01, 14.05; HRMS (ESI) calcd for C$_{12}$H$_{14}$N$_2$O$_3$S m/z [M+H]$^+$: 267.0803; found: 267.0807; [α]$_D^{22}$=+4.62 (c 1.2, CH$_2$Cl$_2$); HPLC analysis: Daicel Corporation IB3 (Hex/IPA=70/30, 1.0 mL/min, 254 nm, 22° C.), 11.4, 16.6 (major) min, 90% ee.

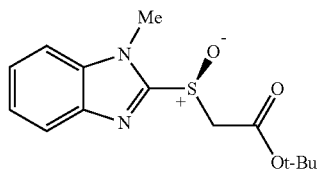

2'l

(S)-tert-butyl-2-((1-methyl-1H-benzo[d]imidazol-2-yl)sulfinyl)acetate (2'l)

86% yield; white solid; $^1$H NMR (400 MHz, CDCl$_3$) δ 7.83-7.75 (m, 1H), 7.46-7.38 (m, 2H), 7.35 (ddd, J=8.3, 6.5, 1.9 Hz, 1H), 4.57 (d, J=14.8 Hz, 1H), 4.34 (d, J=14.8 Hz, 1H), 4.11 (s, 3H), 1.39 (s, 9H); $^{13}$C NMR (101 MHz, CDCl$_3$) δ 163.93, 151.09, 141.45, 136.64, 125.06, 123.86, 120.89, 110.13, 83.86, 58.46, 31.01, 27.97; HRMS (ESI) calcd for C$_{14}$H$_{18}$N$_2$O$_3$S m/z [M+Na]$^+$: 317.0936; found: 317.0937; [α]$_D^{22}$=+13.78 (c 1.1, CHCl$_3$); HPLC analysis: Daicel Corporation IB3 (Hex/IPA=70/30, 1.0 mL/min, 254 nm, 22° C.), 7.3, 8.6 (major) min, 80% ee.

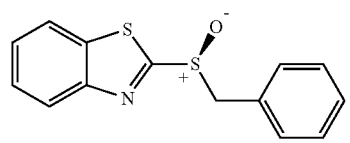

2'm

(S)-2-(benzylsulfinyl)benzo[d]thiazole (2'm)

78% yield; white solid; $^1$H NMR (400 MHz, CDCl$_3$) δ 8.09 (d, J=8.2 Hz, 1H), 7.93 (d, J=8.1 Hz, 1H), 7.57 (t, J=7.3 Hz, 1H), 7.47 (t, J=7.6 Hz, 1H), 7.34-7.23 (m, 3H), 7.17 (d, J=6.8 Hz, 2H), 4.51 (d, J=13.1 Hz, 1H), 4.33 (d, J=13.1 Hz, 1H); $^{13}$C NMR (101 MHz, CDCl$_3$) δ 176.99, 153.74, 136.04, 130.47, 128.75, 128.71, 128.39, 126.93, 126.16, 123.93, 122.26, 118.61, 62.85; HRMS (ESI) calcd for C$_{14}$H$_{11}$NOS$_2$ m/z [M+H]$^+$: 274.0360; found: 274.0356; [α]$_D^{12}$=−47.99 (c 3.3, CH$_2$Cl$_2$); HPLC analysis: Chiralcel OD-H (Hex/IPA=90/10, 1.0 mL/min, 254 nm, 22° C.), 13.4 (major), 16.4 min, 93% ee.

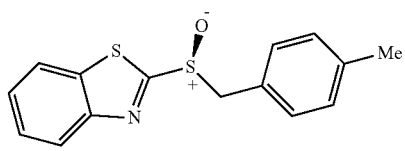

2'n

(S)-2-((4-methylbenzyl)sulfinyl)benzo[d]thiazole (2'n)

70% yield; white solid; $^1$H NMR (400 MHz, CDCl$_3$) δ 8.10 (d, J=8.2 Hz, 1H), 7.95 (d, J=8.0 Hz, 1H), 7.57 (ddd, J=8.3, 7.3, 1.2 Hz, 1H), 7.48 (ddd, 1H), 7.15-7.01 (m, 4H), 4.48 (d, J=13.1 Hz, 1H), 4.31 (d, J=13.1 Hz, 1H), 2.31 (s, 3H); $^{13}$C NMR (101 MHz, CDCl$_3$) δ 177.27, 153.84, 138.80, 136.13, 130.46, 129.56, 127.00, 126.22, 125.37, 124.00, 122.37, 62.82, 21.32; HRMS (ESI) calcd for C$_{15}$H$_{13}$NOS$_2$ m/z [M+Na]$^+$: 310.0336; found: 310.0333; [α]$_D^{22}$=−74.52 (c 1.6, CH$_2$Cl$_2$); HPLC analysis: Chiralcel OD-H (Hex/IPA=90/10, 1.0 mL/min, 254 nm, 22° C.), 12.4 (major), 15.9 min, 90% ee.

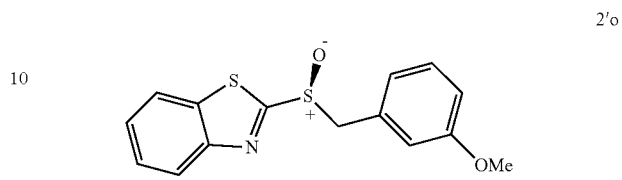

2'o

(S)-2-((3-methoxybenzyl)sulfinyl)benzo[d]thiazole (2'o)

94% yield; white solid; $^1$H NMR (400 MHz, CDCl$_3$) δ 8.10 (d, J=8.2 Hz, 1H), 7.95 (d, J=8.1 Hz, 1H), 7.57 (ddd, 1H), 7.48 (ddd, 1H), 7.18 (t, J=7.9 Hz, 1H), 6.84 (dd, J=8.2, 2.3 Hz, 1H), 6.79 (d, J=7.5 Hz, 1H), 6.66 (d, J=1.8 Hz, 1H), 4.48 (d, J=13.1 Hz, 1H), 4.30 (d, J=13.1 Hz, 1H), 3.60 (s, 3H); $^{13}$C NMR (101 MHz, CDCl$_3$) δ 177.19, 159.82, 153.84, 136.17, 129.86, 129.82, 127.05, 126.29, 124.00, 122.95, 122.39, 115.26, 115.21, 63.17, 55.18, 25.48; HRMS (ESI) calcd for C$_{15}$H$_{13}$NO$_2$S$_2$ m/z [M+H]$^+$: 304.0466; found: 304.0467; [α]$_D^{22}$=−59.08 (c 3.1, CH$_2$Cl$_2$); HPLC analysis: Daicel Corporation IB3 (Hex/IPA=70/30, 1.0 mL/min, 254 nm, 22° C.), 7.3 (major), 7.6 min, 91% ee.

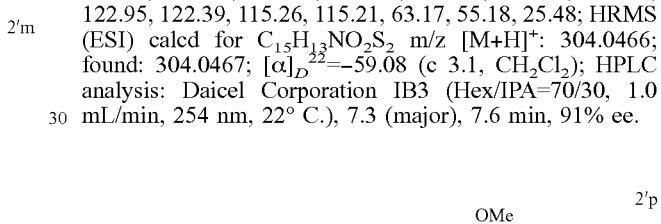

2'p

(S)-2-((3,5-dimethoxybenzyl)sulfinyl)benzo[d]thiazole (2'p)

86% yield; white solid; $^1$H NMR (400 MHz, CDCl$_3$) δ 8.09 (d, J=8.2 Hz, 1H), 7.96 (d, J=8.1 Hz, 1H), 7.56 (ddd, 1H), 7.48 (ddd, J=11.2, 4.1 Hz, 1H), 6.41-6.35 (m, 1H), 6.31 (d, J=2.2 Hz, 2H), 4.43 (d, J=13.0 Hz, 1H), 4.26 (d, J=13.0 Hz, 1H), 3.60 (s, 6H); $^{13}$C NMR (101 MHz, CDCl$_3$) δ 177.30, 160.97, 153.85, 136.20, 130.55, 127.07, 126.32, 124.00, 122.41, 108.22, 101.57, 63.57, 55.35; HRMS (ESI) calcd for C$_{16}$H$_{15}$NO$_3$S$_2$ m/z [M+H]$^+$: 334.0572; found: 334.0574; [α]$_D^{22}$f=−166.21 (c 3.1, CHCl$_3$); HPLC analysis: Chiralcel OD-H (Hex/IPA=90/10, 0.5 mL/min, 254 nm, 22° C.), 37.8 (major), 42.4 min, 92% ee.

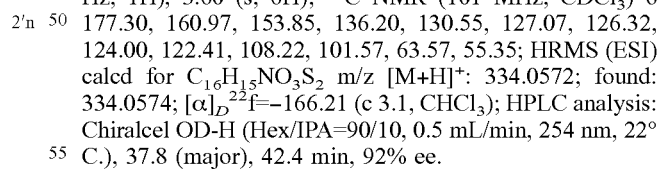

2'q

(S)-2-((naphthalen-2-ylmethyl)sulfinyl)benzo[d]thiazole (2'q)

85% yield; white solid; $^1$H NMR (400 MHz, CDCl$_3$) δ 8.12 (d, J=8.2 Hz, 1H), 7.90 (d, J=8.1 Hz, 1H), 7.83-7.76 (m, 1H), 7.72 (dd, J=8.7, 4.9 Hz, 3H), 7.58 (ddd, 1H), 7.51-7.41 (m, 3H), 7.25 (dd, J=8.5, 1.7 Hz, 1H), 4.68 (d, J=13.1 Hz, 1H), 4.50 (d, J=13.1 Hz, 1H); $^{13}$C NMR (101 MHz, CDCl$_3$) δ 177.12, 153.87, 136.14, 133.27, 133.26, 130.36, 128.59, 128.10, 127.79, 127.58, 127.05, 126.66, 126.51, 126.26, 124.02, 122.38, 63.41.; HRMS (ESI) calcd for C$_{18}$H$_{13}$NOS$_2$ m/z [M+H]$^+$: 324.0517; found: 324.0523; [α]$_D^{22}$=−78.47 (c 2.2, CH$_2$Cl$_2$); HPLC analysis: Chiralcel AS-H (Hex/IPA=90/10, 1.0 mL/min, 254 nm, 22° C.), 36.1, 43.4 (major) min, 91% ee.

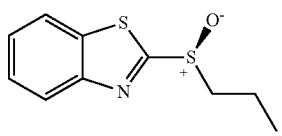

(S)-2-(propylsulfinyl)benzo[d]thiazole (2'r)

70% yield; colorless oil; $^1$H NMR (400 MHz, CDCl$_3$) δ 8.04 (d, J=8.2 Hz, 1H), 7.98 (d, J=8.0 Hz, 1H), 7.54 (t, J=7.7 Hz, 1H), 7.47 (t, J=7.6 Hz, 1H), 3.26-3.11 (m, 2H), 1.99 (tq, J=14.8, 7.4 Hz, 1H), 1.76 (tq, 1H), 1.08 (t, J=7.4 Hz, 3H); $^{13}$C NMR (101 MHz, CDCl$_3$) δ 177.86, 153.99, 136.02, 126.99, 126.21, 123.97, 122.36, 116.21, 58.61, 15.53, 13.24; HRMS (ESI) calcd for C$_{10}$H$_{11}$NOS$_2$ m/z [M+Na]$^+$: 248.0180; found: 248.0176; [α]$_D^{22}$=−1.15 (c 2.0, CH$_2$Cl$_2$); HPLC analysis: Chiralcel OB-H (Hex/IPA=90/10, 1.0 mL/min, 254 nm, 22° C.), 12.3 (major), 14.5 min, 91% ee.

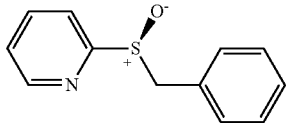

(S)-2-(benzylsulfinyl)pyridine (2's)

76% yield; white solid; $^1$H NMR (400 MHz, CDCl$_3$) δ 8.69 (d, J=4.3 Hz, 1H), 7.80 (td, J=7.7, 1.7 Hz, 1H), 7.63 (d, J=7.9 Hz, 1H), 7.37 (ddd, J=7.6, 4.7, 1.1 Hz, 1H), 7.31-7.21 (m, 3H), 7.04 (dd, J=7.7, 1.6 Hz, 2H), 4.40 (d, J=13.1 Hz, 1H), 4.10 (d, J=13.1 Hz, 1H); $^{13}$C NMR (101 MHz, CDCl$_3$) δ 163.64, 149.11, 137.86, 130.27, 129.31, 128.31, 128.17, 124.67, 120.73, 59.97; HRMS (ESI) calcd for C$_{12}$H$_{11}$NOS m/z [M+H]$^+$: 218.0640; found: 218.0639; [α]$_D^{22}$=−205.63 (c 2.6, CHCl$_3$); HPLC analysis: Chiralcel OD-H (Hex/IPA=90/10, 1.0 mL/min, 254 nm, 22° C.), 17.7 (major), 21.9 min, 80% ee.

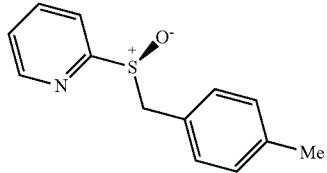

(S)-2-((4-methylbenzyl)sulfinyl)pyridine (2't)

96% yield; white solid; $^1$H NMR (400 MHz, CDCl$_3$) δ 8.71-8.51 (m, 1H), 7.78 (td, J=7.7, 1.7 Hz, 1H), 7.62 (dt, J=7.9, 0.9 Hz, 1H), 7.33 (ddd, J=7.6, 4.7, 1.2 Hz, 1H), 7.02 (d, J=7.8 Hz, 2H), 6.89 (d, J=8.0 Hz, 2H), 4.33 (d, J=13.1 Hz, 1H), 4.03 (d, J=13.1 Hz, 1H), 2.28 (s, 3H); $^{13}$C NMR (101 MHz, CDCl$_3$) δ 163.90, 149.26, 138.08, 137.84, 130.25, 129.14, 126.26, 124.67, 120.77, 59.87, 21.24; HRMS (ESI) calcd for C$_{13}$H$_{13}$NOS m/z [M+Na]$^+$: 254.0616; found: 254.0620; [α]$_D^{22}$=−253.06 (c 3.4, CHCl$_3$); HPLC analysis: Chiralcel OB-H (Hex/IPA=90/10, 0.5 mL/min, 254 nm, 22° C.), 21.7 (major), 25.5 min, 85% ee.

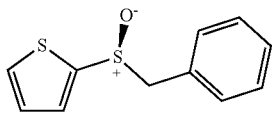

(S)-2-(benzylsulfinyl)thiophene (2'u)

53% yield; white solid; $^1$H NMR (400 MHz, CDCl$_3$) δ 7.62 (d, J=4.9 Hz, 1H), 7.32-7.24 (m, 3H), 7.13 (t, J=4.1 Hz, 1H), 7.08 (dd, J=7.2, 1.9 Hz, 2H), 7.05-6.98 (m, 1H), 4.36 (d, J=12.4 Hz, 1H), 4.15 (d, J=12.4 Hz, 1H); $^{13}$C NMR (101 MHz, CDCl$_3$) δ 144.93, 131.19, 130.33, 129.89, 129.34, 128.80, 128.58, 127.28, 65.14; HRMS (ESI) calcd for C$_{11}$H$_{10}$OS$_2$ m/z [M+H]$^+$: 245.0071; found: 245.0071; [α]$_D^{22}$=+73.96 (c 1.0, CHCl$_3$); HPLC analysis: Chiralcel OD-H (Hex/IPA=90/10, 1.0 mL/min, 254 nm, 22° C.), 18.5, 25.0 (major) min, 95% ee.

Example 4: Enantioselective Synthesis and Characterization of (S)-Lansoprazole

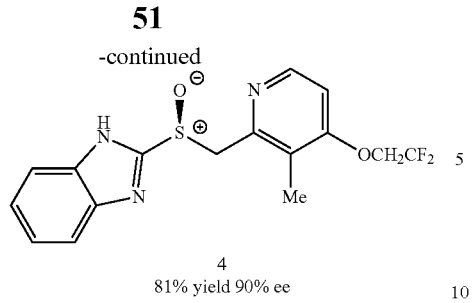

4
81% yield 90% ee

The established strategy was also successfully applied to the preparation of (S)-Lansoprazole, a commercial proton-pump inhibitor.

Synthetic Protocol:

In a 25 mL round-bottomed flask, sulfides 3 (0.2 mmol, 1.0 equiv), bisguanidinium chloride (0.004 mmol, 0.02 equiv), silver tungstate oxide (0.004 mmol, 0.02 equiv), ammonium phosphate monobasic (0.02 mmol, 0.1 equiv) and 8 mL solvent were added. Then lower the solution to the presupposed temperature in a constant incubator. After stabilizing, $H_2O_2$(1.05 equiv, 35% w/w) was injected in one portion into the system. The mixture was stirred for 48 hours, and the termination of reaction was monitored by TLC. The resulting suspension was quenched by saturated $Na_2S_2O_3$. $NaHCO_3$ was used to wash, and then EtOAc (0.5 mL×3) was used for extraction, and the organic layers were combined and dried over anhydrous $Na_2SO_4$. The organic solvent was removed in rotary evaporator (the water-bathing temperature is under 38° C.), and the residues were purified by chromatography on silica gel to afford the desired products.

(S)-2-(((3-methyl-4-(2,2,2-trifluoroethoxy)pyridin-2-yl)methyl)sulfinyl)-1H-benzo[d]imidazole or (S)-Lansoprazole (4)

81% yield; white solid; $^1$H NMR (400 MHz, Acetone) δ 8.38 (d, J=5.6 Hz, 1H), 7.75 (d, J=3.1 Hz, 2H), 7.40 (dd, J=6.1, 3.2 Hz, 2H), 7.13 (d, J=5.7 Hz, 1H), 4.93-4.90 (AB-system, J=13.5 Hz, 2H), 4.89-4.84 (q, J=7.8 Hz, 2H), 2.33 (s, 3H); $^{13}$C NMR (101 MHz, Acetone) δ 162.69, 155.37, 152.14, 149.15, 126.02, 124.16, 123.71, 123.27, 107.52, 66.50, 66.15, 65.80, 65.44, 61.80, 61.75, 11.07; HRMS (ESI) calcd for $C_{16}H_{14}F_3N_3O_2S$ m/z [M+H]$^+$: 370.0837; found: 370.0838; $[\alpha]_D^{22}$=−253.8 (c 0.5, Acetone); HPLC analysis: Chiralcel OD-H (Hex/IPA=80/20, 0.7 mL/min, 254 nm, 22° C.), 22.9 (major), 33.3 min, 90% ee.

Example 5: Enantioselective Sulfoxidation of Phenyl Sulfides Using Tungstate System Scheme 3: Enantioselective sulfoxidation of phenyl sulfides. [a] Reactions were carried out on 0.2 mmol scale in a solvent mixture of DMC (4.0 mL)/iPr$_2$O (4.0 mL). (DMC = dimethyl carbonate). [b] Reactions were carried out in a solvent mixture of DMC (4.0 mL)/Et$_2$O (4.0 mL).

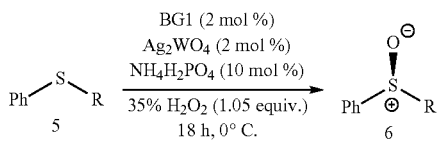

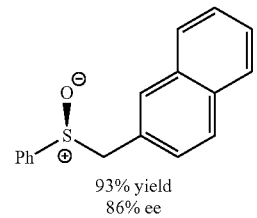

6a[a]

79% yield
90% ee

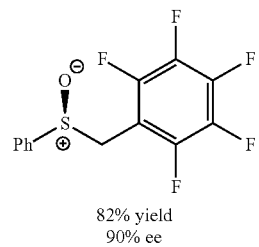

6b[b]

93% yield
86% ee

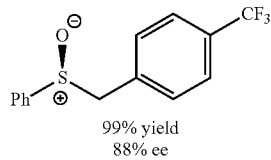

6c[b]

82% yield
90% ee

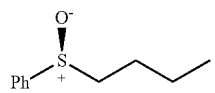

6d[b]

99% yield
88% ee

To further demonstrate the substrate scope of this new method, several conventional substrates containing phenyl sulfide moiety were also tested (Scheme 3). For such substrates, a balance between reaction yields and enantioselectivities was achieved by employing a solvent mixture between dimethyl carbonate (DMC) and ethers. The substrates (5a-5d) that could be tolerated included those with simple alkyl chains to electron-withdrawing aromatic rings.

The following sulfoxide products were made from their reduced forms (5a-5d) via General Procedure 2, unless otherwise stated.

6a

(S)-(butylsulfinyl)benzene (6a)

79% yield; colorless oil; $^1$H NMR (400 MHz, CDCl$_3$) δ 7.63-7.58 (m, 2H), 7.52-7.45 (m, 3H), 2.77 (dt, 2H), 1.79-1.65 (m, 1H), 1.64-1.51 (m, 1H), 1.50-1.34 (m, 2H), 0.89 (t, J=7.3 Hz, 3H); $^{13}$C NMR (101 MHz, CDCl$_3$) δ 143.97, 130.91, 129.18, 124.04, 57.01, 24.13, 21.87, 13.62; HRMS (ESI) calcd for $C_{10}H_{14}OS$ m/z [M+H]$^+$: 183.0844; found: 183.0849; $[\alpha]_D^{22}$=−165.82 (c 0.73, CH$_2$Cl$_2$); HPLC analysis: Chiralcel OB-H (Hex/IPA=50/50, 0.5 mL/min, 254 nm, 22° C.), 9.5 (major), 12.2 min, 90% ee.

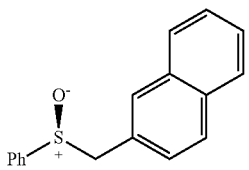

(S)-2-((phenylsulfinyl)methyl)naphthalene (6b)

93% yield; white solid; $^1$H NMR (400 MHz, CDCl$_3$) δ 7.83-7.76 (m, 2H), 7.71 (dd, J=8.6, 5.9 Hz, 2H), 7.50-7.42 (m, 4H), 7.39 (d, J=4.3 Hz, 4H), 7.08 (dd, J=8.4, 1.7 Hz, 1H), 4.25 (d, J=12.6 Hz, 1H), 4.16 (d, J=12.6 Hz, 1H); $^{13}$C NMR (101 MHz, CDCl$_3$) δ 142.88, 133.18, 133.02, 131.30, 129.93, 128.98, 128.23, 127.95, 127.81, 127.75, 126.71, 126.44, 126.41, 124.56, 64.00; HRMS (ESI) calcd for C$_{17}$H$_{14}$OS m/z [M+H]$^+$: 267.0844; found: 267.0850; [α]$_D^{12}$=−41.85 (c 1.3, CH$_2$Cl$_2$); HPLC analysis: Chiralcel OD-H (Hex/IPA=90/10, 1.0 mL/min, 254 nm, 22° C.), 18.7, 22.2 (major) min, 86% ee.

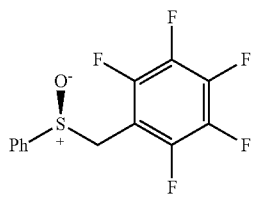

(S)-1,2,3,4,5-pentafluoro-6-((phenylsulfinyl)methyl)benzene (6c)

82% yield; white solid; $^1$H NMR (400 MHz, CDCl$_3$) δ 7.63-7.38 (m, 5H), 4.19 (d, J=13.0 Hz, 1H), 4.09 (d, J=13.0 Hz, 1H); $^{13}$C NMR (101 MHz, CDCl$_3$) δ 142.57, 132.14, 129.45, 124.05, 50.40; HRMS (ESI) calcd for C$_{13}$H$_7$F$_5$OS m/z [M+H]$^+$: 307.0216; found: 307.0221; [α]$_D^{22}$=−102.15 (c 1.5, CH$_2$Cl$_2$); HPLC analysis: Chiralcel OD-H (Hex/IPA=90/10, 1.0 mL/min, 254 nm, 22° C.), 10.7, 12.1 (major) min, 90% ee.

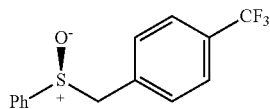

(S)-1-((phenylsulfinyl)methyl)=4(trifluoromethyl)benzene (6d)

99% yield; white solid; $^1$H NMR (400 MHz, CDCl$_3$) δ 7.56-7.30 (m, 7H), 7.07 (d, J=8.0 Hz, 2H), 4.10 (d, J=12.7 Hz, 1H), 4.01 (d, J=12.7 Hz, 1H); $^{13}$C NMR (101 MHz, CDCl$_3$) δ 142.36, 133.18, 131.55, 130.81, 129.15, 125.37, 125.33, 124.39, 62.60; HRMS (ESI) calcd for C$_{14}$H$_{11}$F$_3$OS m/z [M+H]$^+$: 285.0561; found: 285.0555; [α]$_D^{22}$=−88.63 (c 1.5, CH$_2$Cl$_2$); HPLC analysis: Chiralcel OD-H (Hex/IPA=90/10, 1.0 mL/min, 254 nm, 22° C.), 12.7, 14.0 (major) min, 88% ee.

Example 6: Influence of Phosphate Loading

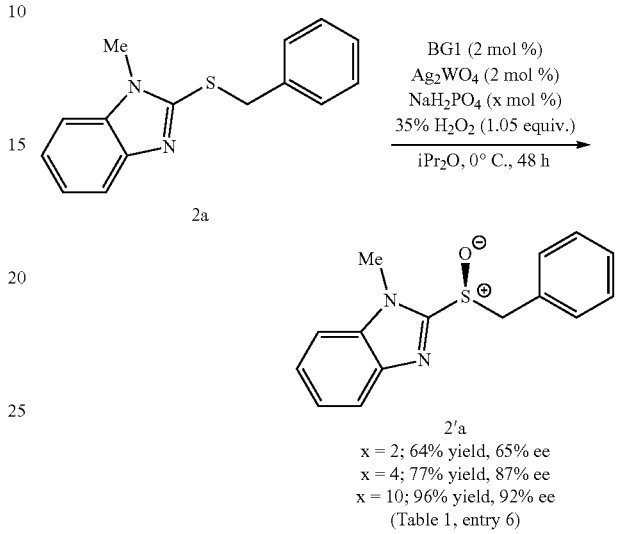

Scheme 4 x = 2; 64% yield, 65% ee
x = 4; 77% yield, 87% ee
x = 10; 96% yield, 92% ee
(Table 1, entry 6)

Synthetic Protocol: General Procedure 1

During optimization of the reaction conditions, it was found that the ratio between Ag$_2$WO$_4$ to NaH$_2$PO$_4$ is crucial in obtaining good yields and enantioselectivities. As shown by Scheme 3, the most significant improvement was achieved when the ratio of phosphate to tungstate reached 2:1.

As the amount of phosphate in this current methodology is in excess over tungstate, it was speculated that the Ishii-Venturello catalyst, [PO$_4${WO(O$_2$)$_2$}$_4$]$^{3-}$, is not the active catalyst in this methodology. When Ag$_2$WO$_4$/NaH$_2$PO$_4$ was replaced with H$_3$PW$_{12}$O$_{40}$ (Keggin's reagent) as in Ishii's protocol, the reaction provided sulfoxides in 40% yield and 30% ee. The search for the active species is further explored in Example 7.

Example 7: Characterization of Tungstate Anion

Ligand coordination or substitution has been previously shown to be an important factor that can influence the catalytic activities of peroxotungstates. Under the current experimental condition, monomeric and oligomeric dihydroxide species i (see FIG. 11) should exist and in the presence of phosphate additive, form substituted phosphate species ii-iv [S. Campestrini, et al., *J. Org. Chem.* 1988, 53, 5721; C. H. Yang, et al., *J. Chem. Soc., Chem. Commun.* 1985, 20, 1425; G. Amato, et al., *J. Mol. Catal.* 1986, 37, 165]. These complexes assume distorted pentagonal bipyramid geometry and obey the 18-electron rule. As a result, coordination of three or more phosphates to the tungstate center can be considered to be unlikely. It is also important to note that due to the short O—O bond distances (1.45 to 1.47 Å) (S. E. Jacobson, R. Tang, F. Mares, *Inorg. Chem.* 1978, 17, 3055) in the peroxo group, the oxygen atoms will most likely lie in the equatorial plane, instead of occupying both axial and equatorial positions in the complex. Based on these premises, the four possible configurations of substituted peroxotungstate species are presented (FIG. 11).

Preparation of Active Species

Figure 1:
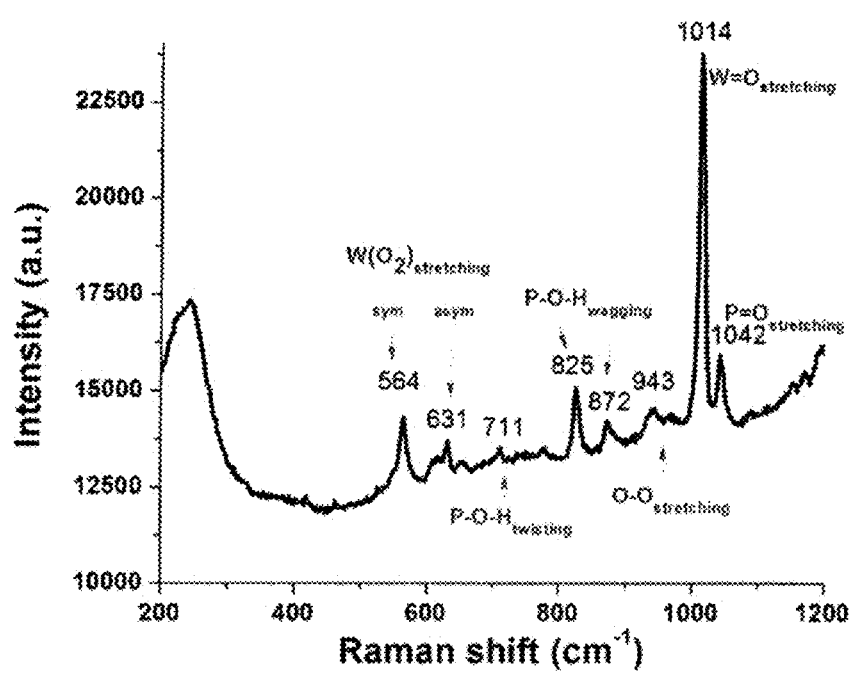

To identify the active species in the tungstate-catalyzed Sulfoxidation, in a 4 mL sample vial, BG-1 (0.01 mmol, 1.0 equiv), tungstate oxide (0.01 mmol, 1.0 equiv), phosphate monobasic (0.05 mmol, 5.0 equiv), hydrogen peroxide (0.1 mmol, 10.0 equiv, 35% w/w) and diethyl ether in a proper amount were added at room temperature and stirred for 6 hours, and filtrate the precipitate. The mixture was blown dry, and then removed of water in vacuo. FIG. 1A shows the Raman spectrum of the active species. Raman setting: 2 mW, 532 laser power, 30 seconds.

Comparison of Experimental and Computed Raman Spectra

The experimental Raman spectra of the active species was compared with predicted Raman spectra of the four possible intermediates (see FIG. 11). Computed Raman spectra were obtained by performing vibrational frequency analysis on stationary points optimized at the B3LYP/B1 level of theory in gas phase, where B1 is a combination of LANL2DZ effective core potential basis set for W and the 6-31g* basis set for remaining atoms.

The peak at 1014 cm$^{-1}$ in experimental Raman spectra (see FIG. 1A) was found to be the peak with the highest intensity, which corresponds to the W=O bond stretching vibrations. Computed Raman spectra showed this peak at 920-1000 cm$^{-1}$ region. Additionally, characteristic bands from W(O$_2$) group appear in 500-600 cm$^{-1}$ region, while bands above 1000 cm$^{-1}$ generally correspond to vibrational modes from phosphate group.

A peak was observed experimentally at 711 cm$^{-1}$, which corresponds to the twisting of P—O—H group in the phosphate ligand (FIG. 1A). This same peak was found only in the computed spectra of P2W (713 cm$^{-1}$) (see FIG. 11D). A more thorough analysis of the P2W structures revealed that intramolecular hydrogen bond interaction between the two phosphate ligands is important for this peak; absence of such interaction will shift the vibrational frequency towards 800 cm$^{-1}$. It is thus proposed that the active anion of this enantioselective sulfoxidation is diphosphatobisperoxotungstate, $[\{PO_2(OH)_2\}_2\{WO(O_2)_2\}]^{2-}$.

Example 8: Computational Studies of Ion-Pair BG1-P2W

Figure 2:
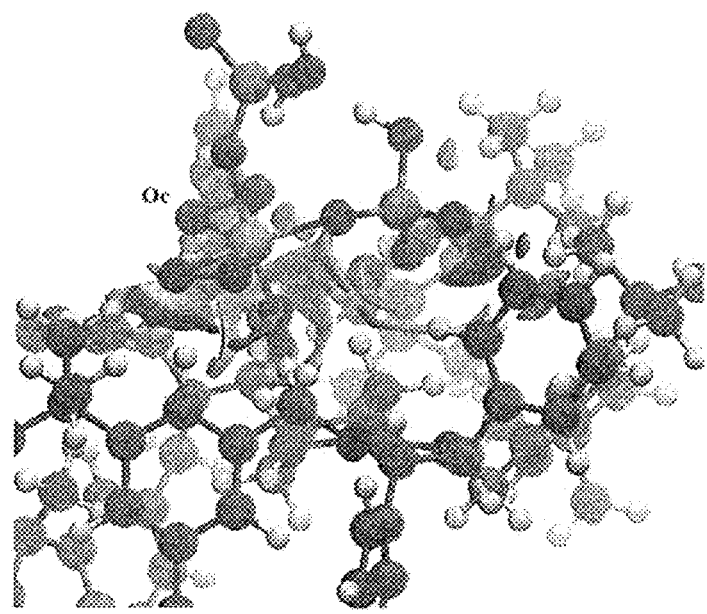
Figure 3:
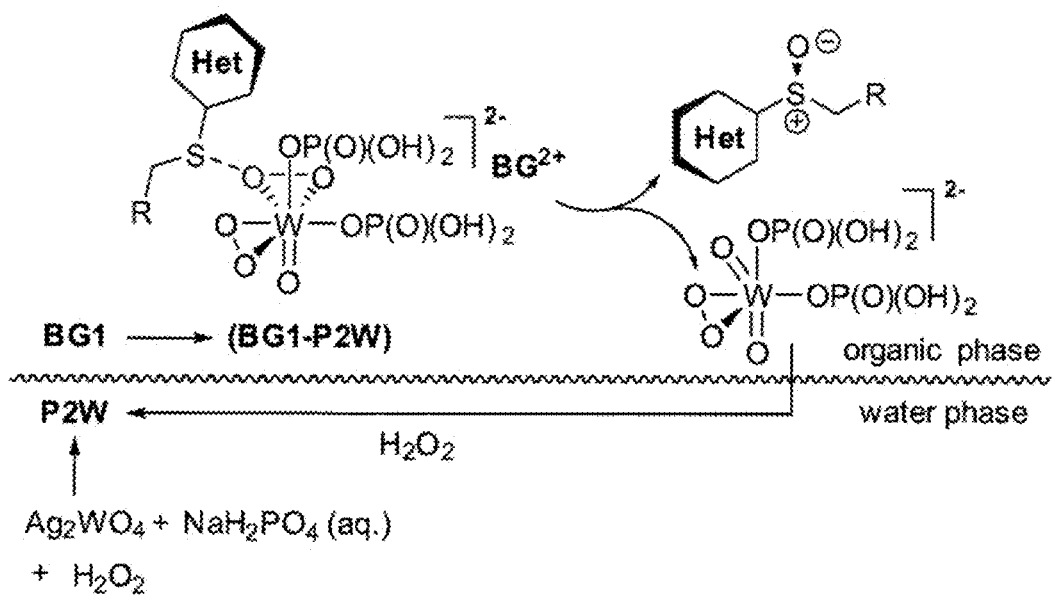
Figure 4:
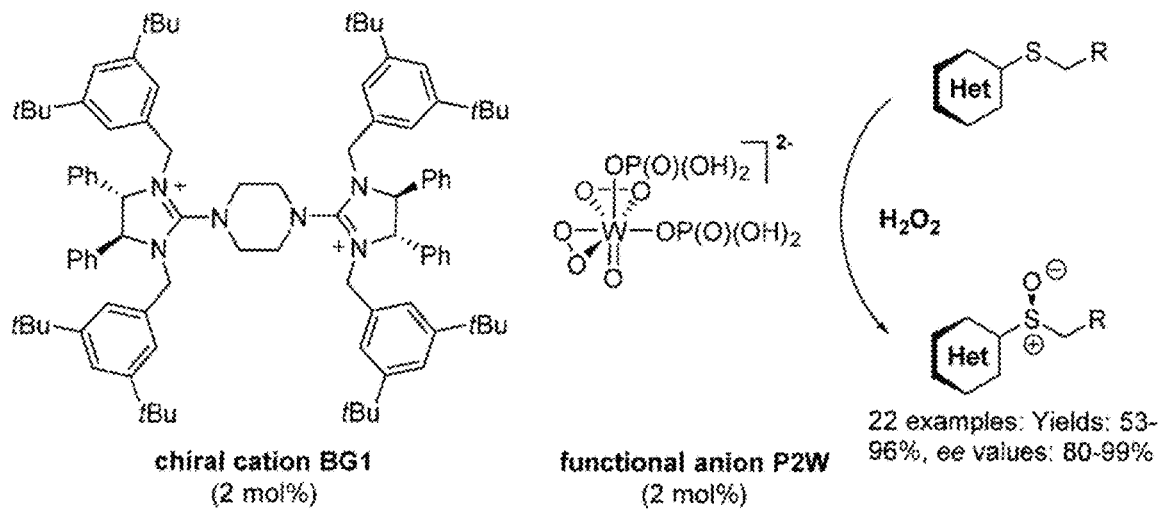
Figure 5:
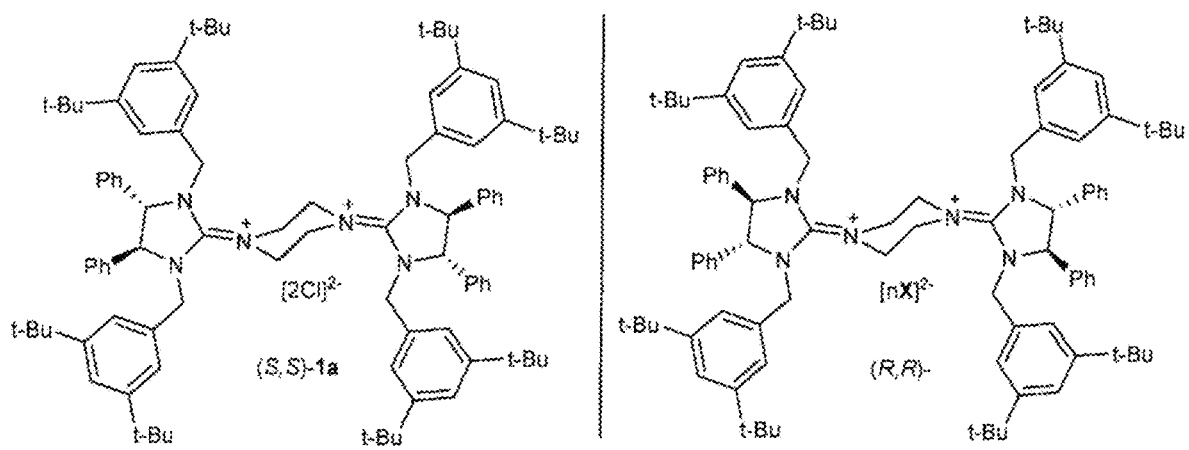
Figure 5:
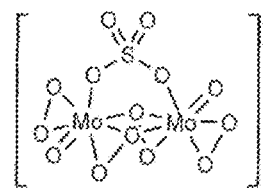
Figure 6:
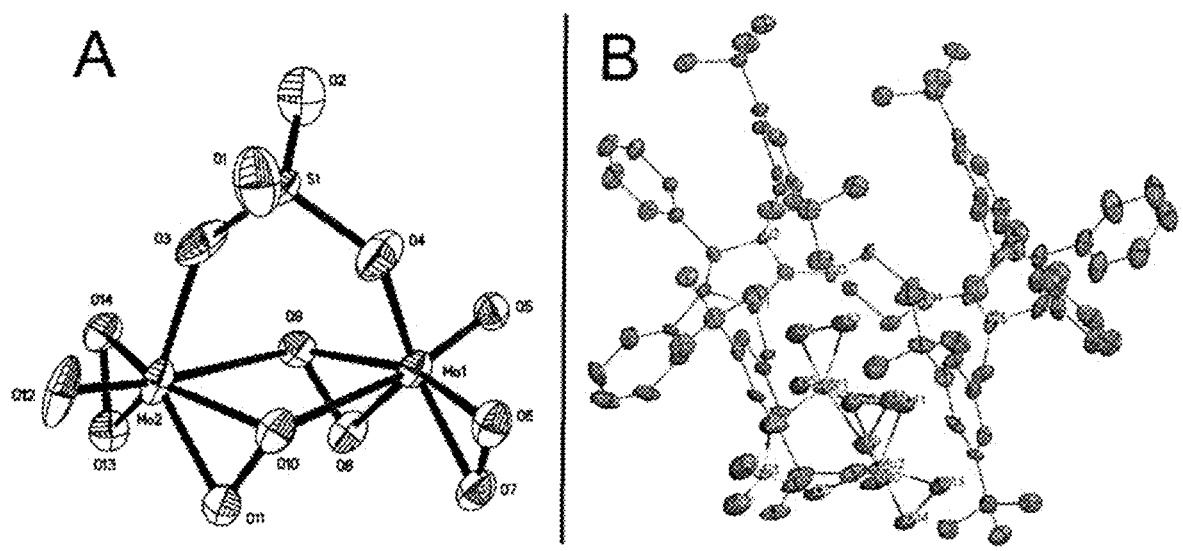
Figure 7:
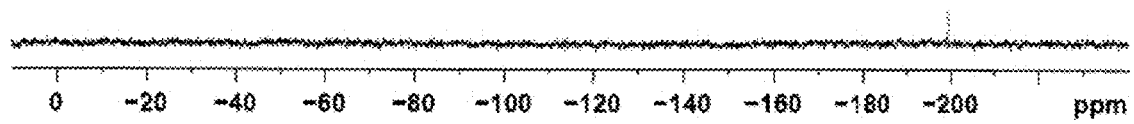
FIG. 7 depicts $^{95}Mo$ NMR spectra of A) a tetrabutylammonium analogue $[Bu_4N]_2[(\mu_2-SO_4)\{Mo_2O_2(\mu_2-O_2)_2(O_2)_2\}]$ and B) complex (R,R)-1c [Bisguanidinium][$(\mu_2-SO_4)\{Mo_2O_2(\mu_2-O_2)_2(O_2)_2\}$]

Preliminary computational studies of the complete ion-pair BG1-P2W structure using ONIOM method revealed a stable ion-pair interaction, where P2W is buried in the chiral cavity of BG1 (FIG. 2). This configuration results in only one of the peroxo-oxygen (marked as Oc in FIG. 2) being exposed, leaving it as the only possible reaction site. Without wishing to be bound by theory, it is hypothesized that this configuration will restrict the direction of approach of the sulfide, thereby providing fertile condition for an enantioselective reaction. A simple working model, which includes the initial formation of P2W in the aqueous phase through the interactions of silver tungstate, phosphate and hydrogen peroxide is thus proposed (FIG. 3). The formation of the ion-pair BG1-P2W in the organic phase is facilitated by BG1. After oxidation, P2W is regenerated in the aqueous phase by H$_2$O$_2$.

Example 9: Optimization of Reaction Conditions for Molybdate-Catalyzed Oxidation

TABLE 2

Asymmetric oxidation of methyl ester of methyl diphenyl methyl mercapto acetate (MDMMA) to methyl diphenyl methyl sulfinyl acetate (MDMSA) by using aqueous H$_2$O$_2$.

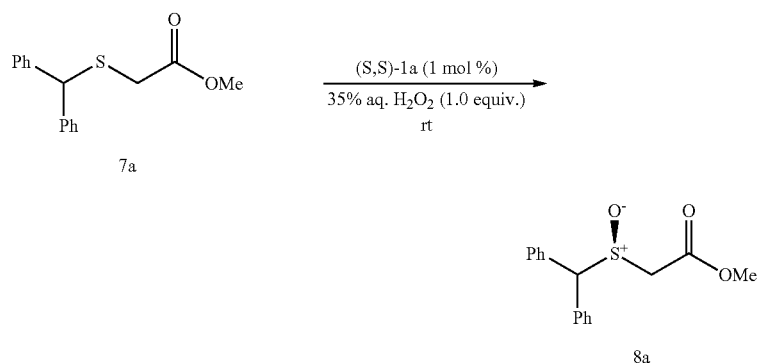

| Entry | [Mo] | Additive | Solvent | time | yield (%)[b] | ee (%)[c] |
|---|---|---|---|---|---|---|
| 1[d] | (NH$_4$)$_6$Mo$_7$O$_{24}$•4H$_2$O | — | Toluene | 24 | 0 | 0 |
| 2 | (NH$_4$)$_6$Mo$_7$O$_{24}$•4H$_2$O | — | Toluene | 24 | 15 | 0 |
| 3[d] | (NH$_4$)$_6$Mo$_7$O$_{24}$•4H$_2$O | CH$_3$CO$_2$H (1.0 equiv.) | Toluene | 24 | 0 | 0 |
| 4 | (NH$_4$)$_6$Mo$_7$O$_{24}$•4H$_2$O | CH$_3$CO$_2$H (1.0 equiv.) | Toluene | 24 | 14 | 20 |
| 5 | (NH$_4$)$_6$Mo$_7$O$_{24}$•4H$_2$O | CF$_3$CO$_2$H (1.0 equiv.) | Toluene | 8 | 80 | 4 |
| 6 | (NH$_4$)$_6$Mo$_7$O$_{24}$•4H$_2$O | NaHSO$_4$ (1.0 equiv.) | Toluene | 19 | 99 | 69 |
| 7 | (NH$_4$)$_6$Mo$_7$O$_{24}$•4H$_2$O | KHSO$_4$ (1.0 equiv.) | Toluene | 19 | 99 | 75 |
| 8 | (NH$_4$)$_6$Mo$_7$O$_{24}$•4H$_2$O | LiH$_2$PO$_4$ (1.0 equiv.) | Toluene | 19 | 50 | 40 |
| 9 | (NH$_4$)$_6$Mo$_7$O$_{24}$•4H$_2$O | Na$_2$HPO$_4$ (1.0 equiv.) | Toluene | 19 | 28 | 0 |
| 10 | Li$_2$MoO$_4$ | KHSO$_4$ (1.0 equiv.) | Toluene | 3 | 85 | 88 |
| 11 | Na$_2$MoO$_4$•2H$_2$O | KHSO$_4$ (1.0 equiv.) | Toluene | 2 | 99 | 88 |
| 12 | K$_2$MoO$_4$ | KHSO$_4$ (1.0 equiv.) | Toluene | 2 | 99 | 86 |
| 13 | Na$_2$MoO$_4$•2H$_2$O | KHSO$_4$ (0.5 equiv.) | Toluene | 2 | 99 | 89 |
| 14 | Na$_2$MoO$_4$•2H$_2$O | KHSO$_4$ (0.25 equiv.) | Toluene | 2 | 99 | 83 |
| 15 | Na$_2$MoO$_4$•2H$_2$O | KHSO$_4$ (0.5 equiv.) | Xylene | 2.5 | 99 | 92 |

TABLE 2-continued

| 16 | Na₂MoO₄•2H₂O | KHSO₄ (0.5 equiv.) | $^i$Pr₂O | 1 | 99 | 93 |
| 17$^e$ | Na₂MoO₄•2H₂O | KHSO₄ (0.5 equiv.) | $^i$Pr₂O | 1 | 99 | 94 |

Unless otherwise indicated, reaction was performed with 0.05 mmol of 7a in the presence of 1 mol % of chiral bisguanidinium (S,S)-1a and 5 mol % of molybdates salts [Mo] in 1.0 mL of solvent.
$^b$Yield of the isolated product.
$^c$Determined by HPLC analysis using Chiralcel AD-H column.
dWithout (S,S)-1a.
$^e$Reaction was conducted using 0.2 mmol of 7a at 0° C. with 2.5 mol % Na₂MoO₄•2H₂O.

As set out in Table 2, reaction conditions for molybdate-catalyzed sulfoxidation were optimized by varying, for example, the identity and amount of molybdate-containing salt, the sulfate-containing additive and the solvent. General Procedure 3 was applied as the synthetic protocol.

During our continuous efforts on the synthesis of enantioenriched sulfoxide compounds, it was observed that general electrophilic α-halogenated carboxylates are incompatible with the reaction conditions for the in situ generated sulfenate anion through retro-Michael process, even though benzyl bromide and alkyl iodide derivatives are suitable (see FIG. 15). Meanwhile, considering the high oxidative efficiency of the anionic peroxomolybdate species, a direct oxidation of 2-thio acetate to afford 2-sulfinyl acetate was conducted by utilizing molybdate salts in catalytic amount and stoichiometric aqueous H₂O₂ co-oxidant.

Methyl ester of methyl diphenyl methyl mercapto acetate (MDMMA) 7a was chosen as the model substrate (Table 2) for investigation since the oxidative product methyl diphenyl methyl sulfinyl acetate (MDMSA) 8a can be easily transformed to modafinil [James Ternois, et al., *Tetrahedron: Asymmetry* 18, 2959-2964 (2008); Ganapati D. Yadav, et al., *Org. Process Res. Dev.* 14, 537-543 (2010); Zheng-Zheng Li, et al., *Eur. J. Inorg. Chem.* 2015, 4335-4342 (2015)], which cannot be achieved by using the retro-Michael sulfenate anion strategy (see FIG. 15).

The reaction was initially performed in the absence of bisguanidinium phase transfer catalyst (Table 2, entry 1) by using 5 mol % of (NH₄)₆Mo₇O₂₄.4H₂O with 35% aqueous H₂O₂ as the terminal co-oxidant in toluene at room temperature. As expected, no oxidative product was obtained after 24 h and the starting material 7a was fully recovered. However, the addition of 1 mol % of bisguanidinium (S,S)-1a can slightly promote the proceedings of the oxidation, despite the low yield (15%, Table 2, entry 2) and no enantioselectivity. Acetic acid is frequently used as an additive in oxidation reactions for tuning the reactivity and selectivity (Liang Hong, et al., *Chem. Rev.* (2016)). Nevertheless, the outcome was still disappointing in low reactivity (Table 2, entries 3 and 4), even though a slightly higher enantioselectivity of 20% can be obtained. The addition of trifluoroacetic acid provided a dramatic enhancement of reactivity was achieved but with a negligible enantioselectivity (Table 2, entry 5). The addition of one equivalent of hydrogen sulfate (H. Firouzabadi, et al., *Adv. Synth. Catal.* 348, 434-438 (2006)) salts surprisingly resulted in a significant improvement of yield as well as enantioselectivity (Table 2, entries 6 and 7). Switching to other additives such as dihydrogen phosphate or hydrogen phosphate led to poor results (Table 2, entries 8 and 9). Upon further optimizations (Table 2, entries 9-16), it was found that the use of 5 mol % of Na₂MoO₄.2H₂O with 0.5 equivalent of KHSO₄ and 1 mol % of (S,S)-1a resulted in a superior system for the oxidation of MDMMA 7a in $^i$Pr₂O with aqueous H₂O₂ as co-oxidant (Table 2, entry 16). Finally, the optimal conditions were further established by lowering the temperature to 0° C. to afford the desired product 8a in 99% yield with 94% ee. The absolute configuration of 8a was confirmed to be S by comparison with the data in reported literatures (Thomas Prisinzano, et. al., *Tetrahedron: Asymmetry* 15, 1053-1058 (2004)).

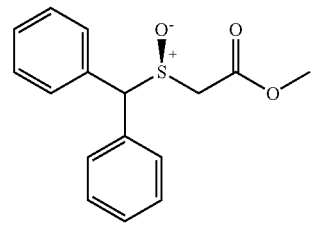

(S)-methyl 2-(benzhydrylsulfinyl)acetate (8a) was made from 7a, via General Procedure 3

White solid; 99% yield; mp: 103.8-105.5° C.; ¹H NMR (400 MHz, CDCl₃) δ 7.50 (dd, J=11.6, 7.9 Hz, 4H), 7.44-7.28 (m, 6H), 5.21 (s, 1H), 3.74 (s, 3H), 3.48 (dd, J=45.5, 14.0 Hz, 2H); ¹³C NMR (100 MHz, CDCl₃) δ 165.78, 135.21, 133.77, 129.55, 129.27, 128.78, 128.75, 128.56, 128.51, 71.55, 54.02, 52.74; IR: 1732.08, 1492.90, 1361.74, 1234.44, 1176.58, 1045.42, 975.98, 702.09 cm⁻¹; HRMS (ESI) calcd for C₁₆H₁₆O₃S m/z [M+H]⁺: 289.0898; found: 289.0892; HPLC analysis: Chiralcel AD-H (Hex/IPA=50/50, 1.0 mL/min, 230 nm, 22° C.), 7.0 (major), 12.6 min, 94% ee; [α]$_D^{22}$=+19.24 (c 5.51, MeOH).

Example 10: Asymmetric Sulfoxidation of Aliphatic 2-Thio Acetate by Chiral Bisguanidinium (S,S)-1a

TABLE 3

Asymmetric Sulfoxidation of Aliphatic 2-thio Acetate
By Chiral Bisguanidinium (S,S)-1a.

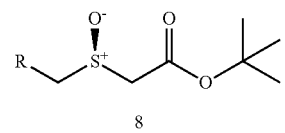

TABLE 3-continued

8f

| entry | R | 3 | time (h) | yield (%)[b] | ee (%)[c] |
|---|---|---|---|---|---|
| 1 | Ph | 8b | 0.8 | 99 | 90 |
| 2 | 4-MeC$_6$H$_4$ | 8c | 1 | 92 | 92 |
| 3[d] | 4-MeOC$_6$H$_4$ | 8d | 1 | 96 | 83 |
| 4 | 4-FC$_6$H$_4$ | 8e | 1 | 94 | 96 |
| 5 | 4ClC$_6$H$_4$ | 8f | 1 | 92 | 91 |
| 6 | 2-MeC$_6$H$_4$ | 8g | 1 | 98 | 92 |
| 7 | 2-ClC$_6$H$_4$ | 8h | 1 | 98 | 93 |
| 8 | 2-BrC$_6$H$_4$ | 8i | 1 | 99 | 93 |
| 9[d] | 2-thienyl | 8j | 1 | 94 | 89 |
| 10[d] | *t*-Bu | 8k | 1 | 83 | 37 |

Unless otherwise stated, reaction was performed with 0.2 mmol of 7 in the presence of 1 mol % of chiral bisguanidinium (S,S)-1a and 2.5 mol % of Na$_2$MoO$_4$·2H$_2$O in 1.0 mL of $^i$Pr$_2$O at 0° C.
[b]Yield of the isolated product.
[c]Determined by HPLC analysis.
[d]1.0 mL of $^n$Bu$_2$O was used as solvent.

The optimized reaction conditions as provided by the previous example (see entry 17, Table 2) was applied to general aliphatic 2-thio acetate substrates. $^n$Bu$_2$O solvent was used in certain cases to improve the enantioselectivities. It was found that the oxidation of substrates 7 proceeded rapidly to furnish sulfoxide products 8b-8k within 1 h. Generally, simple benzyl 2-thio acetates with different substitution patterns on the aromatic ring were well tolerated (Table 3, entries 1-8). Both electron-rich and electron-deficient substituents present in para- or ortho-position of the phenyl moiety resulted in excellent outcome. In most cases, high enantioselectivities (>90% ee) were observed, though a slight decrease in enantioselectivity was achieved for 4-methoxy substituted substrate (Table 2, entry 3, 83% ee). Substrate with heterocyclic moiety such as oxidant-sensitive 2-thienyl group was also investigated, providing the desired sulfoxide 8j in excellent yield with good enantioselectivity (Table 3, entry 9). However, tert-butyl substituted 2-thio acetate was a less favourable substrate, leading to low enantioselectivity (Table 3, entry 10). The absolute configuration of product 8f was confirmed to be R using single-crystal X-ray diffraction; thus, the absolute configuration of sulfoxides 8 was assigned by analogy to 8f.

The following sulfoxide products are made from their reduced forms (7b-7k) via General Procedure 3, unless otherwise stated.

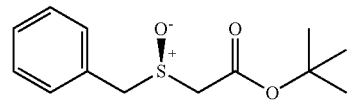

(R)-tert-butyl 2-(benzylsulfinyl)acetate (8b), from 7b

White solid; 90% yield; mp: 83.8-85.1° C.; $^1$H NMR (400 MHz, CDCl$_3$) δ 7.38 (t, J=6.7 Hz, 3H), 7.35-7.29 (m, 2H), 4.16 (dd, J=62.7, 13.0 Hz, 2H), 3.46 (q, J=14.0 Hz, 2H), 1.50 (s, 9H); $^{13}$C NMR (100 MHz, CDCl$_3$) δ 164.33, 130.37, 129.12, 128.98, 128.59, 83.50, 57.69, 54.68, 28.03; IR: 1735.93, 1454.33, 1396.46, 1276.88, 1257.59, 1161.15, 1029.99, 952.84, 767.67, 702.09, 416.62 cm$^{-1}$; HRMS (ESI) calcd for C$_{13}$H$_{18}$O$_3$S m/z [M+H]$^+$: 255.1055; found: 255.1054; HPLC analysis: Chiralcel AD-H (Hex/IPA=90/10, 1.0 mL/min, 230 nm, 22° C.), 9.8 (major), 16.4 min, 90% ee; [α]$_D^{22}$=+18.77 (c 5.03, MeOH).

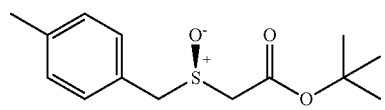

(R)-tert-butyl 2-((4-methylbenzyl)sulfinyl)acetate (8c), from 7c

White solid; 92% yield; mp: 99.8-102.0° C.; $^1$H NMR (400 MHz, CDCl$_3$) δ 7.23-7.16 (m, 4H), 4.11 (dd, J=59.9, 13.0 Hz, 2H), 3.44 (q, J=14.0 Hz, 2H), 2.35 (s, 3H), 1.49 (s, 9H); $^{13}$C NMR (100 MHz, CDCl$_3$) δ 164.37, 138.47, 130.22, 129.66, 125.91, 83.38, 57.40, 54.61, 28.00, 21.15; IR: 1728.22, 1516.05, 1300.02, 1149.57, 1118.71, 1022.27, 956.69, 821.68, 736.81, 466.77 cm$^{-1}$; HRMS (ESI) calcd for C$_{14}$H$_{20}$O$_3$S m/z [M+H]$^+$: 269.1211; found: 269.1211; HPLC analysis: Chiralcel AD-H (Hex/IPA=90/10, 1.0 mL/min, 230 nm, 22° C.), 9.8 (major), 15.1 min, 92% ee; [α]$_D^{22}$=+14.83 (c 4.86, MeOH).

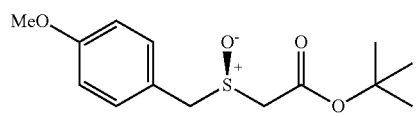

(R)-tert-butyl 2-((4-methoxybenzyl)sulfinyl)acetate (8d) from 7d

White solid; 96% yield; mp: 92.1-93.3° C.; $^1$H NMR (400 MHz, CDCl$_3$) δ 7.27 (d, J=8.4 Hz, 2H), 6.91 (t, J=10.6 Hz, 2H), 4.12 (dd, J=64.6, 13.2 Hz, 2H), 3.82 (s, 3H), 3.45 (q, J=14.0 Hz, 2H), 1.51 (s, 9H); $^{13}$C NMR (100 MHz, CDCl$_3$) δ 164.38, 159.87, 131.56, 120.84, 114.40, 83.39, 56.91, 55.27, 54.44, 28.01; IR: 1728.22, 1612.49, 1516.05, 1465.90, 1392.61, 1369.46, 1303.88, 1253.73, 1176.58, 1149.57, 1118.71, 1033.85, 837.11, 732.95 cm$^{-1}$; HRMS (ESI) calcd for C$_{14}$H$_{20}$O$_4$S m/z [M+H]$^+$: 285.1261; found: 285.1262; HPLC analysis: Chiralcel AD-H (Hex/IPA=90/10, 1.0 mL/min, 230 nm, 22° C.), 13.9 (major), 21.3 min, 83% ee; [α]$_D^{22}$=+16.13 (c 5.43, MeOH).

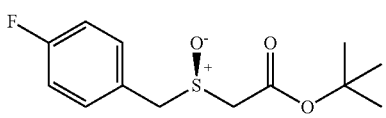

(R)-tert-butyl 2-((4-fluorobenzyl)sulfinyl)acetate (8e) from 7e

White solid; 94% yield; mp: 95.5-96.2° C.; $^1$H NMR (400 MHz, CDCl$_3$) δ 7.35-7.27 (m, 2H), 7.07 (t, J=8.6 Hz, 2H), 4.11 (dd, J=76.1, 13.2 Hz, 2H), 3.53-3.35 (m, 2H), 1.49 (s, 9H); $^{13}$C NMR (100 MHz, CDCl$_3$) 164.21, 162.92 (d, J=248.0 Hz), 132.11 (d, J=8.3 Hz), 124.92 (d, J=3.0 Hz), 115.94 (d, J=21.7 Hz), 83.56, 56.54, 54.60, 27.99; $^{19}$F NMR (376 MHz, CDCl$_3$) δ −112.91; IR: 1716.65. 1508.33, 1369.46, 1300.02, 1226.73, 1145.72, 1114.86, 1029.99, 840.96, 740.67, 528.50 cm$^{-1}$; HRMS (ESI) calcd for C$_{13}$H$_{17}$FO$_3$S m/z [M+H]$^+$: 273.0961; found: 273.0952; HPLC analysis: Chiralcel AD-H (Hex/IPA=90/10, 1.0 mL/min, 230 nm, 22° C.), 11.2 (major), 17.5 min, 96% ee; [α]$_D^{22}$=+29.96 (c 4.91, MeOH).

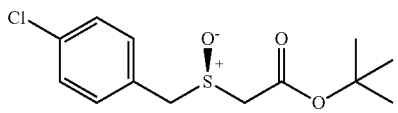

(R)-tert-butyl 2-((4-chlorobenzyl)sulfinyl)acetate (8f) from 7f

White solid; 92% yield; mp: 84.1-85.3° C.; $^1$H NMR (400 MHz, CDCl$_3$) δ 7.36 (d, J=8.4 Hz, 2H), 7.26 (d, J=8.4 Hz, 2H), 4.10 (dd, J=76.9, 13.2 Hz, 2H), 3.50-3.36 (m, 1H), 1.49 (s, 9H); $^{13}$C NMR (100 MHz, CDCl$_3$) δ 164.16, 134.74, 131.68, 129.11, 127.59, 83.60, 56.63, 54.65, 27.98; IR: 1724.36, 1712.79, 1597.06, 1492.90, 1454.33, 1369.46, 1303.88, 1261.45, 1145.72, 1095.57, 1018.41, 956.69, 914.26, 840.96, 740.67, 702.09, 671.23 cm$^{-1}$; HRMS (ESI) calcd for C$_{13}$H$_{17}$ClO$_3$S m/z [M+H]$^+$: 289.0665; found: 289.0668; HPLC analysis: Chiralcel AD-H (Hex/IPA=90/10, 1.0 mL/min, 230 nm, 22° C.), 11.9 (major), 18.5 min, 91% ee; [α]$_D^{22}$=+43.89 (c 5.21, MeOH).

A single crystal structure of (R)-8f is provided in FIG. 10A. Crystal data for (R)-8f: [C$_{13}$H$_{17}$ClO$_3$S], M=288.77, orthorhombic, P 21 21 21, a=5.2790(5), b=11.5315(8), c=23.4325(19) Å, α=90, β=90°, γ=90°, V=1426.4(2) Å$^3$, Z=4, ρ$_{calcd}$=1.345 g/cm$^3$, μ(CuKα)=0.412 mm$^{-1}$, T=103(2) K, Wavelength=0.71073 Å, colorless block. Bruker X8 CCD X-ray diffractometer; 3281 independent measured reflections, F$^2$ refinement, R$_1$(obs)=0.0377, wR$_2$(all)=0.0808, 3001 independent observed absorption-corrected reflections, 242 parameters. Crystallographic data for this paper have been deposited at the Cambridge Crystallographic Data Centre under deposition number CCDC 1456988.

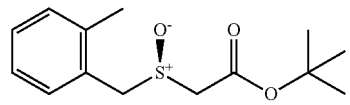 [SMILES: Cc1ccccc1C[S@@+]([O-])CC(=O)OC(C)(C)C]

(R)-tert-butyl 2-((2-methylbenzyl)sulfinyl)acetate (8g) from 7g

Colourless oil; 98% yield; $^1$H NMR (400 MHz, CDCl$_3$) δ 7.34-7.09 (m, 4H), 4.20 (dd, J=65.0, 12.9 Hz, 2H), 3.55 (dd, J=31.3, 13.9 Hz, 2H), 2.39 (s, 3H), 1.47 (s, 9H); $^{13}$C NMR (100 MHz, CDCl$_3$) δ 164.37, 137.70, 131.29, 130.86, 128.77, 128.31, 126.54, 83.48, 56.89, 55.84, 28.01, 19.82; IR: 1732.08, 1712.79, 1492.90, 1454.33, 1392.61, 1369.46, 1288.45, 1261.45, 1161.15, 1041.56, 952.84, 910.40, 837.11, 767.67, 482.20 cm$^{-1}$; HRMS (ESI) calcd for C$_{14}$H$_{20}$O$_3$S m/z [M+H]$^+$: 269.1211; found: 269.1210; HPLC analysis: Chiralcel AD-H (Hex/IPA=90/10, 1.0 mL/min, 230 nm, 22° C.), 8.2 (major), 15.6 min, 92% ee; [α]$_D^{22}$=+55.71 (c 5.15, MeOH).

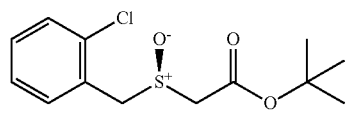 [SMILES: CC(C)(C)OC(=O)C[S@+]([O-])Cc1ccccc1Cl]

(R)-tert-butyl 2-((2-chlorobenzyl)sulfinyl)acetate (8h) from 7h

Colourless oil; 98% yield; $^1$H NMR (400 MHz, CDCl$_3$) δ 7.47-7.40 (m, 2H), 7.35-7.27 (m, 2H), 4.32 (dd, J=96.1, 12.9 Hz, 2H), 3.58 (dd, J=43.2, 13.9 Hz, 2H), 1.50 (s, 9H); $^{13}$C NMR (100 MHz, CDCl$_3$) δ 164.19, 134.66, 132.77, 130.04, 129.90, 127.99, 127.32, 83.57, 56.18, 55.96, 28.00; IR: 1728.22, 1712.79, 1473.62, 1446.61, 1392.61, 1369.46, 1296.16, 1261.45, 1157.29, 1053.13, 952.84, 910.40, 840.96, 763.81, 682.80, 578.64 cm$^{-1}$; HRMS (ESI) calcd for C$_{13}$H$_{17}$ClO$_3$S m/z [M+H]$^+$: 289.0665; found: 289.0665; HPLC analysis: Chiralcel AD-H (Hex/IPA=90/10, 1.0 mL/min, 230 nm, 22° C.), 10.4 (major), 32.7 min, 93% ee; [α]$_D^{22}$=+47.96 (c 5.55, MeOH).

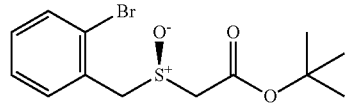

(R)-tert-butyl 2-((2-bromobenzyl)sulfinyl)acetate (8i) from 7i

Pale yellow oil; 99% yield; $^1$H NMR (400 MHz, CDCl$_3$) δ 7.61 (dd, J=8.0, 1.1 Hz, 1H), 7.43 (dd, J=7.6, 1.7 Hz, 1H), 7.32 (td, J=7.5, 1.2 Hz, 1H), 7.21 (td, J=7.7, 1.7 Hz, 1H), 4.33 (dd, J=99.7, 12.9 Hz, 2H), 3.59 (dd, J=46.8, 13.8 Hz, 2H), 1.50 (s, 9H); $^{13}$C NMR (100 MHz, CDCl$_3$) δ 164.15, 133.22, 132.78, 130.21, 129.83, 127.93, 125.10, 83.56, 58.53, 56.20, 28.00; IR: 1728.22, 1712.79, 1566.20, 1469.76, 1392.61, 1369.46, 1296.16, 1261.45, 1157.29, 1045.42, 1029.99, 952.84, 910.40, 837.11, 763.81, 659.66 cm$^{-1}$; HRMS (ESI) calcd for C$_{13}$H$_{17}$BrO$_3$S m/z [M+H]$^+$: 333.0160; found: 333.0170; HPLC analysis: Chiralcel AD-H (Hex/IPA=90/10, 1.0 mL/min, 230 nm, 22° C.), 10.7 (major), 40.1 min, 93% ee; [α]$_D^{22}$=+45.04 (c 6.6, MeOH).

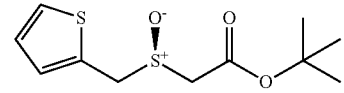 [SMILES: CC(C)(C)OC(=O)C[S@+]([O-])Cc1cccs1]

(S)-tert-butyl 2-((thiophen-2-ylmethyl)sulfinyl)acetate (8j) from 7j

White solid; 94% yield; mp: 67.7-68.4° C.; $^1$H NMR (400 MHz, CDCl$_3$) δ 7.33 (dd, J=5.1, 1.2 Hz, 1H), 7.09 (d, J=2.8 Hz, 1H), 7.06 (dd, J=5.0, 3.5 Hz, 1H), 4.37 (dd, J=62.5, 14.1 Hz, 2H), 3.47 (q, J=14.2 Hz, 2H), 1.50 (s, 9H); $^{13}$C NMR (100 MHz, CDCl$_3$) δ 164.19, 129.36, 129.28, 127.59, 127.10, 83.59, 54.30, 51.72, 28.03; IR: 1728.22, 1712.79, 1454.33, 1392.61, 1369.46, 1288.45, 1257.59, 1161.15, 1041.56, 952.84, 906.54, 840.96, 582.50, 474.49 cm$^{-1}$; HRMS (ESI) calcd for C$_{11}$H$_{16}$O$_3$S$_2$ m/z [M+H]$^+$: 261.0619; found: 261.0611; HPLC analysis: Chiralcel AD-H (Hex/IPA=90/10, 1.0 mL/min, 230 nm, 22° C.), 10.4 (major), 17.3 min, 89% ee; [α]$_D^{22}$=+18.2 (c 4.80, MeOH).

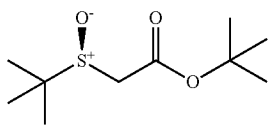

(S)-tert-butyl 2-(tert-butylsulfinyl)acetate (8k) from 7k

White solid; 83% yield; mp: 95.7-96.8° C.; $^1$H NMR (400 MHz, CDCl$_3$) δ 3.37 (dd, J=60.6, 13.6 Hz, 2H), 1.49 (s, 9H), 1.27 (s, 9H); $^{13}$C NMR (100 MHz, CDCl$_3$) δ 165.35, 83.20, 54.08, 52.83, 27.96, 22.71; IR: 1728.22, 1716.65, 1462.04, 1392.61, 1365.60, 1288.45, 1261.45, 1165.00, 1141.86, 1041.56, 956.69, 894.97, 840.96, 736.81 cm$^{-1}$; HRMS (ESI) calcd for C$_{10}$H$_{20}$O$_3$S m/z [M+H]$^+$: 221.1211; found: 221.1209; HPLC analysis: Chiralcel OD-H (Hex/IPA=95/5, 1.0 mL/min, 230 nm, 22° C.), 10.0 (major), 11.5 min, 37% ee; [α]$_D^{22}$=−33.03 (c 3.6, MeOH).

Example 11: Asymmetric Sulfoxidation of Aromatic 2-Thio Acetate

TABLE 4

Asymmetric Sulfoxidation of Aromatic 2-thio acetate by Chiral bisguanidinium (S,S)-1a.

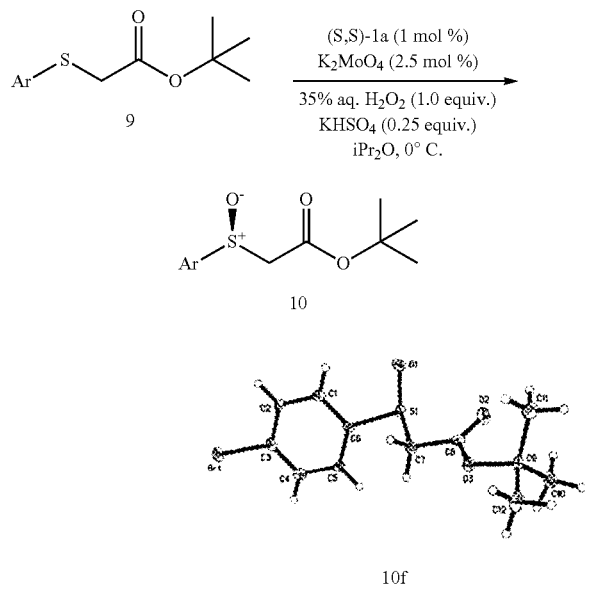

10f

TABLE 4-continued

| Entry | Ar | 10 | time (h) | yield (%)$^b$ | ee (%)$^c$ |
|---|---|---|---|---|---|
| 1 | Ph | 10a | 1 | 91 | 86 |
| 2 | 4-MeC$_6$H$_4$ | 10b | 1 | 93 | 83 |
| 3 | 4-MeOC$_6$H$_4$ | 10c | 1 | 94 | 79 |
| 4$^d$ | 4-FC$_6$H$_4$ | 10d | 1 | 93 | 89 |
| 5 | 4-ClC$_6$H$_4$ | 10e | 1 | 93 | 90 |
| 6 | 4-BrC$_6$H$_4$ | 10f | 1 | 95 | 91 |
| 7 | 2-MeC$_6$H$_4$ | 10g | 1 | 99 | 82 |
| 8$^d$ | 2-MeOC$_6$H$_4$ | 10h | 1 | 99 | 89 |
| 9 | 2-ClC$_6$H$_4$ | 10i | 4 | 99 | 81 |
| 10 | 1-naphthalenyl | 10j | 1 | 97 | 83 |
| 11$^e$ | 2-pyridyl | 10k | 4 | 99 | 52 |
| 12$^f$ | 2-benzothiazolyl | 10l | 24 | 79 | 74 |

Unless otherwise stated, reaction was performed with 0.2 mmol of 9 in the presence of 1 mol % of chiral bisguanidinium (S,S)-1a and 2.5 mol % of K$_2$MoO$_4$ in 1.0 mL of $^i$Pr$_2$O at 0° C.
$^b$Yield of the isolated product.
$^c$Determined by HPLC analysis.
$^d$1.0 mL of $^n$Bu$_2$O was used as solvent.
$^e$At room temperature.
$^f$The reaction was conducted at room temperature using 1.5 equiv. of 35% aqueous H$_2$O$_2$.

Aromatic 2-thio acetate substrates 9a-9l were prepared and examined in accordance with the procedure set out under Synthesis of Aromatic 2-thio acetate. Based on General Procedure 3 and some modifications, efficient oxidation of 9a-9l with a variety of substitution patterns was achieved by using 0.25 equivalent of KHSO$_4$ in the presence of 2.5 mol % of K$_2$MoO$_4$ (Table 4). Good to excellent yields and enantioselectivities were achieved in most cases. Generally, the reaction can be completed in less than one hour. However, for specific substrates with steric hindrance (Table 4, entry 10) or 2-pyridyl, 2-benzothiazolyl moieties (Table 4, entries 11 and 12), longer reaction time was required to achieve acceptable yield. Moreover, for less reactive substrates 9k and 9l, the reaction was conducted at elevated temperature (room temperature) with moderate enantioselectivities. Nevertheless, 2-benzothiazolyl substituted substrate 9l cannot be completely consumed within 24 h even with the addition 1.5 equivalent of aqueous hydrogen peroxide oxidant (Table 4, entry 12). The absolute configuration of product 10f was confirmed to be S using single-crystal X-ray diffraction; thus, the absolute configuration of sulfoxides 10 was assigned by analogy to 10f.

Characterization of Sulfoxide Products

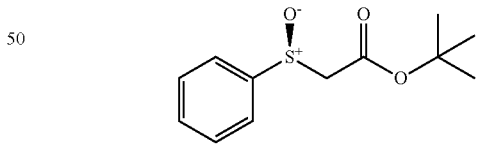

(S)-tert-butyl 2-(phenylsulfinyl)acetate (10a), from 9a

Yellow oil; 91% yield; $^1$H NMR (400 MHz, CDCl$_3$) δ 7.70 (dd, J=6.7, 3.0 Hz, 2H), 7.54 (dd, J=6.5, 2.7 Hz, 3H), 3.70 (dd, J=80.0, 13.7 Hz, 2H), 1.39 (s, 9H); $^{13}$C NMR (100 MHz, CDCl$_3$) δ 163.77, 143.29, 131.65, 129.30, 124.42, 83.25, 62.61, 27.88; IR: 1728.22, 1712.79, 1477.47, 1446.61, 1392.61, 1369.46, 1296.16, 1261.45, 1157.29, 1126.43, 1049.28, 952.84, 902.69, 840.96, 690.52, 667.37 cm$^{-1}$; HRMS (ESI) calcd for C$_{12}$H$_{16}$O$_3$S m/z [M+H]$^+$:

241.0898; found: 241.0900; HPLC analysis: Chiralcel OD-H (Hex/IPA=90/10, 1.0 mL/min, 254 nm, 22° C.), 8.9, 11.6 (major) min, 86% ee; $[\alpha]_D^{22}$=−122.64 (c 4.31, MeOH).

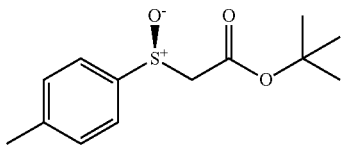 [SMILES: Cc1ccc([S@@+]([O-])CC(=O)OC(C)(C)C)cc1]

(S)-tert-butyl 2-(p-tolylsulfinyl)acetate (10b), from 9b

Pale yellow oil; 93% yield; $^1$H NMR (400 MHz, CDCl$_3$) δ 7.58 (d, J=8.1 Hz, 2H), 7.33 (d, J=7.9 Hz, 2H), 3.68 (dd, J=89.1, 13.6 Hz, 2H), 2.42 (s, 3H), 1.40 (s, 9H); $^{13}$C NMR (100 MHz, CDCl$_3$) δ 163.85, 142.26, 140.03, 129.97, 124.48, 83.16, 62.68, 27.88, 21.44; IR: 1724.36, 1492.90, 1454.33, 1392.61, 1369.46, 1292.31, 1261.45, 1161.15, 1126.43, 1083.99, 1049.28, 840.96, 813.96 cm$^{-1}$; HRMS (ESI) calcd for C$_{13}$H$_{18}$O$_3$S m/z [M+H]$^+$: 255.1055; found: 255.1056; HPLC analysis: Chiralcel OB-H (Hex/IPA=90/10, 1.0 mL/min, 230 nm, 22° C.), 7.3 (major), 8.8 min, 83% ee; $[\alpha]_D^{22}$=−114.17 (c 4.58, MeOH).

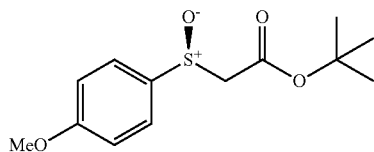 [SMILES: COc1ccc([S@@+]([O-])CC(=O)OC(C)(C)C)cc1]

(S)-tert-butyl 2-((4-methoxyphenyl)sulfinyl)acetate (10c), from 9c

Pale yellow oil; 94% yield; $^1$H NMR (400 MHz, CDCl$_3$) δ 7.64 (d, J=8.7 Hz, 2H), 7.03 (d, J=8.7 Hz, 2H), 3.86 (s, 3H), 3.70 (dd, J=108, 13.6 Hz, 2H), 1.39 (s, 9H); $^{13}$C NMR (100 MHz, CDCl$_3$) δ 163.84, 162.47, 134.10, 126.53, 114.78, 83.11, 62.68, 55.55, 27.89; IR: 1728.22, 1712.79, 1593.20, 1496.76, 1462.04, 1392.61, 1369.46, 1296.16, 1257.59, 1161.15, 1122.57, 1087.85, 1029.99, 952.84, 902.69, 833.25, 798.53, 756.10, 667.37 cm$^{-1}$; HRMS (ESI) calcd for C$_{13}$H$_{18}$O$_4$S m/z [M+H]$^+$: 271.1004; found: 271.1007; HPLC analysis: Chiralcel OB-H (Hex/IPA=90/10, 1.0 mL/min, 230 nm, 22° C.), 11.8 (major), 14.9 min, 79% ee; $[\alpha]_D^{22}$=−91.45 (c 4.97, MeOH).

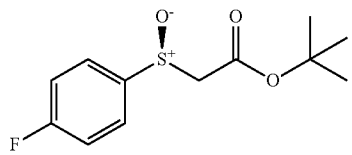 [SMILES: CC(C)(C)OC(=O)C[S@+]([O-])c1ccc(F)cc1]

(S)-tert-butyl 2-((4-fluorophenyl)sulfinyl)acetate (10d), from 9d

White solid; 93% yield; mp: 95.1-95.8° C.; $^1$H NMR (400 MHz, CDCl$_3$) δ 7.70 (ddd, J=8.4, 5.1, 1.3 Hz, 2H), 7.25-7.17 (m, 2H), 3.69 (ddd, J=87.8, 13.7, 1.0 Hz, 2H), 1.39 (s, 9H); $^{13}$C NMR (100 MHz, CDCl$_3$) δ 165.92, 163.50 (d, J=18.4 Hz), 138.73 (d, J=3.0 Hz), 126.86 (d, J=9.0 Hz), 116.63 (d, J=22.6 Hz), 83.38, 62.63, 27.86; $^{19}$F NMR (376 MHz, CDCl$_3$) δ −107.41; IR: 1724.36, 1585.49, 1492.90, 1469.76, 1369.46, 1296.16, 1257.59, 1215.15, 1157.29, 1080.14, 1037.70, 837.11 cm$^{-1}$; HRMS (ESI) calcd for C$_{12}$H$_{15}$FO$_3$S m/z [M+H]$^+$: 259.0804; found: 259.0804; HPLC analysis: Chiralcel OD-H (Hex/IPA=90/10, 1.0 mL/min, 230 nm, 22° C.), 8.7, 9.7 (major) min, 89% ee; $[\alpha]_D^{22}$=−115.46 (c 4.74, MeOH).

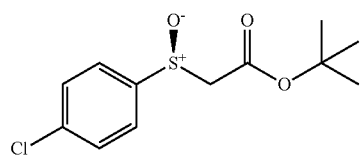

(S)-tert-butyl 2-((4-chlorophenyl)sulfinyl)acetate (10e), from 9e

Pale yellow solid; 93% yield; mp: 115.4-116.9° C.; $^1$H NMR (400 MHz, CDCl$_3$) δ 7.65 (d, J=8.5 Hz, 2H), 7.52 (d, J=8.5 Hz, 2H), 3.69 (dd, J=77.7, 13.8 Hz, 2H), 1.41 (s, 9H); $^{13}$C NMR (100 MHz, CDCl$_3$) δ 163.58, 141.86, 137.94, 129.61, 125.88, 83.54, 62.58, 27.92; IR: 1724.36, 1573.91, 1477.47, 1369.46, 1157.29, 1087.85, 1037.70, 1010.70, 825.53, 740.67 cm$^{-1}$; HRMS (ESI) calcd for C$_{12}$H$_{15}$ClO$_3$S m/z [M+H]$^+$: 275.0509; found: 275.0507; HPLC analysis: Chiralcel OB-H (Hex/IPA=90/10, 1.0 mL/min, 230 nm, 22° C.), 8.1 (major), 9.4 min, 90% ee; $[\alpha]_D^{22}$=−136.61 (c 4.96, MeOH).

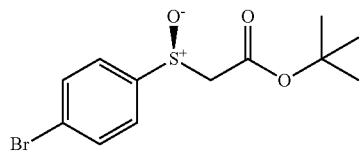 [SMILES: CC(C)(C)OC(=O)C[S@+]([O-])c1ccc(Cl)cc1]

(S)-tert-butyl 2-((4-bromophenyl)sulfinyl)acetate (10f), from 9f

Pale yellow solid; 95% yield; mp: 99.2-100.4° C.; $^1$H NMR (400 MHz, CDCl$_3$) δ 7.68 (d, J=8.6 Hz, 2H), 7.58 (d, J=8.6 Hz, 2H), 3.69 (dd, J=75.2, 13.8 Hz, 2H), 1.42 (s, 9H); $^{13}$C NMR (100 MHz, CDCl$_3$) δ 163.57, 142.47, 132.54, 126.19, 126.02, 83.56, 62.51, 27.92; IR: 1724.36, 1570.06, 1469.76, 1369.46, 1300.02, 1257.59, 1149.57, 1045.42, 1006.84, 821.68, 721.38 cm$^{-1}$; HRMS (ESI) calcd for C$_{12}$H$_{15}$BrO$_3$S m/z [M+H]$^+$: 319.0004; found: 319.0013; HPLC analysis: Chiralcel OB-H (Hex/IPA=90/10, 1.0 mL/min, 230 nm, 22° C.), 9.0 (major), 10.4 min, 91% ee; $[\alpha]_D^{22}$=−123.13 (c 4.95, MeOH).

A single-crystal structure of (S)-10f is provided in FIG. 10B. Crystal data for (S)-10f: [C$_{12}$H$_{15}$BrO$_3$S], M=319.21, monoclinic, P 1 21 1, a=26.8296(16), b=9.6925(5), c=10.5106(6) Å, α=90, β=101.2326(19)°, γ=90°, V=2680.9 (3) Å$^3$, Z=8, ρ$_{calcd}$=1.582 g/cm$^3$, μ(CuKα)=3.216 mm$^{-1}$, T=103(2) K, Wavelength=0.71073 Å, colorless plate. Bruker X8 CCD X-ray diffractometer; 22922 independent measured reflections, F$^2$ refinement, R$_1$(obs)=0.0620, wR$_2$ (all)=0.1213, 10957 independent observed absorption-corrected reflections, 626 parameters. Crystallographic data for this paper have been deposited at the Cambridge Crystallographic Data Centre under deposition number CCDC 1456989.

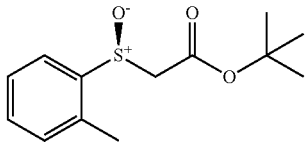 [SMILES: Cc1ccccc1[S@@+]([O-])CC(=O)OC(C)(C)C]

(S)-tert-butyl 2-(o-tolylsulfinyl)acetate (10g), from 9g

Pale yellow oil; 99% yield; $^1$H NMR (400 MHz, CDCl$_3$) δ 7.93 (dd, J=7.5, 1.7 Hz, 1H), 7.49-7.35 (m, 2H), 7.20 (d, J=6.8 Hz, 1H), 3.71-3.55 (m, 2H), 2.41 (s, 3H), 1.39 (s, 9H); $^{13}$C NMR (100 MHz, CDCl$_3$) δ 163.96, 141.42, 134.94, 131.27, 130.72, 127.30, 124.26, 83.12, 60.86, 27.82, 18.21; IR: 1728.22, 1458.18, 1388.75, 1369.46, 1296.16, 1161.15, 1118.71, 1068.56, 1037.70, 952.84, 837.11, 759.95 cm$^{-1}$; HRMS (ESI) calcd for C$_{13}$H$_{18}$O$_3$S m/z [M+H]$^+$: 255.1055; found: 255.1062; HPLC analysis: Chiralcel OD-H (Hex/IPA=90/10, 1.0 mL/min, 230 nm, 22° C.), 7.8, 9.4 (major) min, 82% ee; $[\alpha]_D^{22}$=−158.63 (c 5.05, MeOH).

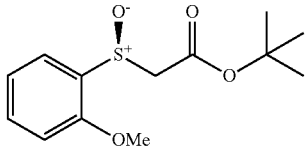 [SMILES: COc1ccccc1[S@@+]([O-])CC(=O)OC(C)(C)C]

(S)-tert-butyl 2-((2-methoxyphenyl)sulfinyl)acetate (10h), from 9h

Pale yellow oil; 99% yield; $^1$H NMR (400 MHz, CDCl$_3$) δ 7.81 (dd, J=7.7, 1.7 Hz, 1H), 7.50-7.42 (m, 1H), 7.19 (td, J=7.6, 0.8 Hz, 1H), 6.93 (d, J=8.2 Hz, 1H), 3.89 (s, 3H), 3.75 (dd, J=136.5, 13.7 Hz, 2H), 1.41 (s, 9H); $^{13}$C NMR (100 MHz, CDCl$_3$) δ 164.34, 155.00, 132.37, 130.29, 125.81, 121.64, 110.53, 82.80, 58.46, 55.75, 27.92; IR: 1728.22, 1712.79, 1585.49, 1477.47, 1392.61, 1276.88, 1161.15, 1122.57, 1072.42, 1041.56, 1018.41, 952.84, 902.69, 837.11, 759.95, 663.51 cm$^{-1}$; HRMS (ESI) calcd for C$_{13}$H$_{18}$O$_4$S m/z [M+H]$^+$: 271.1004; found: 271.1004; HPLC analysis: Chiralcel OD-H (Hex/IPA=90/10, 1.0 mL/min, 230 nm, 22° C.), 11.3, 12.7 (major) min, 89% ee; $[\alpha]_D^{22}$=−303.09 (c 5.28, MeOH).

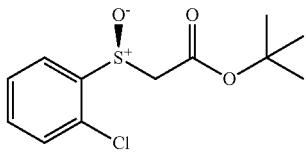 [SMILES: CC(C)(C)OC(=O)C[S@+]([O-])c1ccccc1Cl]

(S)-tert-butyl 2-((2-chlorophenyl)sulfinyl)acetate (10i), from 9i

Yellow oil; 99% yield; $^1$H NMR (400 MHz, CDCl$_3$) δ 7.94 (dd, J=7.8, 1.4 Hz, 1H), 7.53 (td, J=7.7, 1.2 Hz, 1H), 7.46 (td, J=7.6, 1.6 Hz, 1H), 7.40 (dd, J=7.8, 1.0 Hz, 1H), 3.76 (dd, J=140.3, 13.9 Hz, 2H), 1.43 (s, 9H); $^{13}$C NMR (100 MHz, CDCl$_3$) δ 163.74, 140.95, 132.32, 130.03, 129.73, 127.98, 126.47, 83.32, 59.22, 27.91; IR: 1728.22, 1712.79, 1573.91, 1454.33, 1392.61, 1369.46, 1288.45, 1161.15, 1126.43, 1068.56, 1029.99, 952.84, 898.83, 837.11, 759.95, 729.09, 663.51 cm$^{-1}$; HRMS (ESI) calcd for C$_{12}$H$_{15}$ClO$_3$S m/z [M+H]$^+$: 275.0509; found: 275.0507; HPLC analysis: Chiralcel OD-H (Hex/IPA=90/10, 1.0 mL/min, 230 nm, 22° C.), 7.6, 8.9 (major) min, 81% ee; $[\alpha]_D^{22}$=−238.00 (c 5.41, MeOH).

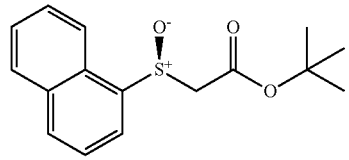 [SMILES: CC(C)(C)OC(=O)C[S@+]([O-])c1cccc2ccccc12]

(S)-tert-butyl 2-(naphthalen-1-ylsulfinyl)acetate (10j), from 9j

Pale yellow solid; 97% yield; mp: 95.6-96.3° C.; $^1$H NMR (400 MHz, CDCl$_3$) δ 8.18 (dd, J=7.3, 1.0 Hz, 1H), 8.01 (dd, J=12.1, 5.1 Hz, 2H), 7.94 (dd, J=6.9, 2.6 Hz, 1H), 7.72-7.63 (m, 1H), 7.63-7.53 (m, 2H), 3.78 (dd, J=58.6, 13.8 Hz, 2H), 1.37 (s, 9H); $^{13}$C NMR (100 MHz, CDCl$_3$) δ 164.11, 138.89, 133.41, 131.72, 129.05, 128.71, 127.50, 126.78, 125.59, 123.51, 121.49, 83.20, 61.69, 27.82; IR: 1728.22, 1504.48, 1454.33, 1369.46, 1296.16, 1161.15, 1114.86, 1053.13, 952.84, 898.83, 837.11, 802.39, 771.53, 736.81, 702.09 cm$^{-1}$; HRMS (ESI) calcd for C$_{16}$H$_{18}$O$_3$S m/z [M+H]$^+$: 291.1055; found: 291.1058; HPLC analysis: Chiralcel OD-H (Hex/IPA=90/10, 1.0 mL/min, 230 nm, 22° C.), 12.4 (major), 28.9 min, 83% ee; $[\alpha]_D^{22}$=−280.80 (c 5.60, MeOH).

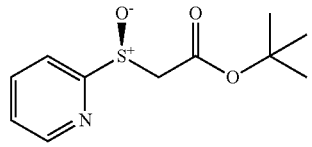 [SMILES: CC(C)(C)OC(=O)C[S@+]([O-])c1ccccn1]

(S)-tert-butyl 2-(pyridin-2-ylsulfinyl)acetate (10k), from 9k

Pale yellow oil; 99% yield; $^1$H NMR (400 MHz, CDCl$_3$) δ 8.61 (d, J=4.6 Hz, 1H), 7.98 (dt, J=26.9, 7.5 Hz, 2H), 7.40 (dd, J=6.6, 5.5 Hz, 1H), 3.88 (ddd, J=102.7, 14.0, 1.0 Hz, 2H), 1.41 (s, 9H); $^{13}$C NMR (100 MHz, CDCl$_3$) δ 163.82, 163.68, 149.29, 138.18, 124.85, 120.42, 83.13, 59.28, 27.89; IR: 1728.22, 1577.77, 1562.34, 1454.33, 1423.47, 1392.61, 1369.46, 1288.45, 1261.45, 1161.15, 1114.86, 1087.85, 1056.99, 1041.56, 991.41, 952.84, 902.69, 837.11, 771.53, 617.22 cm$^{-1}$; HRMS (ESI) calcd for C$_{11}$H$_{15}$NO$_3$S m/z [M+H]$^+$: 242.0851; found: 242.0851; HPLC analysis: Chiralcel OD-H (Hex/IPA=90/10, 1.0 mL/min, 254 nm, 22° C.), 10.6, 12.1 (major) min, 52% ee; $[\alpha]_D^{22}$=−85.44 (c 5.03, MeOH).

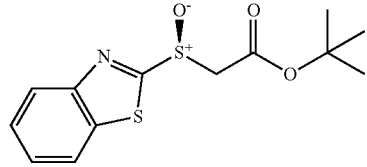 [SMILES: CC(C)(C)OC(=O)C[S@+]([O-])c1nc2ccccc2s1]

(S)-tert-butyl 2-(benzo[d]thiazol-2-ylsulfinyl)acetate (10l), from 91

Pale yellow solid; 79% yield; mp: 77.9-78.8° C.; $^1$H NMR (400 MHz, CDCl$_3$) δ 8.07 (d, J=8.2 Hz, 1H), 8.02 (d, J=7.9 Hz, 1H), 7.58 (t, J=7.6 Hz, 1H), 7.51 (t, J=7.6 Hz, 1H), 4.09 (dd, J=43.2, 14.3 Hz, 2H), 1.46 (s, 9H); $^{13}$C NMR (100 MHz, CDCl$_3$) δ 176.25, 162.99, 153.69, 136.20, 127.04, 126.38, 124.08, 122.31, 84.03, 61.60, 27.93; IR: 1728.22, 1458.18, 1392.61, 1369.46, 1288.45, 1261.45, 1157.29, 1068.56, 844.82, 759.95, 729.09 cm$^{-1}$; HRMS (ESI) calcd for C$_{13}$H$_{15}$NO$_3$S$_2$ m/z [M+H]$^+$: 298.0572; found: 298.0572; HPLC analysis: Chiralcel OB-H (Hex/IPA=90/10, 1.0 mL/min, 254 nm, 22° C.), 12.5 (major), 14.9 min, 74% ee; $[\alpha]_D^2$=−42.92 (c 4.72, MeOH).

Example 12: Sulfoxidation of Other Substrates Using Molybdate System

Scheme 5: Unless otherwise stated, reaction was performed with 0.2 mmol of 6 in the presence of 1 mol % of chiral bisguanidinium (S,S)-1a and 2.5 mmol % of molybdate salts in 1.0 mL of $^i$Pr$_2$O at 0° C. $^b$2.5 mol % of K$_2$MoO$_4$ and 0.5 equivalent of KHSO$_4$ were used. $^c$With 2.5 mol % of Na$_2$MoO$_4$·2H$_2$O and 0.5 equivalent of KHSO$_4$. $^d$With 2.5 mol % of K$_2$MoO$_4$ and 0.25 equivalent of KHSO$_4$.

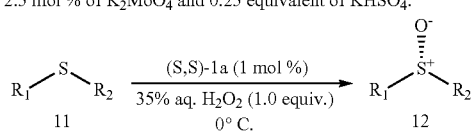

12a$^b$

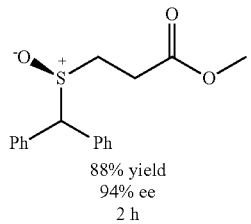

88% yield
94% ee
2 h

12b$^b$

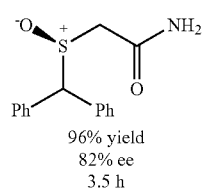

96% yield
82% ee
3.5 h

12c$^c$

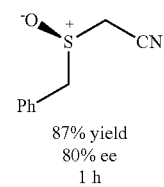

87% yield
80% ee
1 h

12d$^b$

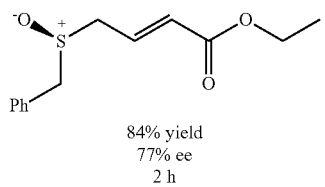

84% yield
77% ee
2 h

12e$^c$

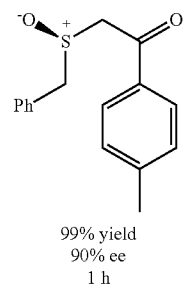

99% yield
90% ee
1 h

12f$^c$

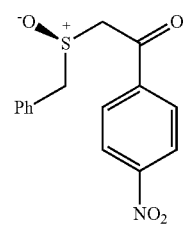

95% yield
85% ee
3 h

12g$^d$

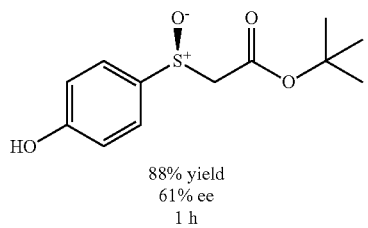

88% yield
61% ee
1 h

12h$^d$

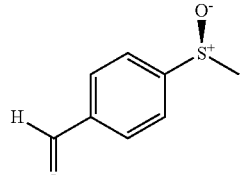

82% yield
65% ee
1 h

To further explore the generality of the current catalytic system, substrates containing various functionalities such as amide, nitrile, acrylate, ketone, nitro, phenol and aldehyde were examined (Scheme 5). 3-thio acetate substrate 11a can be efficiently oxidized to 3-sulfinyl acetate 12a in 88% yield with an excellent enantioselectivity of 94%, while only moderate enantioselectivity of 82% was achieved by direct oxidation of 2-sulfinyl amide 11b to modafinil 12b under present system. Interestingly, the substrate bearing electron-deficient alkenes was compatible with current conditions to afford the sulfide oxidation product 12d in good enantioselectivity without any epoxide formation. Moreover, it was noted that benzylic 2-thio ketone substrates were smoothly converted to their corresponding sulfoxides 12e and 12f in high yield with excellent enantioselectivity. Oxidant- or acid-sensitive functional groups in substrates 11g and 11h were typically not affected, providing the hydroxyl and formyl sulfoxides 12g and 12h, respectively, in fairly good yield with moderate enantioselectivity.

The following sulfoxide products are made from their reduced forms (11a-11h) via General Procedure 3, unless otherwise stated.

The absolute configuration of products 12 was assigned by analogy to either 8f or 10f (Scheme 5).

Characterization of Sulfoxide Products

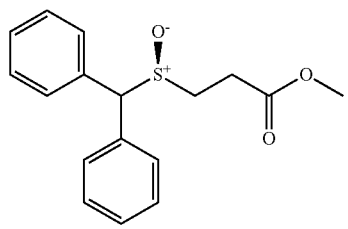 [SMILES: COC(=O)CC[S@+]([O-])C(c1ccccc1)c1ccccc1]

(S)-methyl 3-(benzhydrylsulfinyl)propanoate (12a), from 11a

White solid; 88% yield; mp: 98.7-99.6° C.; $^1$H NMR (400 MHz, CDCl$_3$) δ 7.52-7.46 (m, 2H), 7.46-7.28 (m, 8H), 4.88 (s, 1H), 3.67 (s, 3H), 2.94-2.61 (m, 4H); $^{13}$C NMR (100 MHz, CDCl$_3$) δ 171.68, 135.35, 134.74, 129.27, 129.20, 128.74, 128.52, 128.42, 128.32, 72.78, 52.03, 45.43, 26.89; IR: 1732.08, 1492.90, 1361.74, 1238.30, 1176.58, 1045.42, 736.81, 702.09 cm$^{-1}$; HRMS (ESI) calcd for C$_{17}$H$_{18}$O$_3$S m/z [M+H]$^+$: 303.1055; found: 303.1046; HPLC analysis: Chiralcel AD-H (Hex/IPA=80/20, 1.0 mL/min, 230 nm, 22° C.), 14.5 (major), 24.6 min, 94% ee; [α]$_D^{22}$=+11.16 (c 5.25, MeOH).

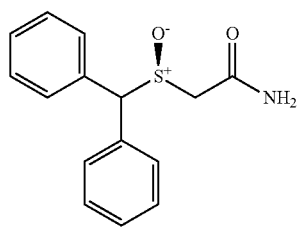 [SMILES: NC(=O)C[S@+]([O-])C(c1ccccc1)c1ccccc1]

(S)-2-(benzhydrylsulfinyl)acetamide (12b), from 11b

White solid; 96% yield; mp: 160.4-161.2° C.; $^1$H NMR (400 MHz, DMSO) δ 7.67 (s, 1H), 7.56-7.47 (m, 4H), 7.46-7.38 (m, 4H), 7.38-7.33 (m, 2H), 7.30 (s, 1H), 5.33 (s, 1H), 3.29 (dd, J=57.5, 13.6 Hz, 2H); $^{13}$C NMR (100 MHz, DMSO) δ 166.87, 137.68, 135.42, 130.21, 129.54, 128.99, 128.46, 128.44, 69.30, 56.64; IR: 3170.97, 1693.50, 1612.49, 1454.33, 1400.32, 1033.85, 740.67, 482.20. 455.20 cm$^{-1}$; HRMS (ESI) calcd for C$_{15}$H$_{15}$NO$_2$S m/z [M+H]$^+$: 274.0902; found: 274.0905; HPLC analysis: Chiralcel AS-H (Hex/IPA=50/50, 1.0 mL/min, 230 nm, 22° C.), 12.8 (major), 29.8 min, 82% ee; [α]$_D^{22}$=+14.44 (c 5.24, MeOH).

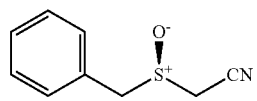 [SMILES: N#CC[S@+]([O-])Cc1ccccc1]

(R)-2-(benzylsulfinyl)acetonitrile (12c), from 11c

White solid; 87% yield; mp: 110.4-111.8° C.; $^1$H NMR (400 MHz, CDCl$_3$) δ 7.47-7.39 (m, 3H), 7.36 (dt, J=4.9, 4.0 Hz, 2H), 4.36-4.18 (m, 2H), 3.42 (dd, J=76.6, 16.1 Hz, 2H); $^{13}$C NMR (100 MHz, CDCl$_3$) δ 130.04, 129.42, 129.26, 127.53, 111.27, 57.86, 36.87; IR: 2306.86, 1419.61, 1076.28, 894.97, 740.67, 702.09 cm$^{-1}$; HRMS (ESI) calcd for C$_9$H$_9$NOS m/z [M+H$^-$]$^+$: 180.0483; found: 180.0484; HPLC analysis: Chiralcel OB-H (Hex/IPA=90/10, 1.0 mL/min, 230 nm, 22° C.), 14.0 (major), 18.2 min, 80% ee; [α]$_D^{22}$=+58.46 (c 3.05, MeOH).

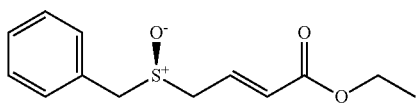 [SMILES: CCOC(=O)/C=C/C[S@+]([O-])Cc1ccccc1]

(S,E)-ethyl 4-(benzylsulfinyl)but-2-enoate (12d), from 11d

Pale yellow oil; 84% yield; $^1$H NMR (400 MHz, CDCl$_3$) δ 7.42-7.31 (m, 3H), 7.28 (dd, J=7.6, 1.7 Hz, 2H), 6.93 (dt, J=15.6, 7.8 Hz, 1H), 6.06 (dt, J=15.6, 1.1 Hz, 1H), 4.33-4.08 (m, 2H), 4.06-3.87 (m, 2H), 3.42 (dddd, J=60.4, 13.2, 7.8, 1.2 Hz, 2H), 1.28 (t, J=7.1 Hz, 3H); $^{13}$C NMR (100 MHz, CDCl$_3$) δ 164.98, 134.61, 129.93, 129.28, 129.05, 128.68, 128.55, 60.71, 57.35, 52.26, 14.10; IR: 3032.10, 1712.79, 1651.07, 1496.76, 1454.33, 1396.46, 1369.46, 1319.31, 1273.02, 1199.72, 1149.57, 1041.56, 979.84, 767.67, 702.09 cm$^{-1}$; HRMS (ESI) calcd for C$_{13}$H$_{16}$O$_3$S m/z [M+H]$^+$: 253.0898; found: 253.0896; HPLC analysis: Chiralcel OB-H (Hex/IPA=50/50, 1.0 mL/min, 230 nm, 22° C.), 8.5 (major), 18.9 min, 77% ee; [α]$_D^{22}$=−6.73 (c 4.19, MeOH).

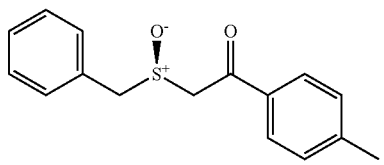 [SMILES: Cc1ccc(C(=O)C[S@+]([O-])Cc2ccccc2)cc1]

(R)-2-(benzylsulfinyl)-1-(p-tolyl)ethanone (12e), from 11e

Yellow solid; 99% yield; mp: 104.8-106.1° C.; $^1$H NMR (400 MHz, CDCl$_3$) δ 7.80 (d, J=8.3 Hz, 2H), 7.42-7.30 (m, 5H), 7.30-7.22 (m, 2H), 4.17 (ddd, J=19.0, 16.5, 8.3 Hz, 4H), 2.42 (s, 3H); $^{13}$C NMR (100 MHz, CDCl$_3$) δ 192.05, 145.48, 133.56, 130.45, 129.57, 129.20, 128.86, 128.78, 128.51, 57.71, 57.61, 21.72; IR: 1670.35, 1604.77, 1492.90, 1454.33, 1411.89, 1315.45, 1280.73, 1184.29, 1072.42, 1029.99, 975.98, 840.96, 763.81, 702.09 cm$^{-1}$; HRMS (ESI) calcd for C$_{16}$H$_{16}$O$_2$S m/z [M+H]$^+$: 272.0949; found: 272.0944; HPLC analysis: Chiralcel AD-H (Hex/IPA=90/10, 1.0 mL/min, 230 nm, 22° C.), 20.0 (major), 30.1 min, 90% ee; $[α]_D^{22}$=+37.79 (c 5.48, MeOH).

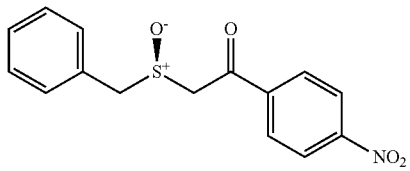 [SMILES: O=C(C[S@+]([O-])Cc1ccccc1)c1ccc([N+](=O)[O-])cc1]

(R)-2-(benzylsulfinyl)-1-(4-nitrophenyl)ethanone (12f), from 11f white solid; 95% yield; mp: 153.3-154.1° C.; $^1$H NMR (400 MHz, CDCl$_3$) δ 8.31 (d, J=8.8 Hz, 2H), 8.07 (d, J=8.8 Hz, 2H), 7.44-7.29 (m, 5H), 4.20 (ddd, J=25.7, 20.3, 10.1 Hz, 4H); $^{13}$C NMR (100 MHz, CDCl$_3$) δ 191.50, 150.79, 140.48, 130.37, 129.92, 129.10, 128.83, 128.80, 123.98, 57.93, 57.31; IR: 1685.79, 1604.77, 1531.48, 1419.61, 1346.31, 1053.13, 894.97 cm$^{-1}$; HRMS (ESI) calcd for C$_{15}$H$_{13}$NO$_4$S m/z [M+H]$^+$: 304.0644; found: 304.0638; HPLC analysis: Chiralcel AD-H (Hex/IPA=70/30, 1.0 mL/min, 230 nm, 22° C.), 20.8 (major), 27.7 min, 85% ee; $[α]_D^{22}$=-44.80 (c 1.66, CHCl$_3$).

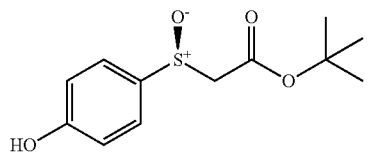 [SMILES: CC(C)(C)OC(=O)C[S@+]([O-])c1ccc(O)cc1]

(S)-tert-butyl 2-((4-hydroxyphenyl)sulfinyl)acetate (12g), from 11g

White solid; 88% yield; mp: 133.9-135.4° C.; $^1$H NMR (400 MHz, CDCl$_3$) δ 7.53 (d, J=8.5 Hz, 2H), 6.96 (d, J=8.5 Hz, 2H), 3.76 (dd, J=117.7, 13.8 Hz, 2H), 1.37 (s, 9H); $^{13}$C NMR (100 MHz, CDCl$_3$) δ 163.63, 160.90, 130.99, 127.00, 116.74, 83.60, 61.97, 27.83; IR: 3055.24, 1724.36, 1496.76, 1419.61, 1157.29, 1018.41, 894.97, 740.67 cm$^{-1}$; HRMS (ESI) calcd for C$_{12}$H$_{16}$O$_4$S m/z [M+H]$^+$: 257.0848; found: 257.0862; HPLC analysis: Chiralcel AS-H (Hex/IPA=80/20, 1.0 mL/min, 230 nm, 22° C.), 25.4 (major), 38.3 min, 61% ee; $[α]_D^{22}$=-58.27 (c 4.52, MeOH).

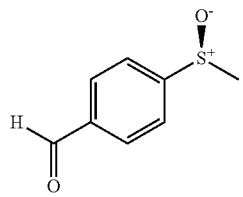

(S)-4-(methylsulfinyl)benzaldehyde (12h), from 11h

White solid; 82% yield; mp: 70.2-72.0° C.; $^1$H NMR (400 MHz, CDCl$_3$) δ 10.06 (s, 1H), 8.02 (d, J=8.4 Hz, 2H), 7.79 (d, J=8.2 Hz, 2H), 2.75 (s, 3H); $^{13}$C NMR (100 MHz, CDCl$_3$) δ 191.04, 152.34, 138.06, 130.32, 124.09, 43.67; IR: 2850.79, 2738.92, 1701.22, 1593.20, 1573.91, 1415.75, 1384.89, 1296.16, 1273.02, 1199.72, 1168.86, 1149.57, 1087.85, 956.69, 825.53, 736.81, 694.37 cm$^{-1}$; HRMS (ESI) calcd for C$_8$H$_8$O$_2$S m/z [M+H]$^+$:169.0323; found: 169.0326; HPLC analysis: Chiralcel AS-H (Hex/IPA=70/30, 1.0 mL/min, 230 nm, 22° C.), 31.9, 50.4 (major) min, 65% ee; $[α]_D^{22}$=-70.0 (c 2.76, MeOH).

Example 13: Gram-Scale Synthesis of Armodafinil

The practical utility of present catalysis system was further demonstrated by a gram-scale synthesis of psychostimulant drug Armodafinil (FIG. 17). This system uses the bisguanidinium 1b with (R,R)-configuration, which is a stereoisomer of (S,S)-1a that was referred to in the earlier examples. The oxidation of MDMMA 7a with a low loading of 0.25 mol % of (R,R)-1b was performed at room temperature for 8 h. Following by treatment with ammonia in methanol, (R)-Armodafinil 13 was obtained in 95% yield with an enantioselectivity of 91%.

Synthesis of Armodafinil 13:

A 10 mL round-bottomed flask was charged with a solution of methyl 2-(benzhydrylthio)acetate 7a (1.36 g, 5 mmol, 1.0 equiv.) and bis-guanidinium phase-transfer catalyst (R,R)-1b (17.6 mg, 0.0125 mmol, 0.0025 equiv.) in $^n$Bu$_2$O (100 mL). Then Na$_2$MoO$_4$.2H$_2$O (30 mg, 0.125 mmol, 0.025 equiv.), KHSO$_4$ (340 mg, 2.5 mmol, 0.5 equiv.) and H$_2$O$_2$(35%, 430 µL, 5 mmol, 1.0 equiv.) were added at room temperature. The resulting mixture was stirred vigorously and monitored by TLC and 7a was completely consumed within 8 h. Purification by running flash chromatography on a short silica gel column using CH$_2$Cl$_2$: EtOAc 2:1 as the eluent afforded the sulfoxide product with (R,R)-configuration, 1.32 g, 91% yield, 91% ee. Then the obtained sulfoxide (1.32 g, 4.58 mmol) was treated with 2M ammonical methanol (23 mL, 10.0 equiv.) and the resulting solution was stirred at room temperature for 24 h. Purification by running flash chromatography on a short silica gel column using CH$_2$Cl$_2$:MeOH 20:1 as the eluent afforded (R)-2-(benzhydrylsulfinyl)acetamide (13) as a white solid, 1.19 g, 95% yield.

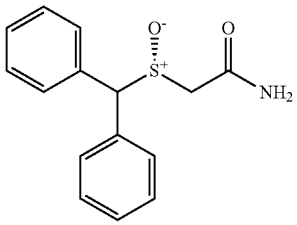 [SMILES: NC(=O)C[S@@+]([O-])C(c1ccccc1)c1ccccc1]

(R)-2-(benzhydrylsulfinyl)acetamide (13)

HPLC analysis: Chiralcel AS-H (Hex/IPA=50/50, 1.0 mL/min, 230 nm, 22° C.), 12.7, 28.8 (major) min, 91% ee; $[α]_D^{22}$=-16.25 (c 2.0, MeOH).

A single-crystal structure of (R)-13 is provided in FIG. 10C. Crystal data for (R)-13: [C$_{15}$H$_{15}$NO$_2$S], M=273.34, monoclinic, P 1 21 1, a=5.6324(3), b=26.1594(16), c=9.3139(5) Å, α=90, β=105.6796(19)°, γ=90°, V=1321.25 (13) Å$^3$, Z=4, $\rho_{calcd}$=1.374 g/cm$^3$, μ(CuKα)=0.242 mm$^{-1}$, T=103(2) K, Wavelength=0.71073 Å, colorless block. Bruker X8 CCD X-ray diffractionmeter; 8391 independent measured reflections, F$^2$ refinement, R$_1$(obs)=0.0446, wR$_2$(all)=0.0968, 7453 independent observed absorption-corrected reflections, 343 parameters. Crystallographic data for this paper have been deposited at the Cambridge Crystallographic Data Centre under deposition number CCDC 1456987.

Example 14: Mechanistic Insights of Molybdate System (Table 5, entries 4 and 5) and inorganic acids (Table 5, entries 6-8) were examined as additives. Indeed, except hydrochloric acid, they did accelerate the oxidation beyond the background reaction (Table 5, entry 1). However, the use of sulfuric acid as additive surprisingly achieved high enantioselectivity (Table 5, entry 7). Further decreases of the amount of aqueous H$_2$SO$_4$ to 5 mol % led to longer reaction time without affecting the enantioselectivity (Table 5, entries 9 and 10) but the loss of enantioselectivity and reactivity were observed with only 1 mol % of aqueous H$_2$SO$_4$ (Table 5, entry 11) (Chengxia Miao et al. *J. Am. Chem. Soc.* 138, 936-943 (2016)). Moreover, sulfuric acid itself cannot act as an activator towards hydrogen peroxide in the absence of molybdate salt (Table 5, entry 13). These results suggest that

TABLE 5

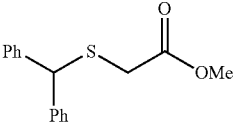

| Entry | Cat | Additive | Time (min) | Yield (%)$^b$ | ee (%)$^c$ |
|---|---|---|---|---|---|
| 1 | (R,R)-1b | — | 1440 | 15 | −5 |
| 2 | (R,R)-1b | KHSO$_4$ | 30 | 94 | −92 |
| 3 | (R,R)-1b | TBAHSO$_4$ | 60 | 89 | −89 |
| 4 | (R,R)-1b | CH$_3$SO$_3$H | 120 | 84 | −5 |
| 5 | (R,R)-1b | CF$_3$SO$_3$H | 60 | 98 | 0 |
| 6$^d$ | (R,R)-1b | H$_3$PO$_4$ | 240 | 89 | −17 |
| 7$^d$ | (R,R)-1b | H$_2$SO$_4$ | 10 | 99 | −95 |
| 8$^d$ | (R,R)-1b | HCl | 240 | 17 | −2 |
| 9$^d$ | (R,R)-1b | H$_2$SO$_4$ (0.1 equiv.) | 10 | 99 | −90 |
| 10$^d$ | (R,R)-1b | H$_2$SO$_4$ (0.05 equiv.) | 90 | 80 | −91 |
| 11$^d$ | (R,R)-1b | H$_2$SO$_4$ (0.01 equiv.) | 1440 | 27 | −2 |
| 12$^{d,e}$ | (R,R)-1b | H$_2$SO$_4$ | 240 | 0 | NA |
| 13$^e$ | (R,R)-1c | — | 30 | 95 | −91 |
| 14$^{e,f}$ | (R,R)-1c | — | 30 | 97 | −80 |

Unless otherwise indicated, reaction was performed with 0.05 mmol of 7a in the presence of 1 mol % of chiral bisguanidinium (R,R)-1b or (R,R)-1c and 2.5 mol % of Na$_2$MoO$_4$•2H$_2$O in 1.0 mL of $^i$Pr$_2$O at room temperature.
$^b$Yield of the isolated product.
$^c$Determined by HPLC analysis.
$^d$Aqueous H$_3$PO$_4$, H$_2$SO$_4$, HCl were freshly prepared with concentration of 1.0 M.
$^e$Without Na$_2$MoO$_4$•2H$_2$O.
$^f$1.0 equivalent of (R,R)-1c was used in the absence of aqueous hydrogen peroxide co-oxidant.
(R,R)-1c was obtained by an experiment under similar oxidative condition but without the addition of substrate MDMMA 7a (see Synthetic Protocol of Isolated Complex (R,R)-1c, FIG. 14) using bisguanidinium (R,R)-1b.
TBA = tetrabutylammonium.

To understand how the catalytic system works, control experiments were also carried out based on General Procedure 3, unless otherwise stated (Table 5). In the comparison of entries 2 and 3, with 0.5 equivalent of tetrabutylammonium bisulfate (TBAHSO$_4$) as the additive and only 1 mol % of chiral bisguanidinium (R,R)-1b, the reaction still provided a high degree of stereocontrol (89% vs 92%) but at a relatively slow rate. This indicated that the chiral bisguanidinium dication is much more efficient to activate or interact with the real anionic intermediates than tetrabutylammonium cation. Additionally, several organic sulfonic acids both molybdate and sulfate are included in the real active oxidant species (Fabian Taube, et al., *J. Chem. Soc., Dalton Trans.*, 1002-1008 (2002)).

More importantly, previously prepared (R,R)-1c was applied in the oxidative reaction without the addition of any additive or molybdate species. Consistent performance in the sulfoxidation of MDMMA 7a by using 1 mol % of (R,R)-1c was observed (Table 5, entry 14). Such observation clearly indicated (R,R)-1c is the catalytically active species and an efficient ion-pairing catalyst for enantiodiscrimination. Furthermore, upon treatment of substrate 7a with stoichiometric equivalent of (R,R)-1c in the absence of hydrogen peroxide terminal co-oxidant, oxidative product 8a was achieved in high yield and good enantioselectivity (Table 5, entry 14). These direct evidences strongly indicated that (R,R)-1c is the true oxidizing species involving peroxo moiety—which is further explored below in the subsequent examples.

Example 15: Structural Analysis of (R,R)-1c

X-Ray Single Crystal Diffraction

A suitable crystal of (R,R)-1c for X-ray single crystal diffraction was obtained and the structure of (R,R)-1c was successfully resolved, with bisguanidinium dication and oxodiperoxomolybdosulfate dianion as two components for this ion-pair complex (FIG. 8). According to the X-ray data, it can be found that the achiral anionic metallic species locates at one side of chiral dicationic counterpart backbone with approaching to the centric bisguanidinium moiety. Moreover, the coordination mode of anionic part was clearly elucidated (FIG. 8).

This dinuclear oxodiperoxomolybdosulfate moiety has a symmetric condensate structure comprising one bridging peroxo ligand, one side-on peroxo group and a terminal oxo ligand on each Mo center, and one sulfate group as a bipodal ligand to the two Mo atoms (Laurent Salles, et al., *Bull. Soc. Chim. Fr.* 133, 319-328 (1996)). Thus each Mo atom is 7-coordinated by oxygen atoms in a pentagonal bipyramidal arrangement (Laurent Salles et al. *Polyhedron* 26, 4786-4792 (2007)). The two associated pentagonal bipyramids share one edge [$O_9 \ldots O_{10}$] on the non-basal plane and the two Mo atoms are connected by two $\mu$-$\eta^1$:$\eta^2$-peroxo bridges [$O_8$-$O_9$ and $O_{11}$—$O_{10}$]. Both $Mo_1$—$O_5$ and $Mo_2$—$O_{12}$ bonds have the same length (1.659(7)) Å) which falls into a typical range for Mo=O bond. Generally, bridging peroxo $O_8$-$O_9$ (1.482(9) Å) and $O_{10}$-$O_{11}$ (1.473(10) Å) bond lengths are slightly longer than the side-on peroxo $O_6$-$O_7$ (1.458(10) Å) and $O_{13}$-$O_{14}$ (1.467(10) Å) bond lengths. Moreover, the two side-on peroxo groups seem to be the active oxygen donors, which can transfer two equivalents of active oxygen atom to the substrate (Dylan J. Thompson, et al., *Inorg. Chim. Acta* 437, 103-109 (2015)).

$^{95}$Mo NMR $^{95}$Mo NMR spectral data of this novel bisguanidinium oxodiperoxomolybdosulfate complex (R,R)-1c in $d_7$-DMF solvent is reported for the first time by using the external reference 2 M $Na_2MoO_4 \cdot 2H_2O$ solution in $D_2O$, assigned to 0 ppm. The resonance occurred at −199.29 ppm (FIG. 13B) which is attributed to the region characteristic of the oxodiperoxomolybdate species (Andrew C. Dengel, et. al., *J. Chem. Soc., Dalton Trans.*, 991-995 (1987); V. Nardello, J, et. al., *Inorg. Chem.* 34, 4950-4957 (1995); Jeena Jyoti Boruah, et. al., *Green Chem.* 15, 2944-2959 (2013); Jeena Jyoti Boruah, et. al., *Polyhedron* 52, 246-254 (2013)). The appearance of a single and relatively sharp peak in the $^{95}$Mo NMR spectrum of (R,R)-1c indicated the presence of a single coordination environment for the oxodiperoxomolybdosulfate species with a high symmetric coordination mode. In addition, the analogue to (R,R)-1c with di-tetrabutylammonium (TBA) counter cation was prepared following the reported procedure and the resonance of it also occurred at −199.29 ppm (FIG. 13A) (Laurent Salles, et. al., *Bull. Soc. Chim. Fr.* 133, 319-328 (1996)). However, this di-tetrabutylammonium oxodiperoxomolybdosulfate complex has poor performance in the oxidative reaction of sulfide 7a, less than 10% conversion within 2 hours, which indicates the catalytic reactivity of metallic anion is strongly affected by the pattern of ion-pairing.

IR (R,R)-1c was also characterised by IR technique (see Example 1 and FIG. 16). The sharp and strong peaks at 972.12 and 871.82 cm$^{-1}$ are assigned to (Mo=O) and (O-O) stretching frequencies, respectively. And the peaks at 663.51 and 590.22 cm$^{-1}$ are characteristic of the asymmetric and symmetric stretching of (Mo—($O_2$)) moieties, respectively (Andrew C. Dengel, et. al., *J. Chem. Soc., Dalton Trans.*, 991-995 (1987)). The peaks at 1114.86, 1076.28, 1049.27 cm$^{-1}$ are tentatively assigned to the $SO_4^{2-}$ ligand with a lower symmetry when it coordinates to the Mo atom (Fabian Taube, et. al, *J. Chem. Soc., Dalton Trans.*, 1002-1008 (2002)).

Example 16: Use of (R,R)-1c as the Sole Oxidant

TABLE 6

(R,R)-1c as the sole oxidant.

| Entry | Cat | x | Time (min) | Yield (%)[b] | ee (%)[c] |
|---|---|---|---|---|---|
| 1 | (R,R)-1c | 100 | 30 | 97 | −80 |
| 2 | (R,R)-1c | 50 | 120 | 79[d] | −37 |
| 3 | (R,R)-1c | 25 | 120 | 50[d] | −31 |
| 4[e] | — | 1 | 120 | 0 | — |
| 5[f] | — | 1 | 120 | 99 | 89 |

Unless otherwise indicated, reaction was performed with 0.05 mmol of 7a in the presence of chiral bisguanidinium (R,R)-1c in 1.0 mL of $^i$Pr$_2$O at room temperature.
[b]Yield of the isolated product.
[c]Determined by HPLC analysis.
[d]Determined by $^1$H NMR analysis.
[e]Catalyst recycled from reaction in entries 2 and 3 was used with the addition of one equivalent of aqueous $H_2O_2$.
[f]Catalyst recycled from reaction in entries 2 and 3 was used with the addition of 0.5 equivalent of KHSO$_4$ and one equivalent of aqueous $H_2O_2$.

The effect of varying a stoichiometric amount of (R,R)-1c as the sole oxidant was examined in the asymmetric oxidation of sulfide 7a. In the presence of one equivalent of (R,R)-1c, the reaction proceeded well to afford the product in 97% yield with a good enantioselectivity of 80% (Table 6, entry 1). However, the lower of its amount to 0.5 equivalent or 0.25 equivalent, a dramatic decrease of enantioselectivity was observed. Employing 0.25 equivalent of (R,R)-1c in our current system led to the formation of 50% sulfoxide (determined by crude $^1$H NMR—see FIG. 13). Without wishing to be bound by theory, this result appears to show that there is a transfer of two equivalents of active oxygen from (R,R)-1c to substrate 7a.

Without wishing to be bound by theory, the significant deterioration of enantioselectivity is probably ascribed to insufficient stereocontrol of the oxomonoperoxosulfato molybdenum dianion of (R,R)-1c in the transfer of second active oxygen. In other words, the second active oxygen of A should be out of the catalytic cycle in the presence of terminal oxidant hydrogen peroxide in order to maintain the dimeric structure which highly affect the enantiofacial discrimination process before the formation of B. Upon the completion of this stoichiometric reaction, the catalyst was recovered by running a flash silica column, but the reaction has shown loss of activity of the catalyst in the presence of $H_2O_2$, which probably indicates the collapse of the dimeric structure of the anionic part (Table 6, entry 4). It was noteworthy that the catalyst can be remarkably regenerated and reactivated by the addition of 0.5 equivalent of $KHSO_4$ in the reaction to afford high enantioselectivity again (Table 6, entry 5).

Based on the aforementioned experimental results, a plausible mechanistic pathway was tentatively proposed (see FIG. 12).

The invention claimed is:

1. A complex of formula (I), comprising an organic cation (A) and an inorganic anion (B):

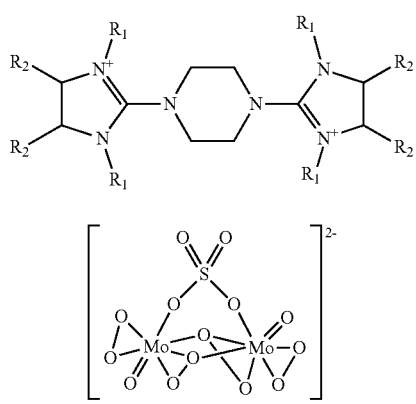

wherein: each $R_1$ independently represents $C_{1-3}$ alkyl-aryl or $C_{1-3}$ alkyl-Het$^a$, which aryl or Het$^a$ groups are unsubstituted or are substituted by from one to five $R_3$ substituents;

each $R_2$ independently represents aryl, which group is unsubstituted or substituted by from one to five $R_4$ substituents;

Het$^a$ represents a 4- to 14-membered heterocyclic group containing one or more heteroatoms selected from O, S and N, which heterocyclic group comprises one, two or three rings;

each $R_3$ and $R_4$ independently represents halo, branched or unbranched $C_{1-6}$ alkyl, branched or unbranched $C_{2-6}$ alkenyl, branched or unbranched $C_{2-6}$ alkynyl; $C_{3-6}$ cycloalkyl, aryl or $OR_5$;

$R_5$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl or aryl, wherein alkyl, alkenyl, alkynyl, cycloalkyl, and aryl, when present in $R_3$, $R_4$, and $R_5$, are optionally substituted by one or more halogen atoms.

2. The complex of claim 1, wherein:
   each $R_1$ independently represents $C_{1-3}$ alkyl-phenyl, which phenyl group is substituted by from two to four $R_3$ substituents;
   each $R_2$ independently represents phenyl, which group is unsubstituted or substituted by from one to two $R_4$ substituents;
   each $R_3$ and $R_4$ independently represents fluoro, branched or unbranched $C_{1-6}$ alkyl, $C_{3-6}$ cycloalkyl or $OR_5$;
   $R_5$ represents branched or unbranched $C_{1-3}$ alkyl or $C_{3-6}$ cycloalkyl,
   wherein alkyl and cycloalkyl, when present in $R_3$, $R_4$, and $R_5$, are optionally substituted by one or more halogen atoms.

3. The complex of claim 2, wherein:
   each $R_1$ independently represents $CH_2$-phenyl, which phenyl group is substituted by from two to three $R_3$ substituents;
   each $R_2$ independently represents unsubstituted phenyl;
   each $R_3$ independently represents fluoro, branched or unbranched $C_{3-5}$ alkyl or $OR_5$; and $R_5$ represents branched or unbranched $C_{1-3}$ alkyl optionally substituted by one or more halogen atoms.

4. The complex of claim 1, wherein the organic cation (A) is enantioenriched.

5. The complex of claim 1, where the organic cation (A) is selected from:
   (i) 1,4-bis((4S,5S)-1,3-bis(3,5-di-tert-butylbenzyl)-4,5-diphenylimidazolidin-2-ylidene)piperazine-1,4-diium;
   (ii) 1,4-bis((4R,5R)-1,3-bis(3,5-di-tert-butylbenzyl)-4,5-diphenylimidazolidin-2-ylidene)piperazine-1,4-diium;
   (iii) 1,4-bis((4S,5S)-1,3-bis(3,5-di-tert-butyl-4-methoxybenzyl)-4,5-diphenylimidazolidin-2-ylidene)piperazine-1,4-diium;
   (iv) 1,4-bis((4R,5R)-1,3-bis(3,5-di-tert-butyl-4-methoxybenzyl)-4,5-diphenylimidazolidin-2-ylidene)piperazine-1,4-diium;
   (v) 1,4-bis((4S,5S)-1,3-bis(3,5-di-tert-butyl-4-fluorobenzyl)-4,5-diphenylimidazolidin-2-ylidene)piperazine-1,4-diium; and
   (vi) 1,4-bis((4R,5R)-1,3-bis(3,5-di-tert-butyl-4-fluorobenzyl)-4,5-diphenylimidazolidin-2-ylidene)piperazine-1,4-diium.

6. The complex of claim 5, where the organic cation (A) is selected from:
   (i) 1,4-bis((4S,5S)-1,3-bis(3,5-di-tert-butylbenzyl)-4,5-diphenylimidazolidin-2-ylidene)piperazine-1,4-diium; and
   (ii) 1,4-bis((4R,5R)-1,3-bis(3,5-di-tert-butylbenzyl)-4,5-diphenylimidazolidin-2-ylidene)piperazine-1,4-diium.

7. A process of manufacturing a sulfoxide, comprising reacting a compound of formula (II):

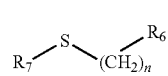

in the presence of a complex of formula (I), as defined in claim 1, wherein in the compound of formula (II):
$R_6$ represents H, branched or unbranched $C_{1-6}$ alkyl, branched or unbranched $C_{2-6}$ alkenyl, branched or unbranched $C_{2-6}$ alkynyl, $C_{3-6}$ cycloalkyl, $C(O)R_{10}$, $C(O)OR_{11}$ or $OR_{12}$, wherein alkyl, alkenyl, alkynyl, and cycloalkyl, when present in $R_6$, are optionally substituted by one or more substituents selected from halo, $OR_8$, and $C(O)R_9$;

$R_7$ represents $CH(R_{13})(R_{14})$, $Het^b$ or aryl, wherein $Het^b$ and aryl, when present in $R_7$, are optionally substituted by one or more substituents selected from halo, $NO_2$, CN, $C(O)R_{15}$, $OR_{16}$, and branched or unbranched $C_{1-6}$ alkyl optionally substituted by one or more halo atoms;

$R_{13}$ and $R_{14}$ each independently represent H, aryl or $Het^c$, provided that at least one of $R_{13}$ and $R_{14}$ is not H, wherein aryl and $Het^c$, when present in $R_{13}$ or $R_{14}$, are optionally substituted by one or more substituents selected from halo, branched or unbranched $C_{1-6}$ alkyl, $C(O)R_{17}$ and $OR_{18}$;

$R_8$, $R_{12}$, $R_{16}$ and $R_{18}$ each independently represent H, $C(O)R_{19}$ or a branched or unbranched $C_{1-6}$ alkyl optionally substituted by one or more halo atoms;

$R_9$, $R_{10}$, $R_{15}$ and $R_{17}$ each independently represent $OR_{20}$, $N(R_{20'})(R_{20''})$ or a branched or unbranched $C_{1-6}$ alkyl optionally substituted by one or more halo atoms;

$R_{11}$ represents a branched or unbranched $C_{1-6}$ alkyl optionally substituted by one or more halo atoms;

$R_{19}$, $R_{20}$, $R_{20'}$ and $R_{20''}$ each independently represent H or a branched or unbranched $C_{1-6}$ alkyl optionally substituted by one or more halo atoms;

$Het^b$ and $Het^c$ represents a 4- to 14-membered heteroaromatic group containing one or more heteroatoms selected from O, S and N, which heteroaromatic group comprises one, two or three rings; and n represents from 1 to 10.

8. The process of claim 7, wherein in the compound of formula (II):

$R_6$ represents branched or unbranched $C_{1-4}$ alkyl, branched or unbranched $C_{2-4}$ alkenyl, $C(O)R_{10}$, or $C(O)OR_{11}$, wherein alkyl and alkenyl, when present in $R_6$, are optionally substituted by one or more substituents selected from halo and $C(O)R_9$;

$R_9$ and $R_{10}$ each independently represent $OR_{20}$ or a branched or unbranched $C_{1-4}$ alkyl optionally substituted by one or more halo atoms;

$R_{11}$ represents a branched or unbranched $C_{1-4}$ alkyl optionally substituted by one or more halo atoms.

9. The process of claim 7, wherein in the compound of formula (II): $R_7$ represents $CH(R_{13})(R_{14})$, phenyl or naphthyl, wherein phenyl or naphthyl, when present in $R_7$, are optionally substituted by one or more substituents selected from halo, $C(O)R_{15}$, $OR_{16}$, and branched or unbranched $C_{1-6}$ alkyl optionally substituted by one or more halo atoms;

$R_{13}$ and $R_{14}$ each independently represent H, phenyl or naphthyl, provided that at least one of $R_{13}$ and $R_{14}$ is not H, wherein phenyl and naphthyl, when present in $R_{13}$ or $R_{14}$, are optionally substituted by one or more substituents selected from halo, branched or unbranched $C_{1-3}$ alkyl, $C(O)R_{17}$ and $OR_{18}$.

10. The process of claim 7, wherein the process provides an enantiomerically enriched sulfoxide as the product.

11. The process of claim 7, wherein the process further comprises using the complex of formula (I) in a catalytic amount in combination with at least one molar equivalent, relative to the compound of formula (II), of an oxidising agent.

12. The process of claim 11, wherein the process provides the complex of formula (I) in situ through reaction of an organic cation (A) with a molybdenum-containing salt and a sulfur-containing additive where:

the organic cation (A) is provided as a salt with a counterion selected from chloride;

the molybdenum-containing salt is $M_2MoO_4$ or $(NH_4)_6MoO_{24}$ or solvates thereof, where M represents Na, K or Li; and the sulfur-containing additive is selected from one or more of the group consisting of $NaHSO_4$, $KHSO_4$, $H_2SO_4$, and tetrabutylammonium bisulfate ($TBAHSO_4$).

* * * * *